United States Patent
Siems et al.

(10) Patent No.: US 10,472,385 B2
(45) Date of Patent: Nov. 12, 2019

(54) TRITERPENE-GLYCOSIDES AS SWEETENERS OR SWEETENER ENHANCERS

(71) Applicant: Analyticon Discovery GmbH, Potsdam (DE)

(72) Inventors: Karsten Siems, Michendorf (DE); Grit Kluge, Trebbin (DE); Sven Jakupovic, Berlin (DE); Gregor Hetterling, Berlin (DE); Fotini Tschirintzi, Berlin (DE)

(73) Assignee: Analyticon Discovery GmbH, Potsdam (DE)

( * ) Notice: Subject to any disclaimer, the term of this patent is extended or adjusted under 35 U.S.C. 154(b) by 169 days.

(21) Appl. No.: 15/101,189

(22) PCT Filed: Dec. 5, 2013

(86) PCT No.: PCT/EP2013/075724
§ 371 (c)(1),
(2) Date: Jun. 2, 2016

(87) PCT Pub. No.: WO2015/082012
PCT Pub. Date: Jun. 11, 2015

(65) Prior Publication Data
US 2017/0029458 A1    Feb. 2, 2017

(51) Int. Cl.
| | |
|---|---|
| A23L 27/30 | (2016.01) |
| C07J 17/00 | (2006.01) |
| A23L 27/00 | (2016.01) |
| A23G 3/36 | (2006.01) |
| A23G 4/06 | (2006.01) |
| A23G 4/08 | (2006.01) |
| A61K 8/60 | (2006.01) |
| A61Q 11/00 | (2006.01) |

(52) U.S. Cl.
CPC .............. *C07J 17/005* (2013.01); *A23G 3/36* (2013.01); *A23G 4/06* (2013.01); *A23G 4/08* (2013.01); *A23L 27/00* (2016.08); *A23L 27/30* (2016.08); *A23L 27/36* (2016.08); *A61K 8/602* (2013.01); *A61Q 11/00* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,084,010 A | 4/1978 | Takemoto et al. | |
| 2010/0272838 A1* | 10/2010 | Prendergast | A61K 36/42 424/758 |
| 2011/0027413 A1 | 2/2011 | Jia et al. | |
| 2012/0059071 A1 | 3/2012 | Markosyan | |

FOREIGN PATENT DOCUMENTS

| | | | | |
|---|---|---|---|---|
| JP | S57-86266 A | 5/1982 | | |
| WO | WO-2008149253 A2 * | 12/2008 | ............... | A23L 2/60 |

OTHER PUBLICATIONS

Chemblink page showing CAS REG ID 88901-36-4, 2019.*

* cited by examiner

*Primary Examiner* — Traviss C McIntosh, III
(74) *Attorney, Agent, or Firm* — Dilworth & Barrese, LLP

(57) ABSTRACT

Suggested are triterpene-glycoside compounds, which are obtainable by the extraction of *Momordica grosvenorii* (*Siraitia grosvenori*) which are useful as a sweetener or sweetener enhancer in preparations and compositions, especially oral edible compositions.

6 Claims, 18 Drawing Sheets

Figure 1: H-NMR of compound Aa
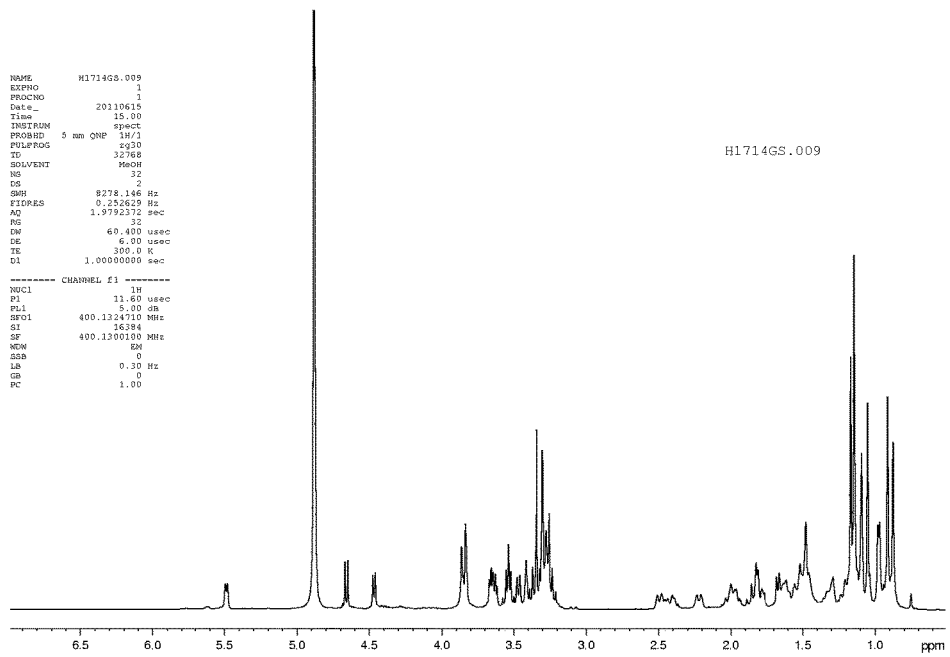
Figure 2: H-NMR of compound Bb
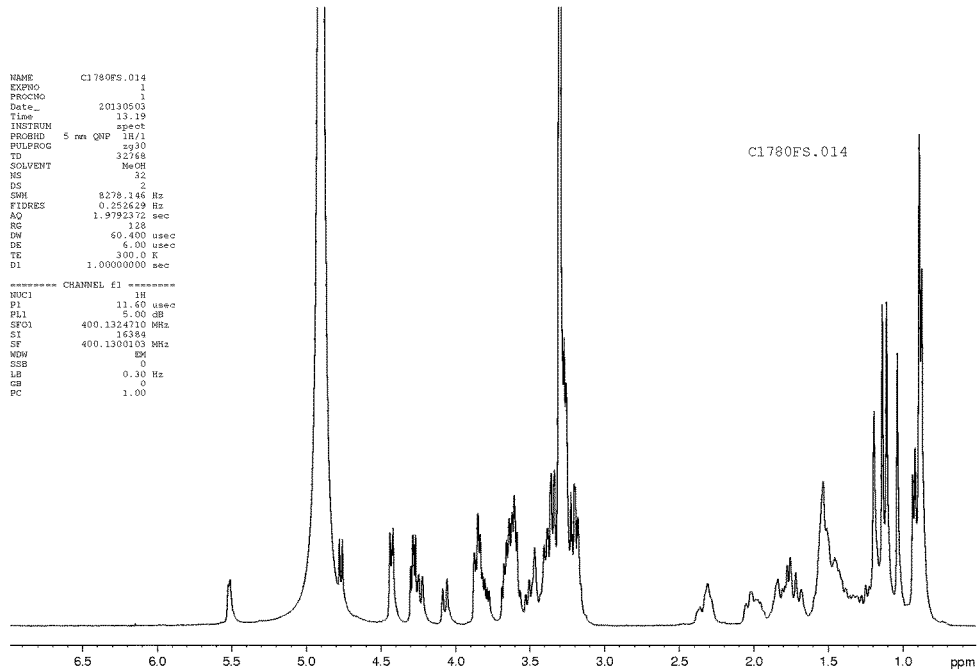

Figure 3: H-NMR of compound Cc
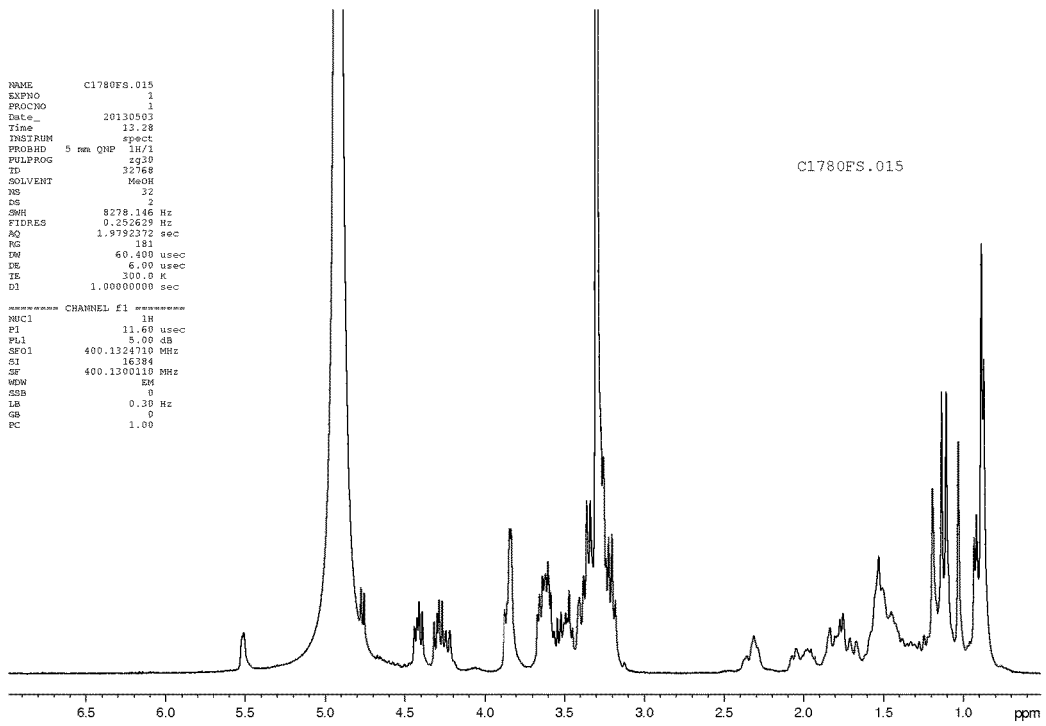
Figure 4: H-NMR of compound Dd
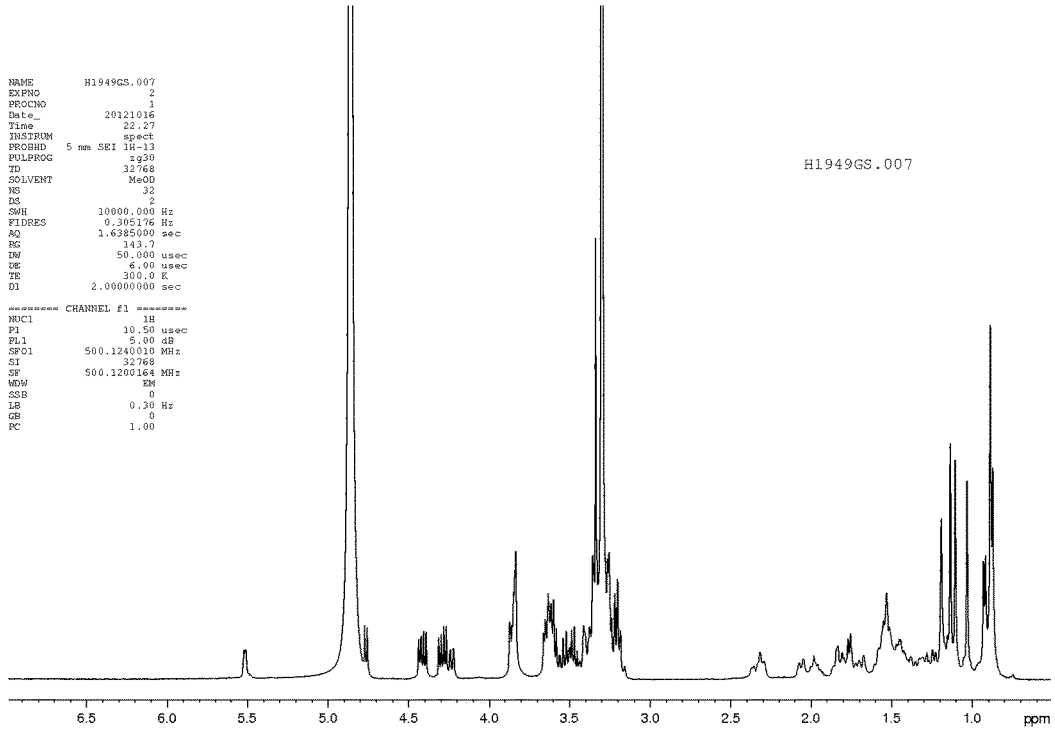

Figure 5: H-NMR of compound Ee
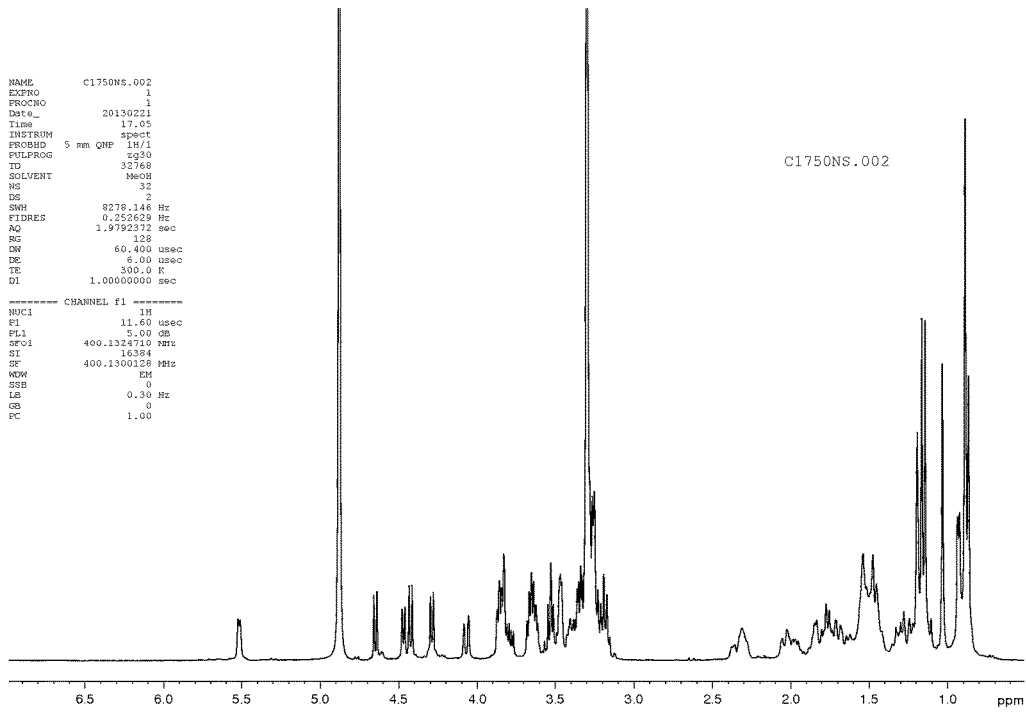
Figure 6: H-NMR of compound Ff
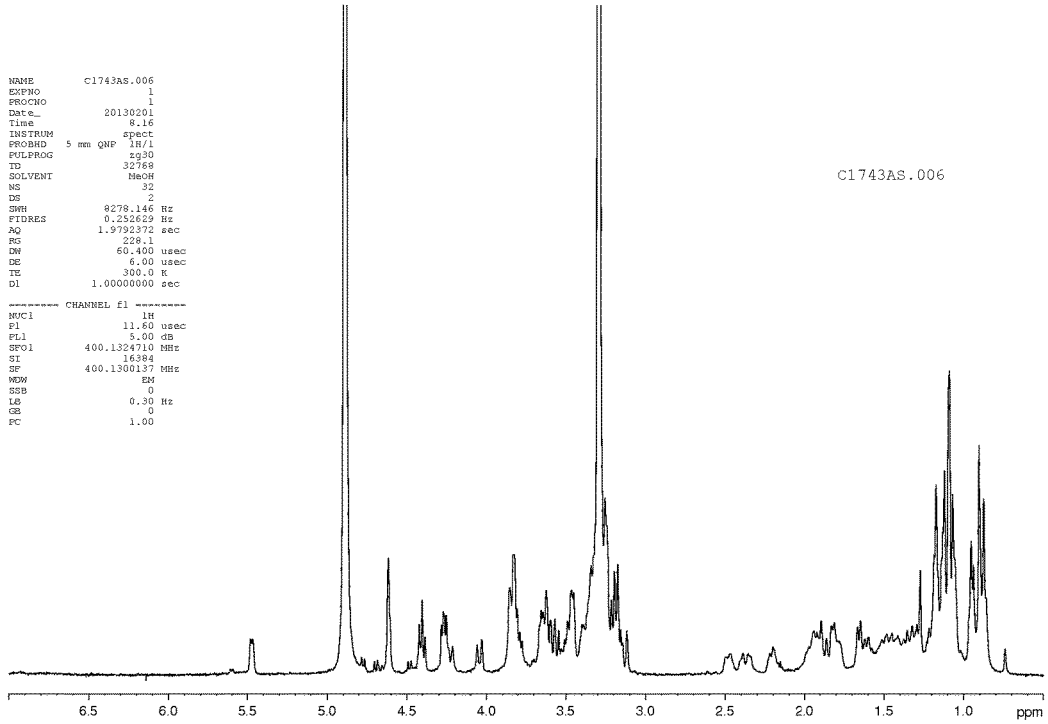

Figure 7: H-NMR of compound Gg
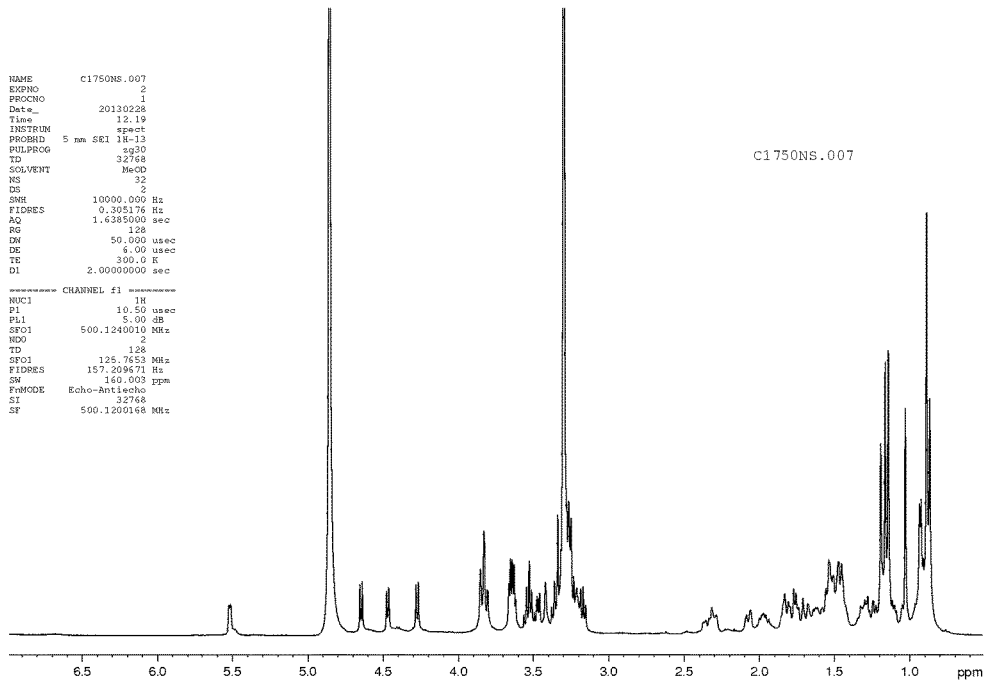
Figure 8: H-NMR of compound Hh
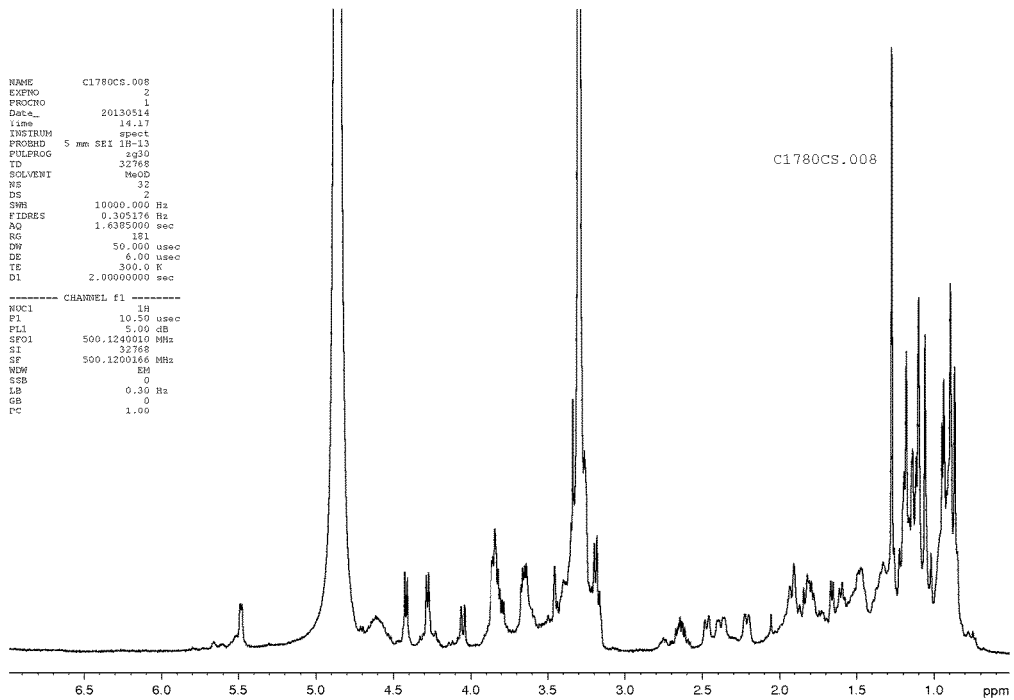

Figure 9: H-NMR of compound Jj
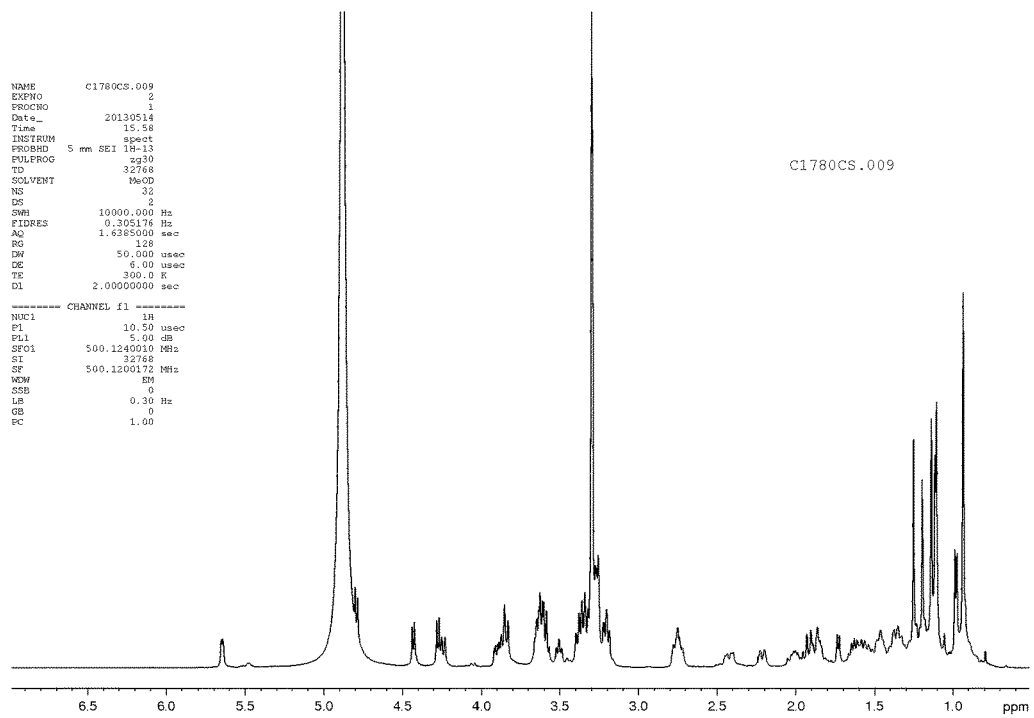
Figure 10: H-NMR of compound Kk
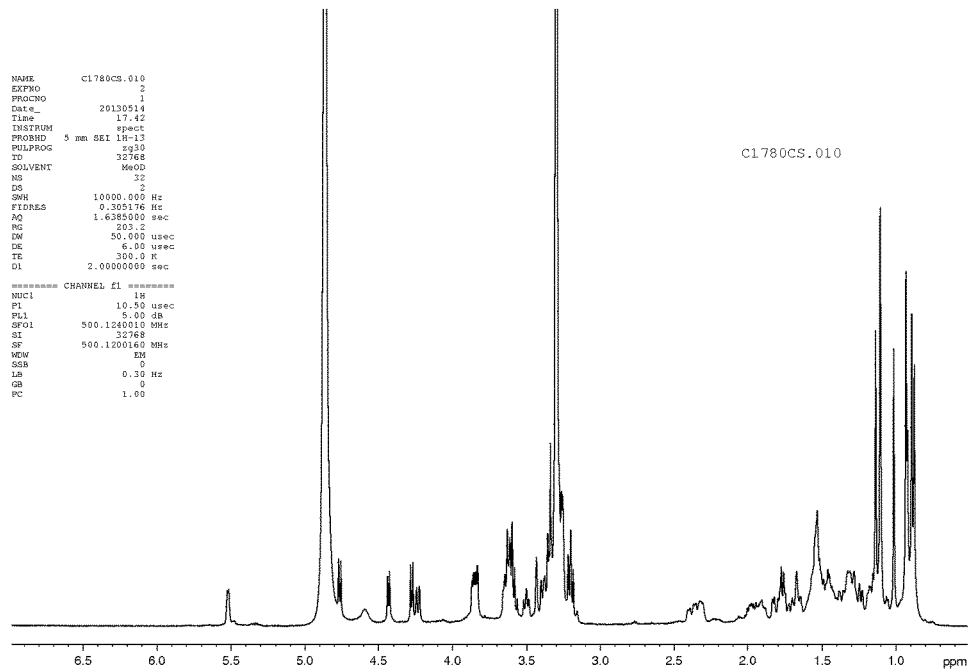

Figure 11: H-NMR of compound Ll
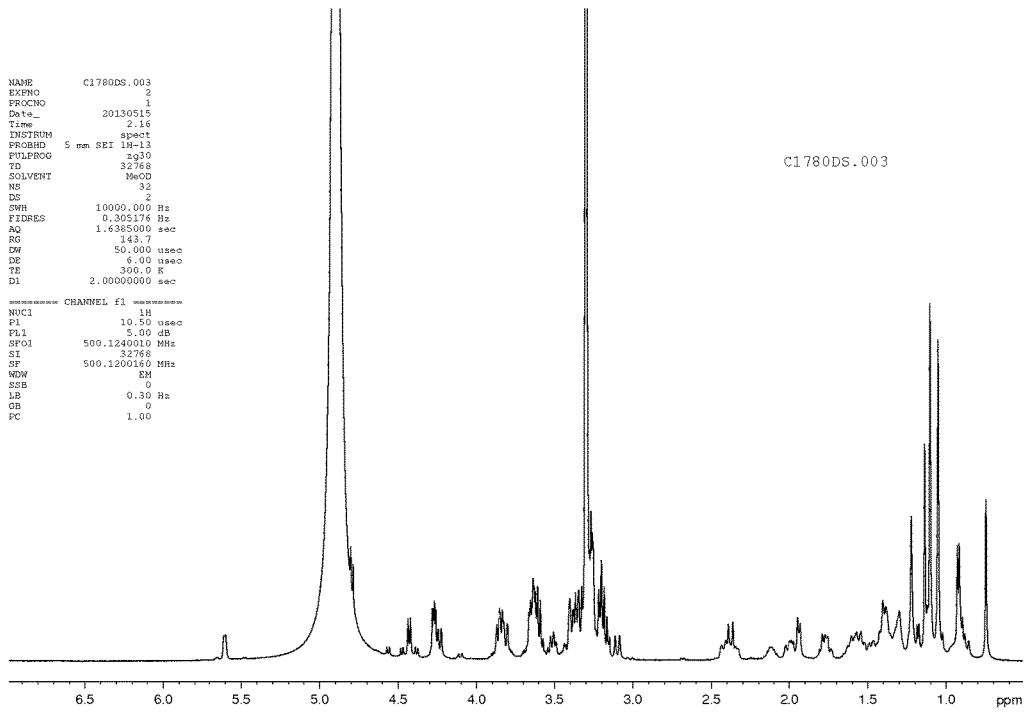
Figure 12: H-NMR of compound Mm
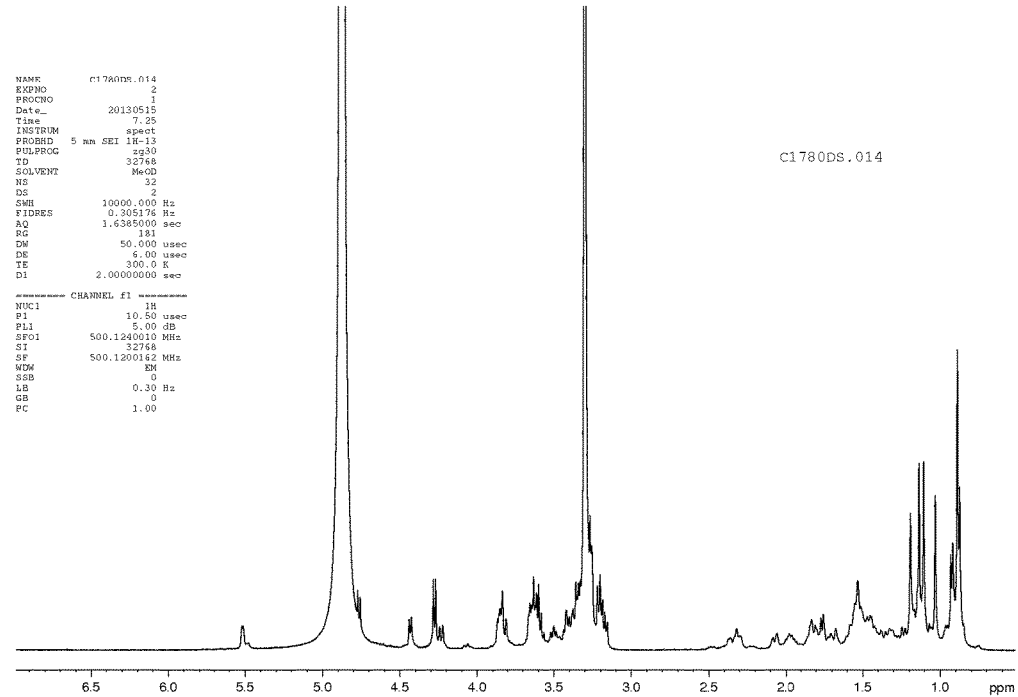

Figure 13: ESI-MS of compound Aa
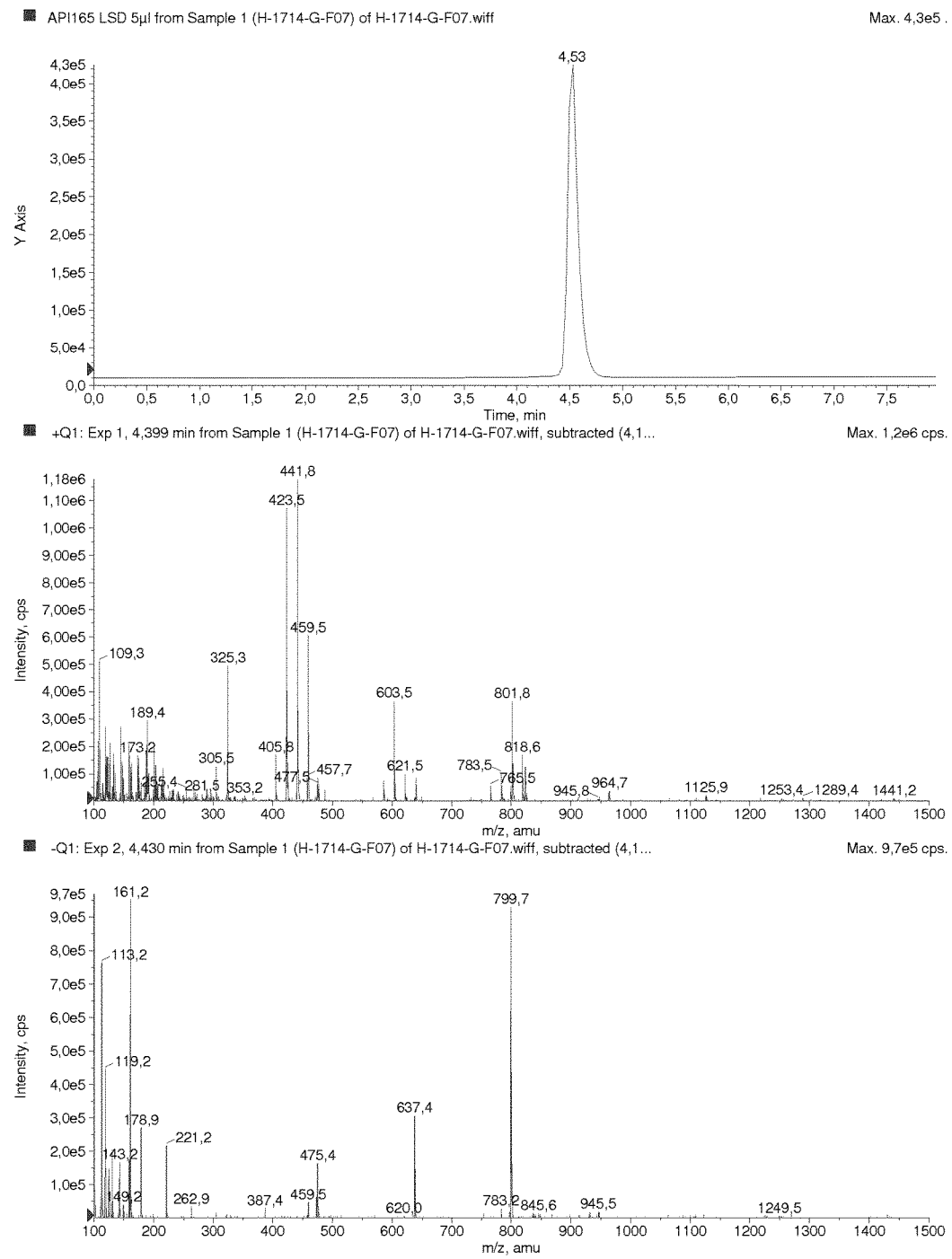

Figure 14: ESI-MS of compound Bb
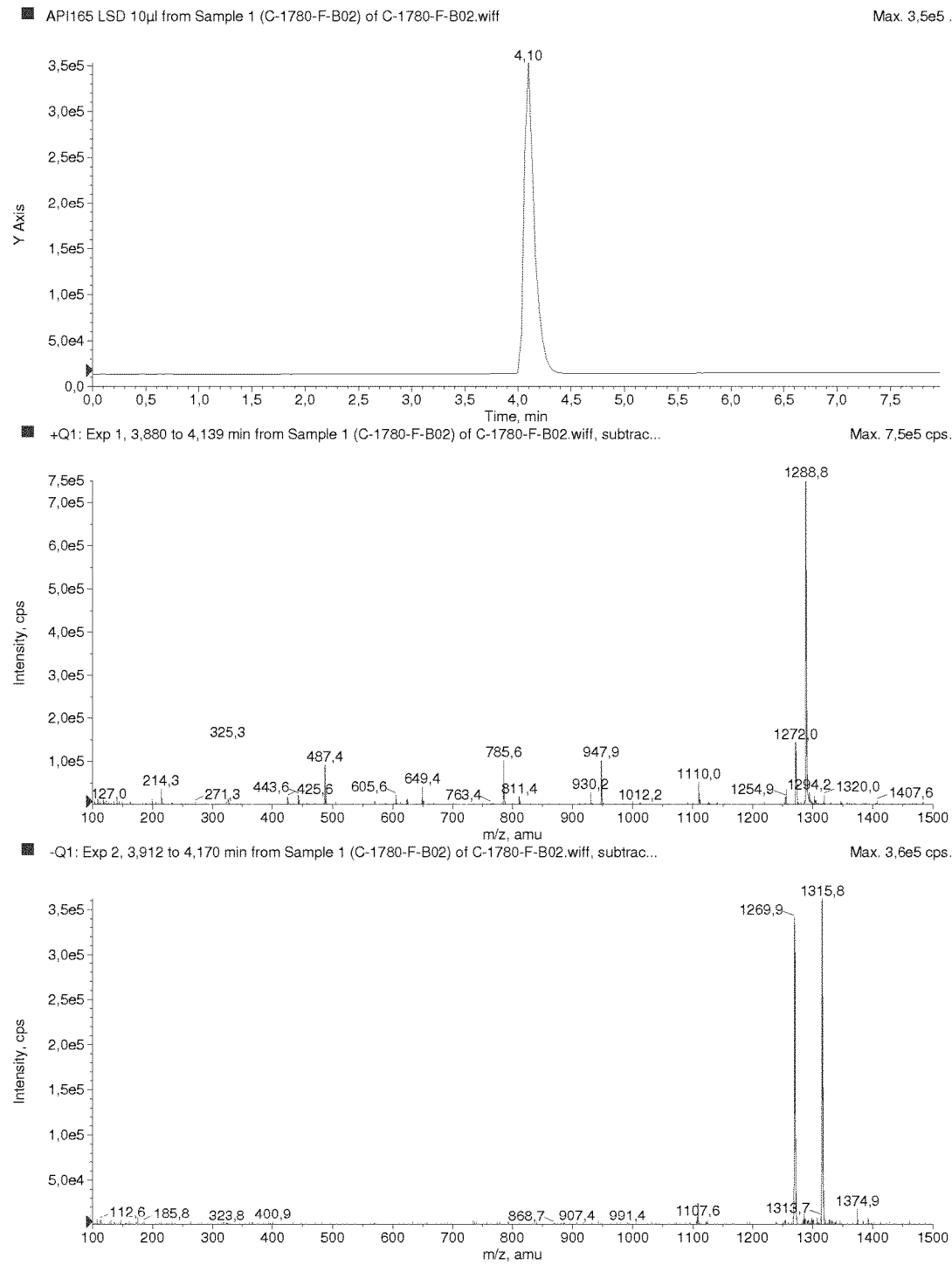

Figure 15: ESI-MS of compound Cc
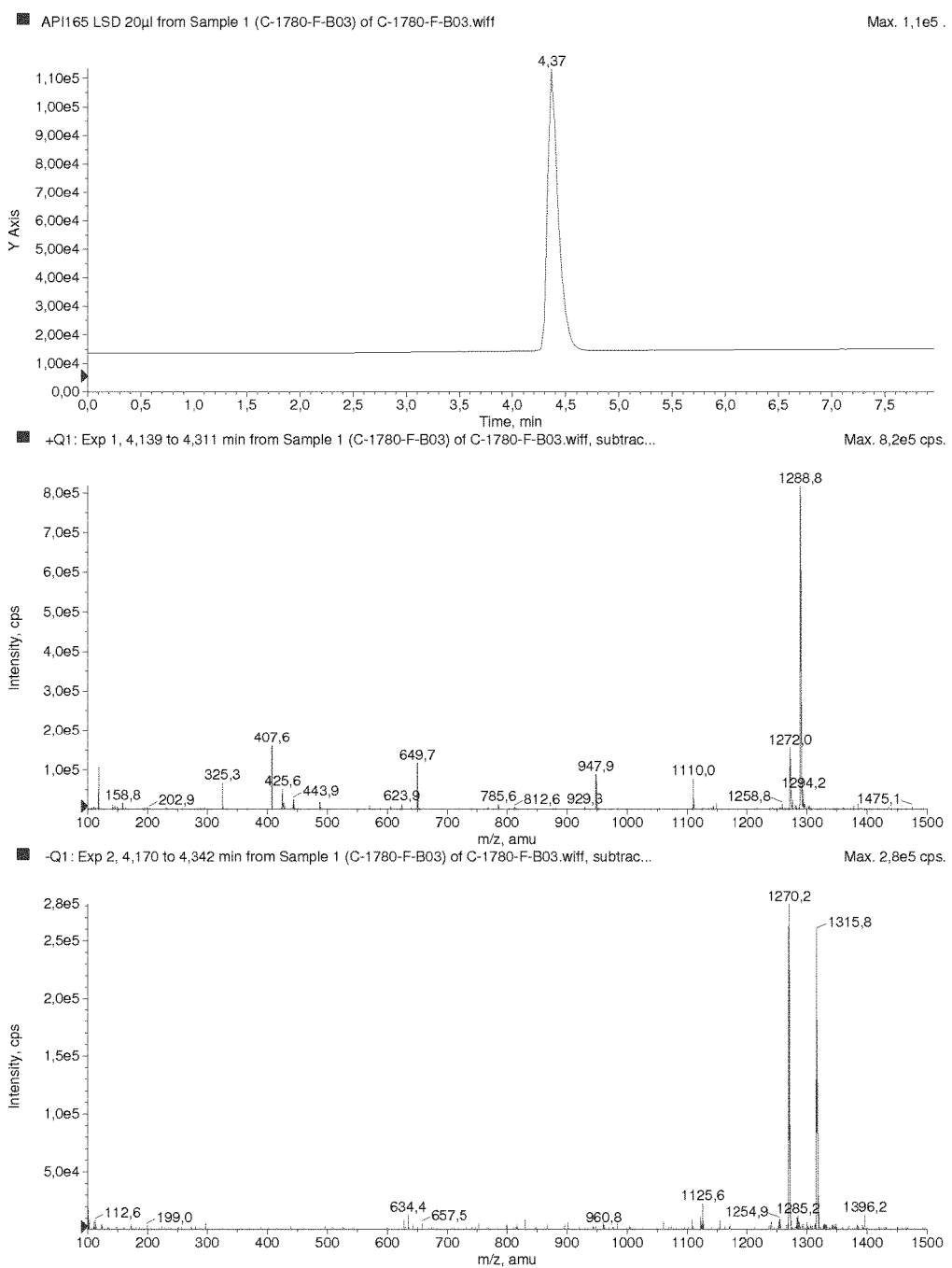

Figure 16: ESI-MS of compound Dd
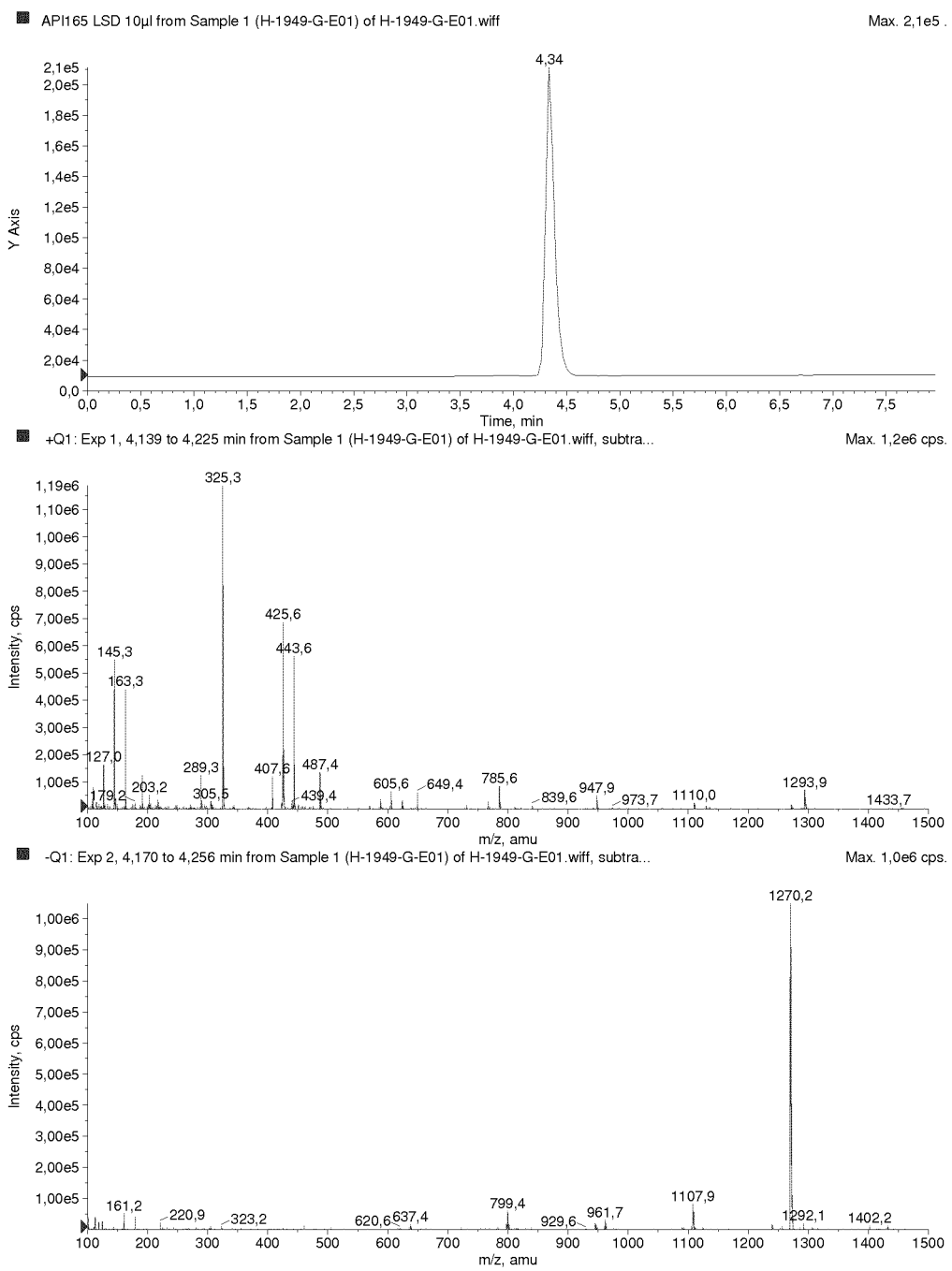

Figure 17: ESI-MS of compound Ee
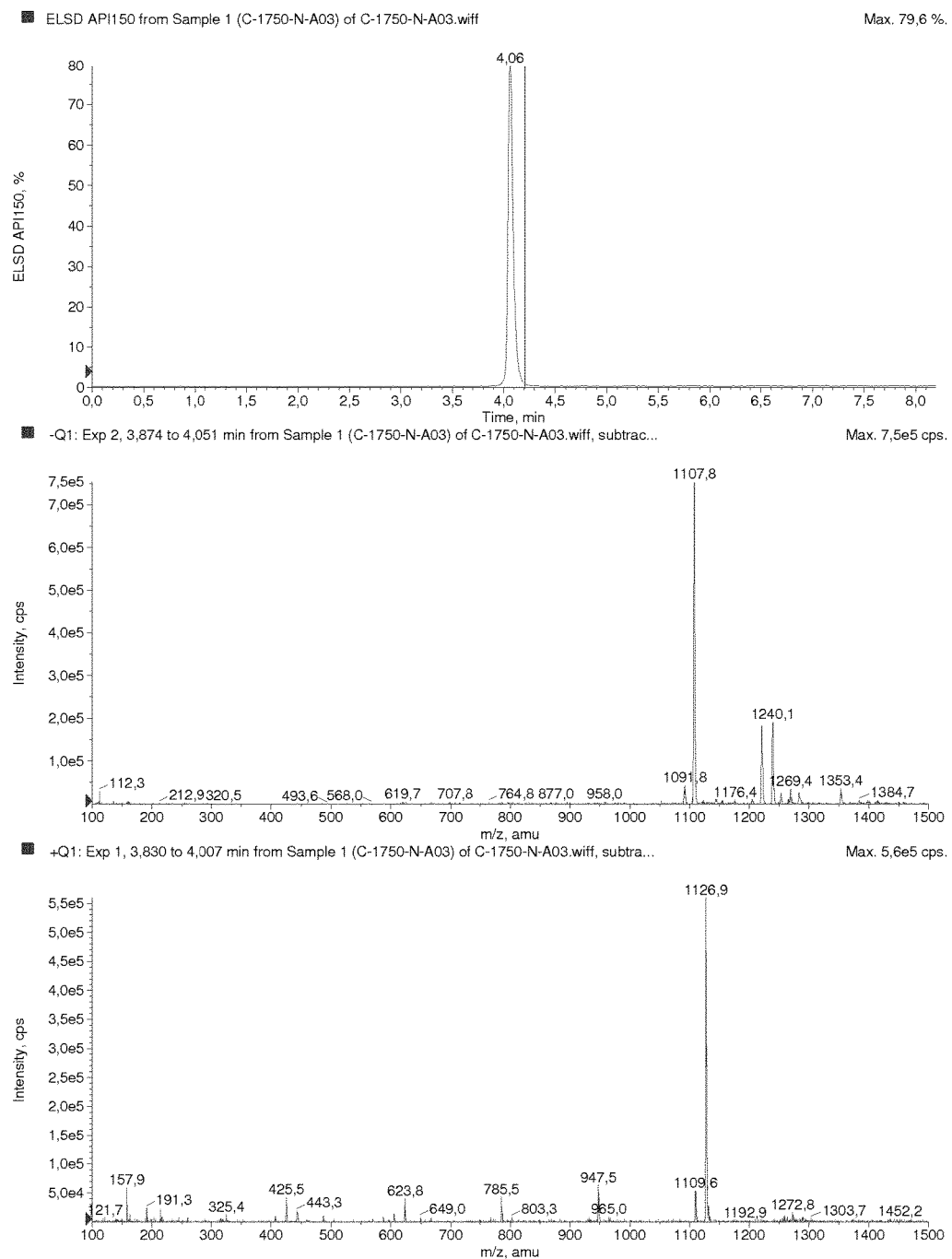

Figure 18: ESI-MS of compound Ff
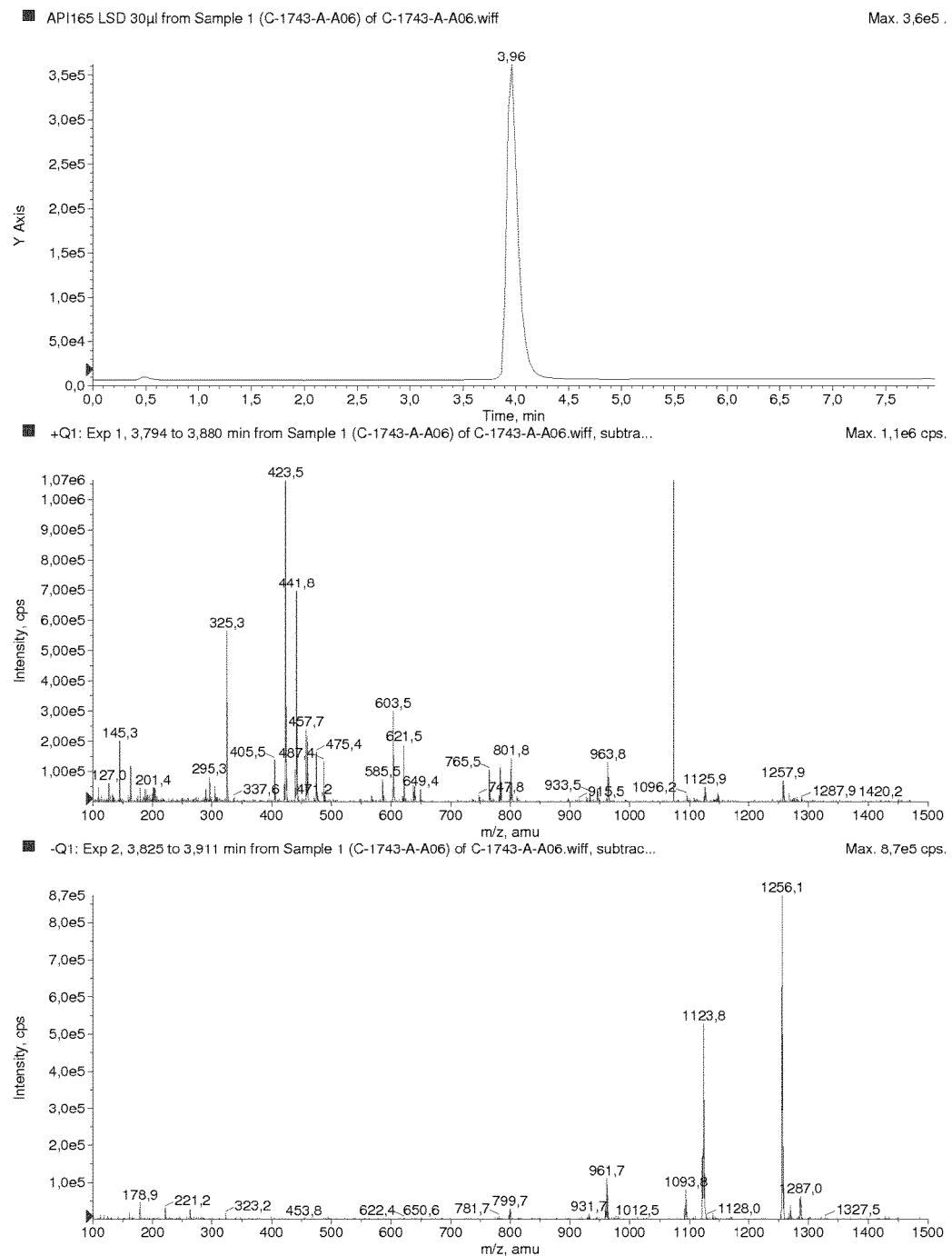

Figure 19: ESI-MS of compound Gg
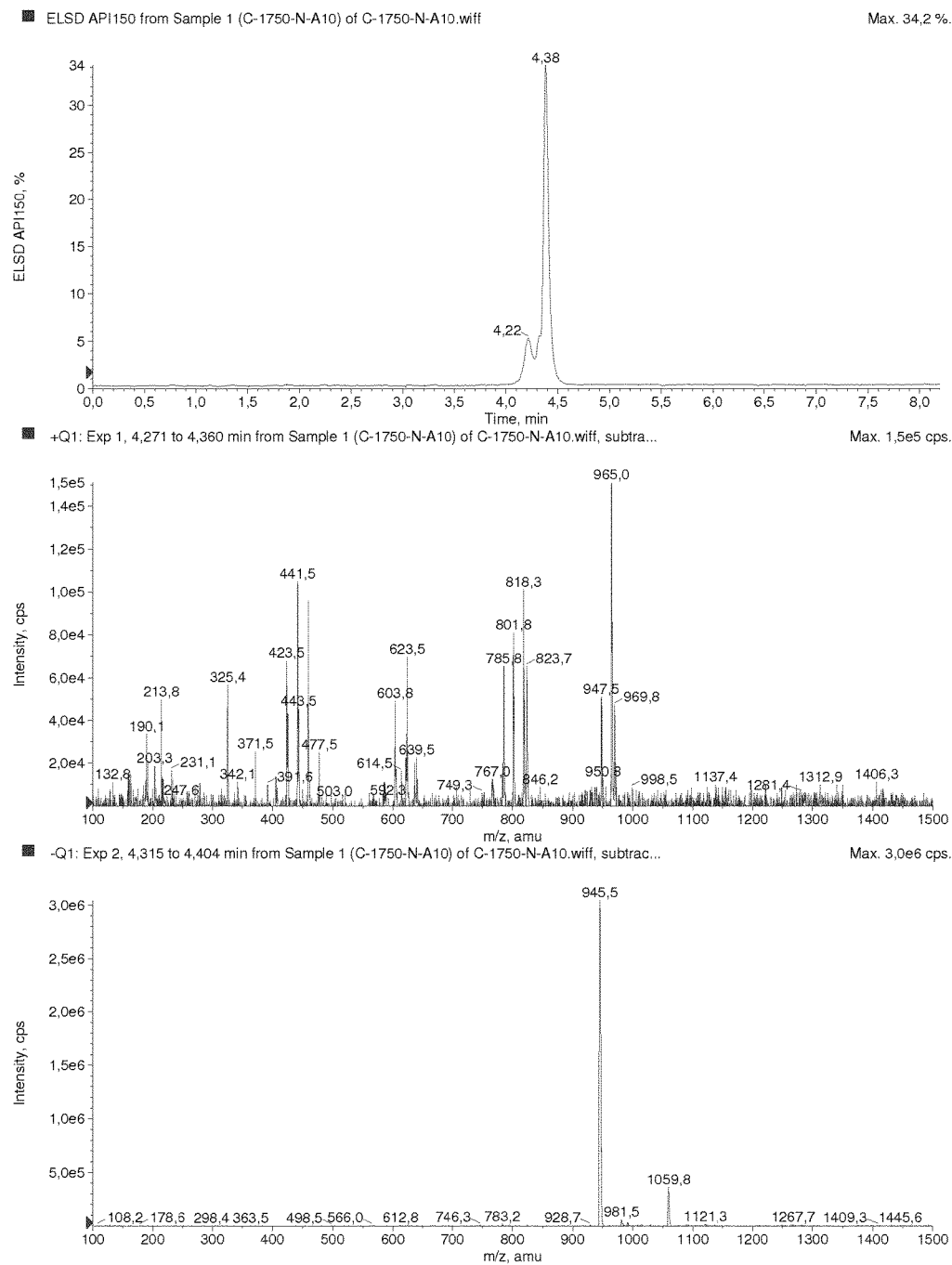

Figure 20: ESI-MS of compound Hh
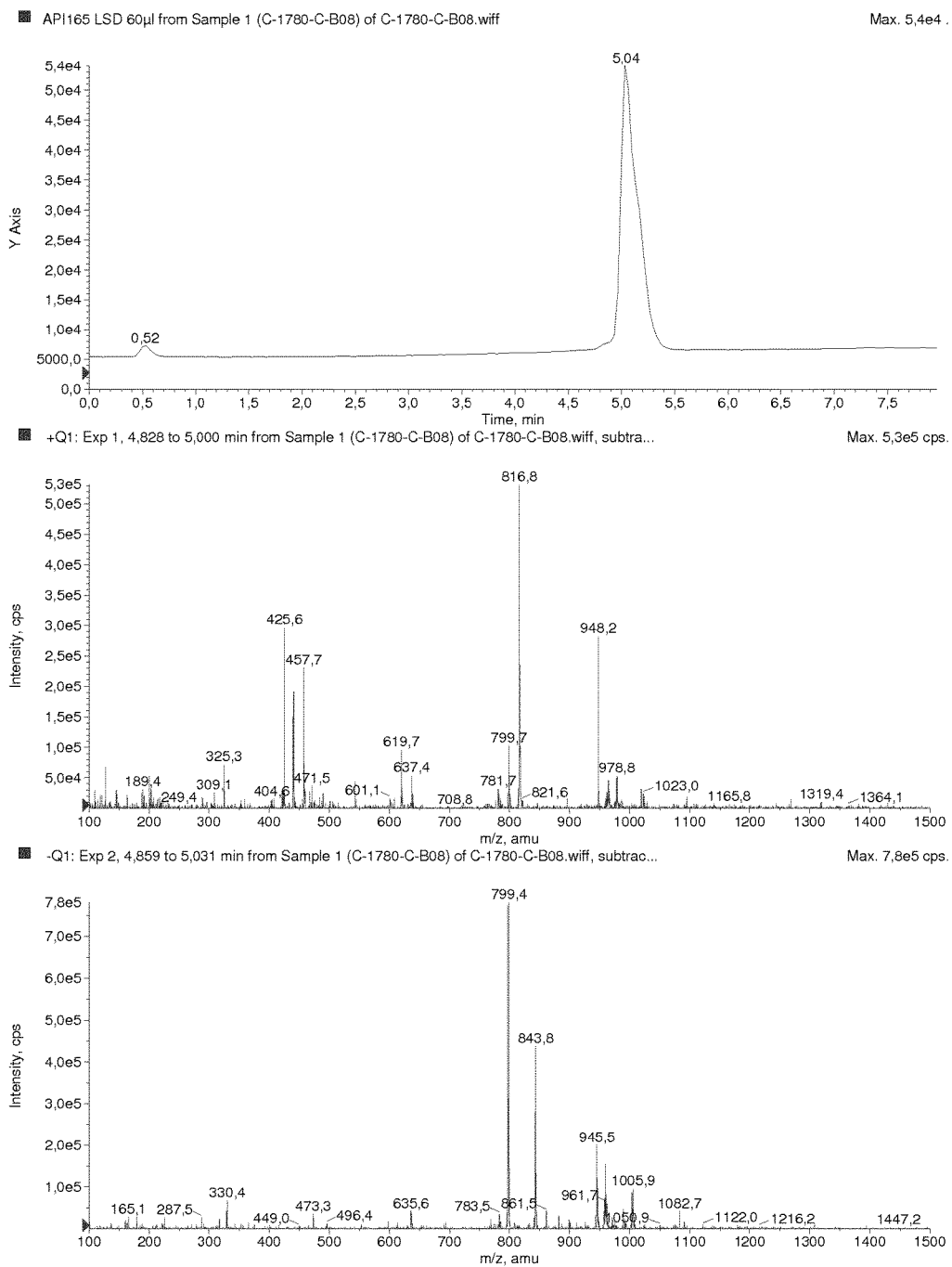

Figure 21: ESI-MS of compound Jj
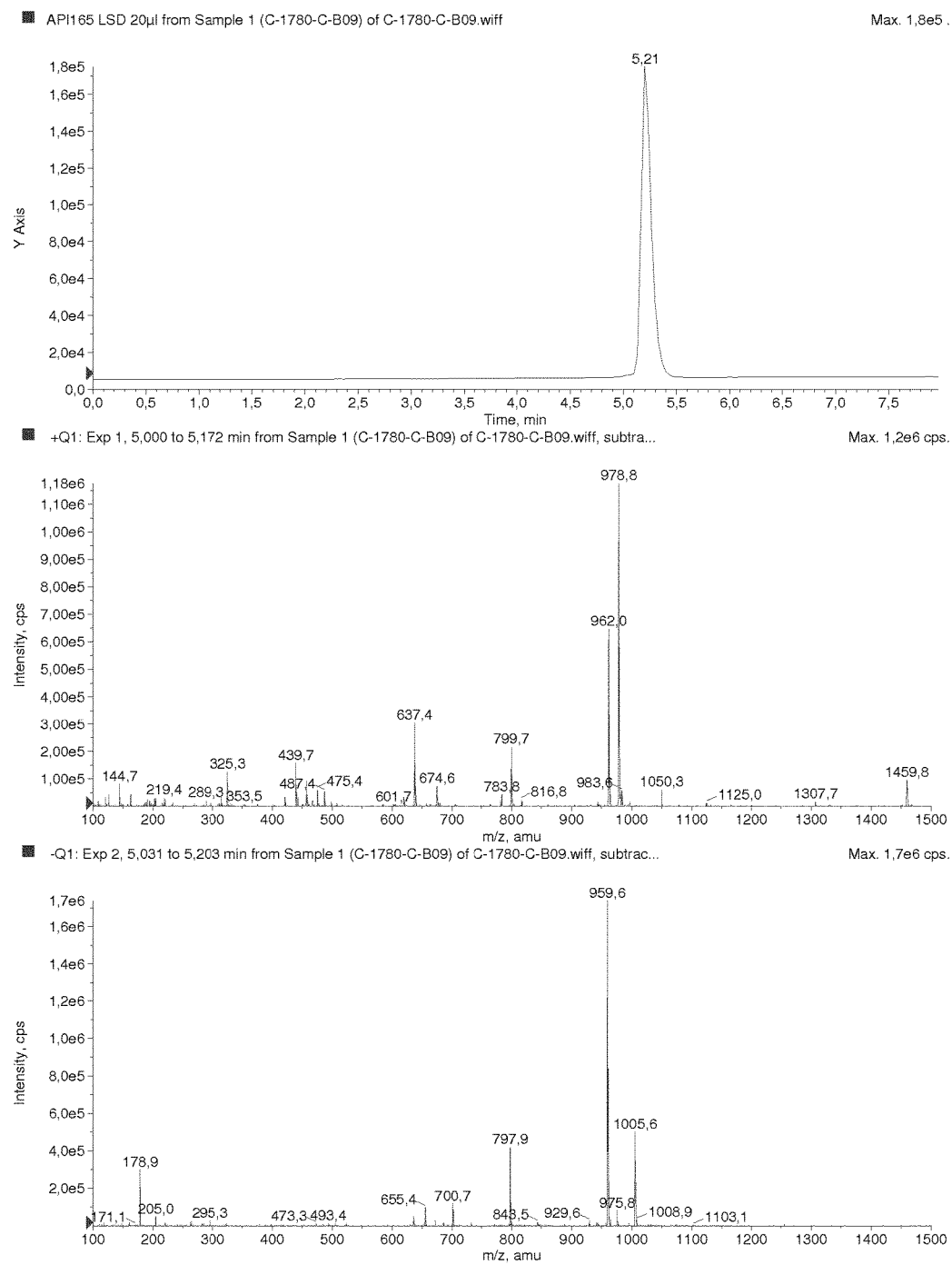

Figure 22: ESI-MS of compound Kk
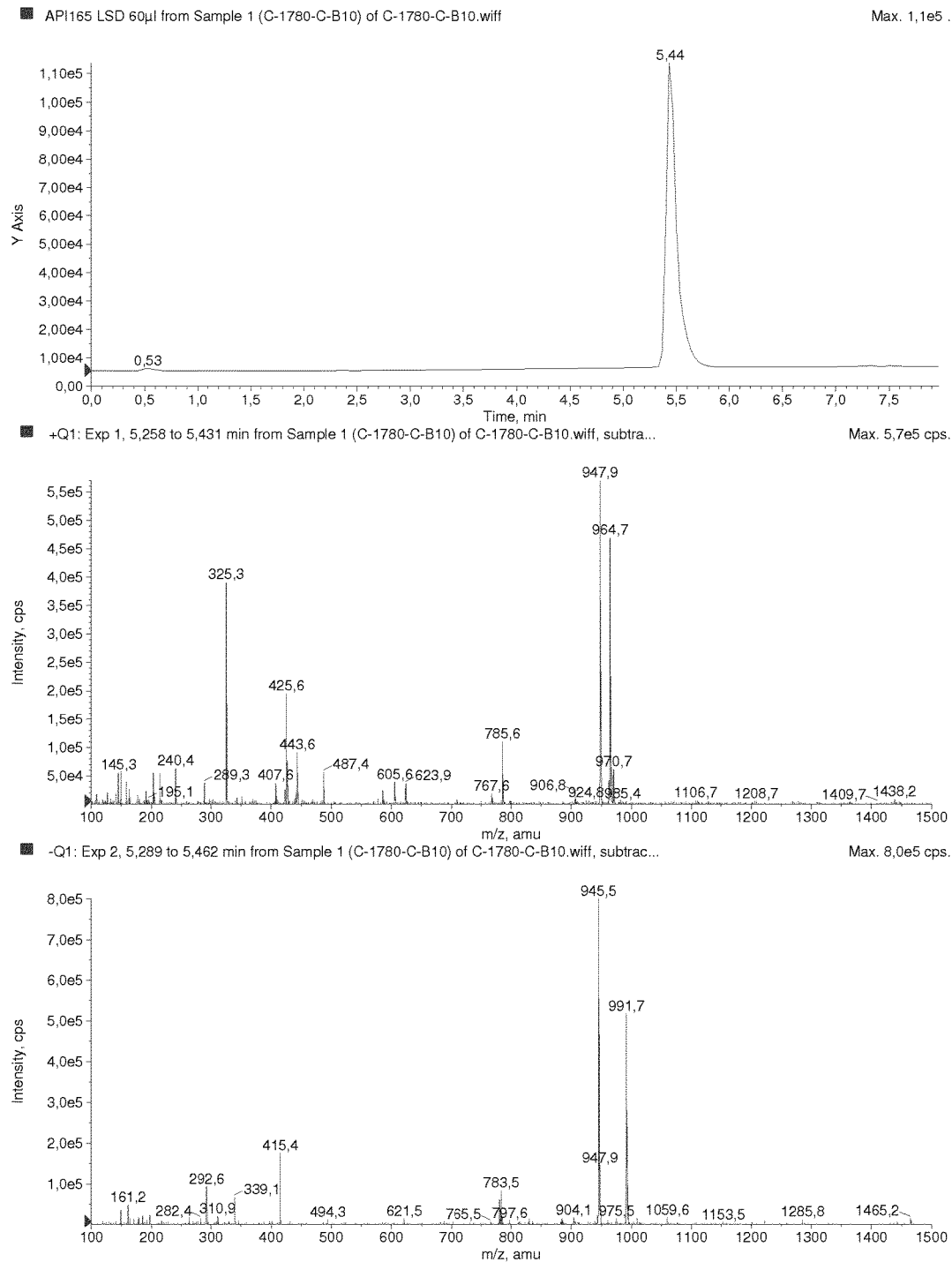

Figure 23: ESI-MS of compound LI
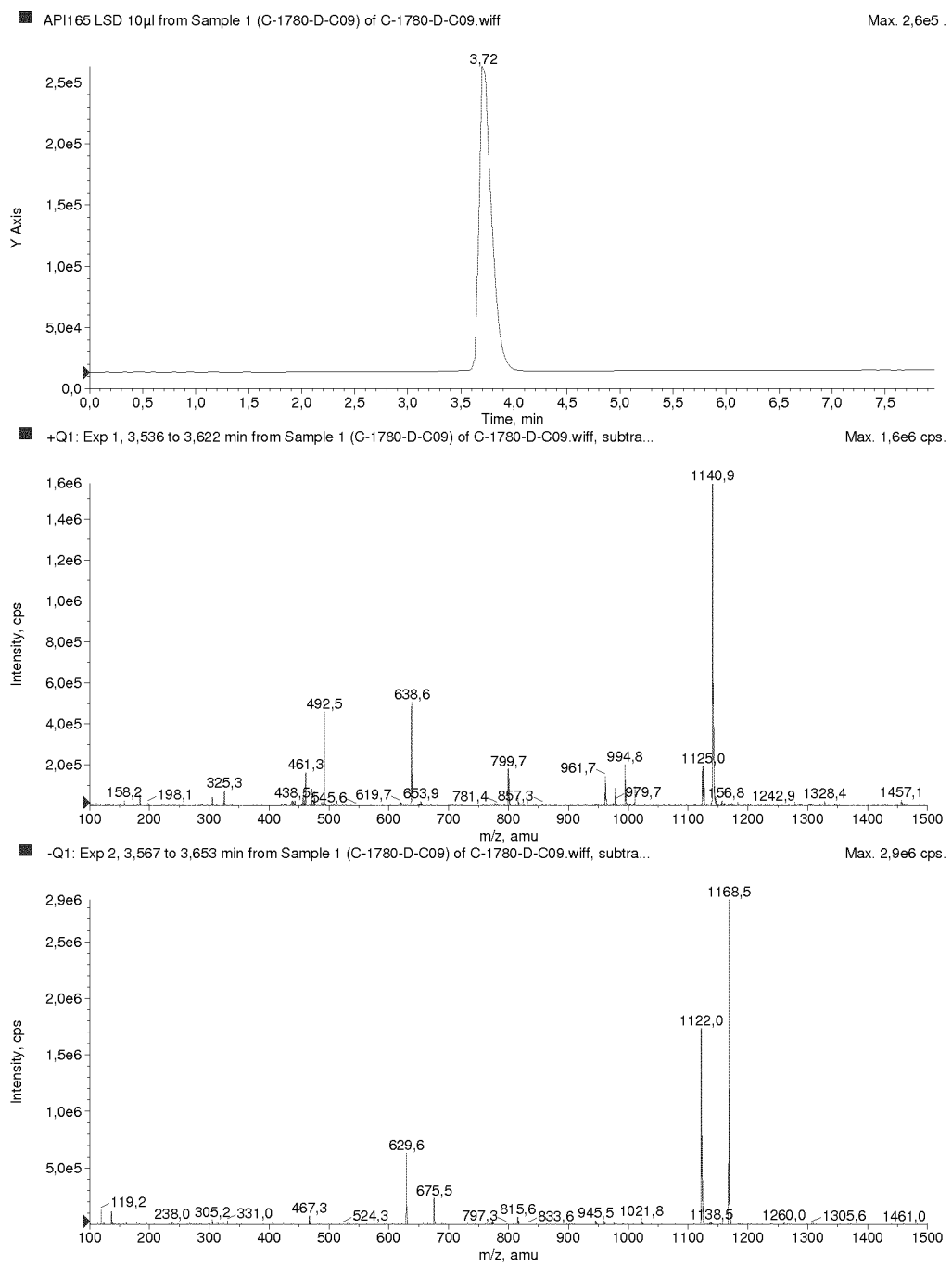

Figure 24: ESI-MS of compound Mm
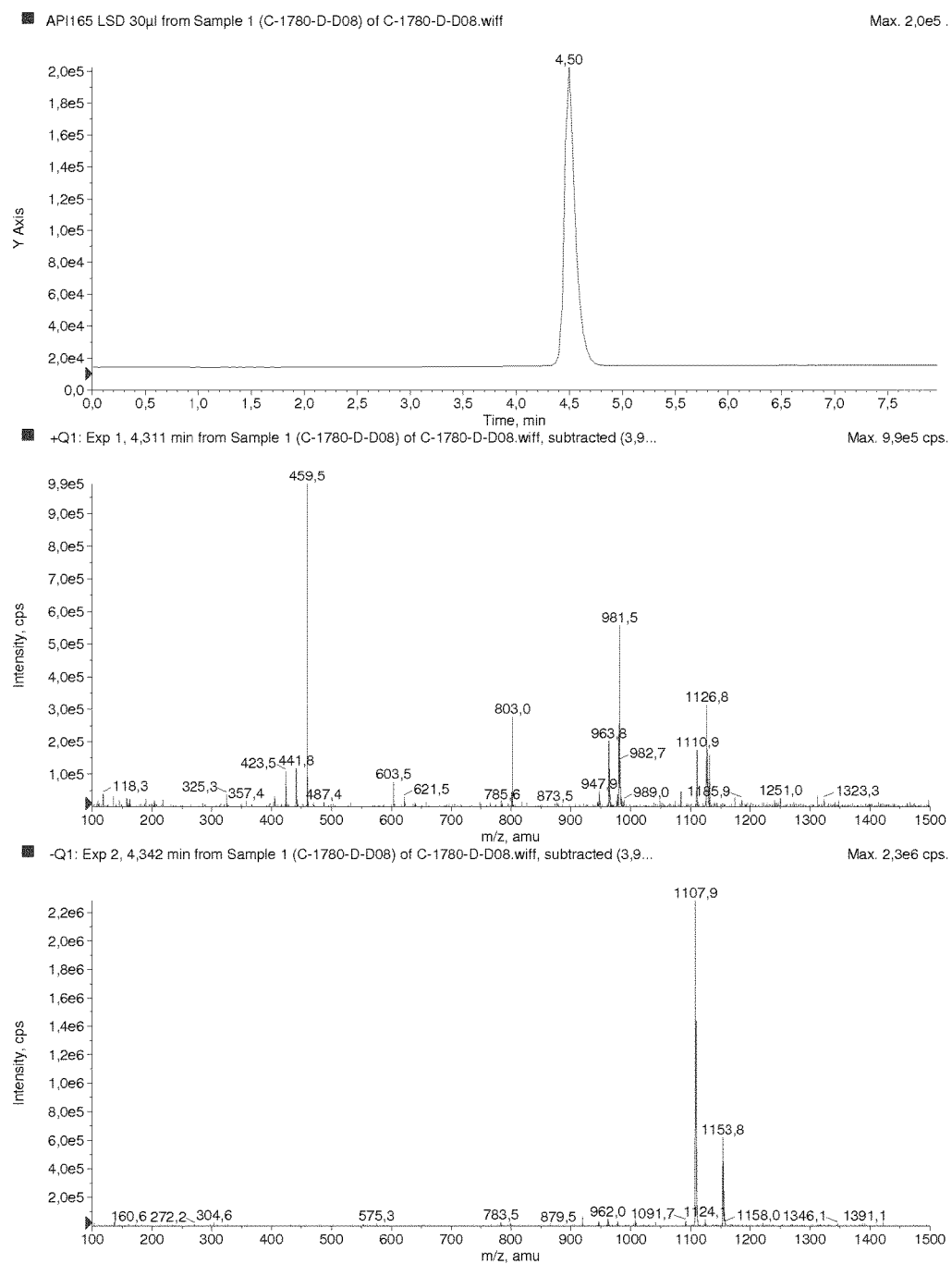

TRITERPENE-GLYCOSIDES AS SWEETENERS OR SWEETENER ENHANCERS

FIELD OF INVENTION

The invention relates to novel triterpene-glycoside compounds, which are obtainable by the extraction of *Momordica grosvenorii* (*Siraitia grosvenori*) and its physiologically acceptable salts which are useful as a sweetener or sweetener enhancer in preparations and compositions, especially oral edible compositions.

STATE OF THE ART

Sweetness is one of the primary taste and cravings of both animals and humans. The universal use of naturally occurring and synthetic sweeteners to satisfy this natural craving has not been met without its accompanying physiological disadvantages, e.g. obesity, nutritional imbalance and dental decay. To overcome these unwanted disadvantages considerable research efforts and expenditures have been made to develop alternative compounds, e.g. as substitute for the naturally occurring sweeteners or synthetic sweeteners which have no food value and are free of caloric input. While these artificial sweeteners enjoyed a wide use, and fulfilled the requirements of a sweet taste with no food value, and could be used without providing calories or damaging teeth, they were frequently found to possess inherent disadvantages that prevented their use for their intended purpose, e.g. because of their toxicity (p-ethoxyphenylurea) or chromosome damage and bladder trouble (sodium cyclamate). Thus, these sweeteners could not be safely recommended for use as a sweetener and are apparently unacceptable for consumption. Saccharin compounds are also commonly used as artificial sweeteners, since cyclamates have been come under governmental restrictions. Although saccharin compounds possess sweetness characteristics, they are undesirable as the sole sweetening agent in most food and beverage compositions because of the lingering bitter aftertaste perceived by most users. While saccharin and the cyclamates have been in common use as artificial sweetening agents for a number of years, there has been more recently discovered a series of new artificial sweeteners.

For example, Horowitz and Gentili, U.S. Pat. No. 3,087,821, teach the use of various dihydrochalcones having sugar substituents (dihydrochalcones glycosides) as sweetening agents. All sweet dihydrochalkones have a licorice like aftertaste and linger in the mouth for some time.

*Siraitia grosvenori* (Luo han guo), a member of the Cucurbitaceae family, is a plant native to some regions of southern Asia and China. The sweet taste of fruits of luo han guo mainly comes from triterpene glycosides generally known as mogrosides. There are a number of mogrosides identified in luo han guo but generally mogroside V (CAS No: 88901-36-4) has the highest concentration compared to others (Table 1). Mogrol glycosides have the same core moleculemogrol or oxo-mogrol and differ from each other by number and type of glycosidic residues bonded to mogrol or oxo-mogrol molecules (US 2012/0059071, Kasai et al. Agric. Biol. Chem. (1989), 3347-3349), Matsumoto et. al. Chem. Pharm. Bu. (1990) 2030-2032. Several mogrosides taste very sweet, often >100× sweeter than sucrose, including the major triterpen glycoside of *Siraitia grosvenori*, mogroside V. and its isomer iso-mogroside V (US2011/0027413), but all of them have a certain bitter aftertaste.

Major mogrosides present in Luo han guo fruits are compiled in the following Table A.

TABLE A

| Mogrosides | | |
|---|---|---|
| Substance | Mol. Formula | Mol. Weight |
| Mogroside IIE | $C_{42}H_{72}O_{14}$ | 801.01 |
| Mogroside III | $C_{48}H_{82}O_{19}$ | 963.15 |
| Mogroside IV | $C_{54}H_{92}O_{24}$ | 1125.29 |
| Mogroside V | $C_{60}H_{102}O_{29}$ | 1287.43 |
| Mogroside VI | $C_{66}H_{112}O_{34}$ | 1449.58 |
| 11-oxo-Mogroside V | $C_{66}H_{100}O_{29}$ | 1285.42 |
| Siamenoside I | $C_{54}H_{92}O_{22}$ | 1125.29 |

Leaves of *Stevia rebaudiana* are well known for its sweet taste due to its content of sweet diterpene glycosides. One of the major sweet compounds from *stevia*, Rebaudioside A, is approved as natural sweetener in US (since 2008) und EU (since 2011). Apart from its sweet taste, all sweeteners from *stevia* have a slower onset and longer duration than that of sugar, and a bitter or licorice-like aftertaste at high concentrations (Lemus-Mondaca et al. Food Chemistry 132 (2012) 1121-1132).

Another example is Symrise AG, EP 2529633 A1, which relates to triterpenes and triterpene glycosides and/or physiologically acceptable salts thereof. The triterpenes are, preferably naturally occurring triterpenes and triterpene glycosides from *Mycetia balansae*, for generating a sweet impression in an orally consumable formulation or for reinforcing the sweet impression of an orally consumable formulation. These triterpene-glycosides differ in structure from the triterpenes claimed in the present invention.

Accordingly, it is a primary object of the present invention to provide novel sweetener compounds and its physiologically acceptable salts, which have a positive sweet benefit in food and oral compositions. In particular, the object was to provide sweetener compounds which are capable to provide sweetness to consumable compositions in a way, that the balance between the degree of sweetness and the amount which has to be administered to obtain a sweet effect is comparable low, to overcome the aforesaid disadvantages associated with the prior art sweetener. It is another object of the present invention to provide sweetener compounds without astringent or bitter-taste aftertaste. The sweetener compounds to be specified should be toxicologically safe, effective already at relatively low concentrations, well tolerated by the digestion, stable (in particular in normal cosmetic and/or pharmaceutical formulations), and easy to formulate and economical to produce.

In the course of extensive studies on sweeteners, the present inventors succeeded in the isolation of novel sweetener compounds of formula (I) and found that these sweetener compounds of formula (I) show astonishingly good and strong sweetness when compared with that of sucrose and mogroside V. Surprisingly, it has been further observed that the sweetener compounds of formula (I) have significantly less negative aftertaste at all and have high sweetening power.

DESCRIPTION OF THE INVENTION

The subject of the invention relates to a sweetener compound of formula (I)

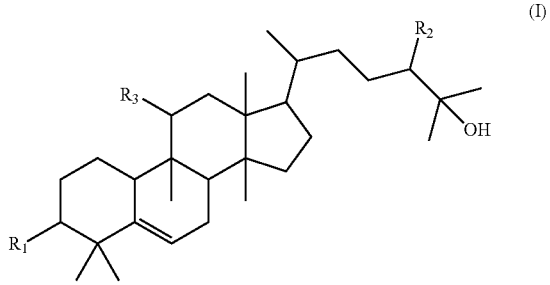

(I)

wherein $R_1$, $R_2$, $R_3$ are independently of one another and denote hydrogen, hydroxyl, carbonyl or a sugar moiety selected from the group consisting of a monosaccharide and/or oligosaccharide.

Preferably in the sweetener compound of formula (I) the monosaccharide and/or the monosaccharide units of the oligosaccharide are selected from the group consisting of fructose, glucose, sucrose, xylose, maltose, mannose, rhamnose, galactose, lactose, gentiobiose, sophorose, β-Glucopyranosyl-(1-2)-[β-Glucopyranosyl-(1-6)]-β-glucopyranose, cellobiose, mannitol, sorbitol, xylitol or arabitol, glucuronic acid, quinovose, arabinopyranose, arabinofuranose, xylopyranose, xylofuranose and/or a piose (2,3,4-trihydroxy-3-(hydroxymethyl)butanal), and
wherein the oligosaccharide consists of 2 to 5 monosaccharide units.

The term "monosaccharide" means the simplest form of sugar. Monosaccharides are the most basic units of biologically important carbohydrates. Examples of monosaccharides include glucose (dextrose), fructose (levulose), galactose, xylose and ribose. Monosaccharides are the building blocks of disaccharides (such as sucrose) and polysaccharides (such as cellulose and starch). Further, each carbon atom that supports a hydroxyl group (except for the first and last) is chiral, giving rise to a number of isomeric forms all with the same chemical formula. For instance, galactose and glucose are both aldohexoses, but have different chemical and physical properties.

The term "oligosaccharide" represents a kind of a saccharide polymer containing a small number of 2 to 10, preferably 2 to 5 of sugar units (monosaccharide units) which are linked together. The monosaccharides of the oligosaccharides are usually linked with each other through a glycosidic bond.

The term "sugar moiety" is equal to the term sugar moiety component or unit.

The sugar moiety of the present invention may be in its simplest form, preferably, represented by the unit formula (II):

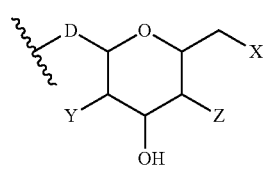

(II)

wherein D is O, S or N
X, Y and Z are independently of one another and denote hydrogen, hydroxyl, carbonyl or another sugar moiety, which is another unit represented by formula (II). The sugar moiety is preferably linked to formula (I) through an oxygen or a nitrogen or a sulphur atom, more preferably an oxygen atom, which is represented in formula (II) by the integer D. In the preferred embodiments of the present invention, in case that $R_1$, $R_2$, $R_3$ are independently sugar moieties, the compounds are linked to each other, preferably, through an oxygen atom.

The three-dimensional structure of a monosaccharide can be represented in four different forms: a) The Fischer projection is a systematic way of drawing the skeletal formula of an acyclic monosaccharide so that the handedness of each chiral carbon is well specified. Each stereoisomer of a simple open-chain monosaccharide can be identified by the positions (right or left) in the Fischer diagram of the chiral hydroxyls (the hydroxyls attached to the chiral carbons). b) Haworth projection: In this diagram, the α-isomer has the —OH of the anomeric carbon below the plane of the carbon atoms, and the β-isomer has the —OH of the anomeric carbon above the plane. Pyranoses typically adopt a chair conformation, similar to cyclohexane. In this conformation, the α-isomer has the —OH of the anomeric carbon in an axial position, whereas the β-isomer has the OH— of the anomeric carbon in equatorial position. c) A more realistic illustration is the chair form, which show the angulated formation of the carbon chains and d) at least the absolute stereo-chemical illustration of the, e.g. cyclohexane conformation is also common:

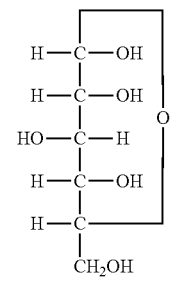

1

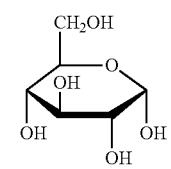

2

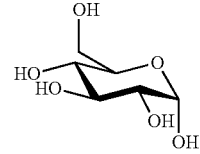

3

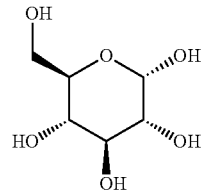

4

Different illustrations of alpha-D-Glucopyranose: Tollens (1); Haworth (2); chair (3); absolute stereo (Source: Wikepedia: http://de.wikipedia.org/wiki/Monosaccharide)

As to formula (II), the sugar unit is illustrated as a planar moiety, and means that the sugar unit in the present invention may possess all possible stereo-isomeric forms, and is not restricted to a certain isomeric form in first line.

BRIEF DESCRIPTION OF THE DRAWINGS

The present invention will be described in greater detail with reference to the accompanying drawings, in which FIG. 1 is a graph of the H-NMR of the compound Aa according to the present invention, FIG. 2 is a graph of the H-NMR of the compound Bb according to the present invention, FIG. 3 is a graph of the H-NMR of the compound Cc according to the present invention, FIG. 4 is a graph of the H-NMR of the compound Dd according to the present invention, FIG. 5 is a graph of the H-NMR of the compound Ee according to the present invention, FIG. 6 is a graph of the H-NMR of the compound Ff according to the present invention, FIG. 7 is a graph of the H-NMR of the compound Gg according to the present invention, FIG. 8 is a graph of the H-NMR of the compound Hh according to the present invention, FIG. 9 is a graph of the H-NMR of the compound Jj according to the present invention, FIG. 10 is a graph of the H-NMR of the compound Kk according to the present invention, FIG. 11 is a graph of the H-NMR of the compound Ll according to the present invention, FIG. 12 is a graph of the H-NMR of the compound Mm according to the present invention, FIG. 13 are graphs of the ESI-MS of the compound Aa according to the present invention, FIG. 14 are graphs of the ESI-MS of the compound Bb according to the present invention, FIG. 15 are graphs of the ESI-MS of the compound Cc according to the present invention, FIG. 16 are graphs of the ESI-MS of the compound Dd according to the present invention, FIG. 17 are graphs of the ESI-MS of the compound Ee according to the present invention, FIG. 18 are graphs of the ESI-MS of the compound Ff according to the present invention, FIG. 19 are graphs of the ESI-MS of the compound Gg according to the present invention, FIG. 20 are graphs of the ESI-MS of the compound Hh according to the present invention, FIG. 21 are graphs of the ESI-MS of the compound Jj according to the present invention, FIG. 22 are graphs of the ESI-MS of the compound Kk according to the present invention, FIG. 23 are graphs of the ESI-MS of the compound Ll according to the present invention, and FIG. 24 are graphs of the ESI-MS of the compound Mm according to the present invention.

PREFERRED EMBODIMENTS OF THE INVENTION (1) In a preferred embodiment, a compound of formula (I) possess a sugar unit of formula (II) at least one times (monosaccharide). In a preferred embodiment the sugar unit of formula (II) is a repeated sugar unit, which is repeated two, three, four or five times which are linked together through the oxygen atom of the carbohydrate.

(2) In a preferred embodiment the sugar unit of formula (II) is only one time represented in formula (I), which is either $R_1$, $R_2$ or $R_3$.

(3) In a preferred embodiment of the invention $R_1$, $R_2$ of formula (I) are independently of one another and denote hydrogen, hydroxyl, carbonyl or a sugar moiety selected from the group consisting of a monosaccharide and/or oligosaccharide and $R_3$ of formula (I) denote hydrogen, hydroxyl or carbonyl. The preferred monosaccharide and/ or the monosaccharide units of the oligosaccharide are selected from the group consisting of fructose, glucose, sucrose, xylose, maltose, mannose, rhamnose, galactose, lactose, gentiobiose, sophorose, β-Glucopyranosyl-(1-2)-[β-Glucopyranosyl-(1-6)]-β glucopyranose, cellobiose, mannitol, sorbitol, xylitol or arabitol, glucuronic acid, quinovose, arabinopyranose, arabinofuranose, xylopyranose, xylofuranose and/or apiose (2,3,4-trihydroxy-3-(hydroxymethyl)butanal). Glucose, maltose, galactose, arabinopyranose and xylopyranose are preferred, and glucose, galactose, arabinopyranose and xylopyranose are most preferred as sugar moiety.

(4) In a preferred embodiment of the invention $R_1$, $R_2$ of formula (I) are independently of one another and denote hydrogen, hydroxyl, carbonyl or a sugar moiety selected from the group consisting of a monosaccharide and/or oligosaccharide which is selected from the group consisting of fructose, glucose, sucrose, xylose, maltose, mannose, rhamnose, galactose, lactose, cellobiose, gentiobiose, sophorose, β-Glucopyranosyl-(1-2)-[β-Glucopyranosyl-(1-6)]-β-glucopyranose, mannitol, sorbitol, xylitol or arabitol, glucuronic acid, quinovose, arabinofuranose, xylopyranose, xylofuranose and/or apiose (2,3,4-trihydroxy-3-(hydroxymethyl)butanal), and $R_3$ of formula (I) denote hydrogen, hydroxyl or carbonyl.

(5) Preferred component for the sugar moiety are fructose, glucose, sucrose, maltose, galactose, arabinopyranose and xylopyranose, and glucose, arabinopyranose and xylopyranose are most preferred as sugar moiety.

(6) In another preferred embodiment $R_1$ and $R_2$ are independently of one another and denote a monosaccharide, which are preferably a glucose and/or arabinopyranose and/or xylopyranose.

(7) In another preferred embodiment $R_1$ and $R_2$ are independently of one another and denote an oligosaccharide, in which the monosaccharide units are preferably a glucose and/or galactose and/or arabinopyranose and/or xylopyranose. Preferably, the oligosaccharide contains one, two, three or four units of glucose and/or galactose and/or arabinopyranose and/or xylopyranose. More preferably, the oligosaccharide contains one, two or three units of glucose.

(8) In another preferred embodiment $R_3$ is hydrogen and $R_1$, $R_2$ of formula (I) are independently of one another and denote hydrogen, hydroxyl, carbonyl or a sugar moiety selected from the group consisting of a monosaccharide and/or oligosaccharide which is selected from the group consisting of fructose, glucose, sucrose, xylose, maltose, mannose, rhamnose, galactose, lactose, cellobiose, mannitol, sorbitol, xylitol or arabitol, glucuronic acid, quinovose, arabinopyranose, arabinofuranose, xylopyranose, xylofuranose and/or apiose (2,3,4-trihydroxy-3-(hydroxymethyl)butanal).

(9) In another preferred embodiment $R_3$ is hydrogen and $R_1$, $R_2$ of formula (I) are independently of one another and denote a sugar moiety selected from the group consisting of a monosaccharide and/or oligosaccharide with monosaccharide units which are selected from the group consisting fructose, glucose, sucrose, xylose, maltose, mannose, rhamnose, galactose, lactose, gentiobiose, sophorose, β-Glucopyranosyl-(1-2)-[β-Glucopyranosyl-(1-6)]-β-glucopyranose, cellobiose, mannitol, sorbitol, xylitol or arabitol, glucuronic acid, quinovose, arabinopyranose, arabinofuranose, xylopyranose, xylofuranose and/or apiose (2,3,4-trihydroxy-3-(hydroxymethyl)butanal).

(10) In a preferred embodiment of the invention $R_1$ and $R_2$ of formula (I) are independently of one another and denote hydroxyl or a sugar moiety selected from a monosaccharide and/or oligosaccharide,
wherein the monosaccharide and/or the monosaccharide units of the oligosaccharide are selected from the group consisting of glucose, 2-glucopyranosyl-glucose, 3-glucopyranosyl-glucose, 4-glucopyranosyl-glucose, 6-glucopyranosyl-glucose, or glucopyranosyl-(1→2)-[glucopyranosyl-(1→6)]-glucose, and
whereby in case of the oligosaccharide, the monosaccharide units of the oligosaccharide are linked via glycosidic bonds to each other, and
$R_3$ denote hydrogen, hydroxyl or carbonyl.

(11) In a further preferred embodiment of the invention in case $R_2$ of compound of formula (I) is an oligosaccharide with 2 monosaccharide units (disaccharide), and wherein the monosaccharide units of the disaccharide of $R_2$ are linked via glycosidic bonds together, which is not a 1→6 linking.

(12) Furthermore, in a preferred embodiment $R_2$ is an oligosaccharide with 2 monosaccharide units (disaccharide), and $R_3$ denote hydrogen or carbonyl.

(13) In another preferred embodiment of the invention $R_1$ denotes hydrogen, hydroxyl, carbonyl or an oligosaccharide with 2, 3, 4 or 5 monosaccharide units, and $R_2$ is an oligosaccharide with 2 monosaccharide units (disaccharide), and $R_3$ denotes hydroxyl.

(14) In a preferred embodiment of the invention wherein in case $R_2$ is an oligosaccharide with 3 monosaccharide units (trisaccharide), then
$R_1$ is carbonyl and/or
$R_3$ is not hydroxyl or carbonyl or
$R_3$ is hydroxyl and $R_1$ is an oligosaccharide with 2, 4 or 5 monosaccharide units, wherein the monosaccharide units of the oligosaccharide of $R_1$ are linked via glycosidic bonds together which is not a 1→6 or 1→4 linking.

(15) In a preferred embodiment of the invention $R_1$ is a monosaccharide or an oligosaccharide with at least 3 monosaccharide units, and
$R_2$ is an oligosaccharide with 3 monosaccharide units (trisaccharide), and
$R_3$ is carbonyl.

(16) In a preferred embodiment of the invention $R_1$ is an oligosaccharide with 2, 4 or 5 monosaccharide units, but not with 3 monosaccharide units.

(17) In a preferred embodiment of the invention $R_2$ is an oligosaccharide with 2 to 5 monosaccharide units, but not a (single) monosaccharide.

(18) In a preferred embodiment of the invention when $R_2$ is carbonyl, then
$R_3$ is not carbonyl or
$R_3$ is hydroxyl.

(19) In another preferred embodiment of the sweetener compound of formula (I), in case
$R_1$ denotes a sugar moiety with two sugar units, and
$R_2$ denotes a sugar moiety with three sugar units, then
$R_3$ denotes a hydrogen or carbonyl group, preferably a hydrogen and/or
the glycosidic bonds in the sugar units in $R_1$ differ from that in mogroside V and iso-mogroside V with disaccharide moieties linked via 1→4 or 1→6 glycosidic bond, and not 1→2 glycosidic bond.

(20) In another preferred embodiment of the sweetener compound of formula (I), in case
$R_1$ denotes a sugar moiety with two sugar units, and
$R_2$ denotes a sugar moiety with three sugar units, and
$R_3$ denotes hydrogen.

Compounds of Particular Interest

Of particular interest are the compounds of Formula (I) identified as:

Compound A 3,11-dihydroxy-4,4,9,13,14-pentamethyl-2,3,4,7,8,9,10,11,12,13,14,15,16,17-tetradecahydro-1H-cyclopenta[a]phenanthren-17-yl)-2-hydroxy-2-methylheptan-3-yloxy)-4,5-dihydroxy-6-(hydroxymethyl)tetrahydro-2H-pyran-3-yloxy)-6-(hydroxymethyl)tetrahydro-2H-pyran-3,4,5-triol

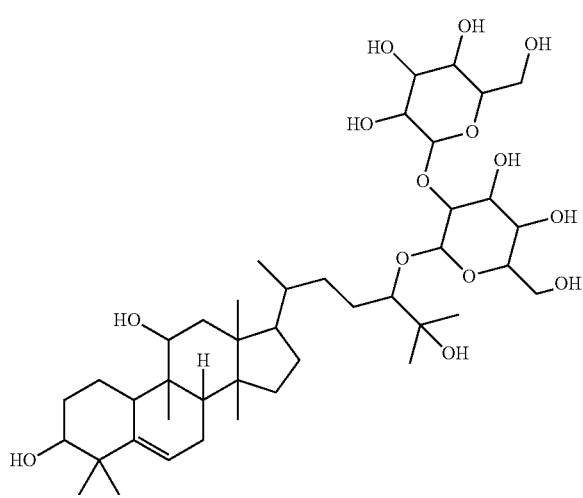

(Compound A)

Compound B 4,5-dihydroxy-2-(2-hydroxy-2-methyl-6-((4,4,9,13,14-pentamethyl-3-(3,4,5-trihydroxy-6-((3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-((3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol

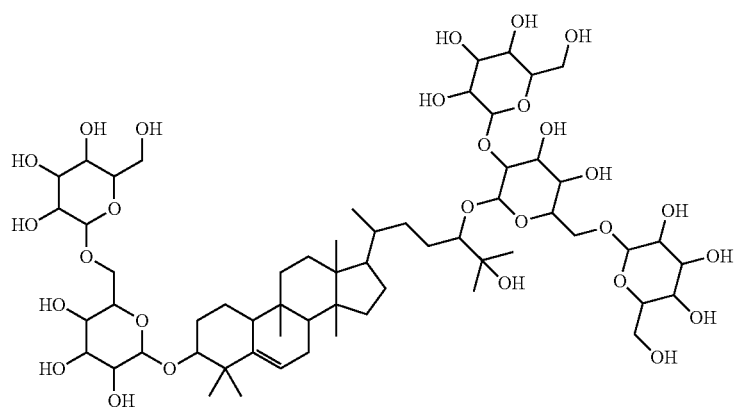
(Compound B)

Compound C 4,5-dihydroxy-3-(3,4,5-trihydroxy-6-(hydroxymethyl)tetrahydro-2H-pyran-2-yloxy)-6-((3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-2-(hydroxymethyl)tetrahydro-2H-pyran-3-yloxy)-6-(hydroxymethyl)tetrahydro-2H-pyran-3,4,5-triol

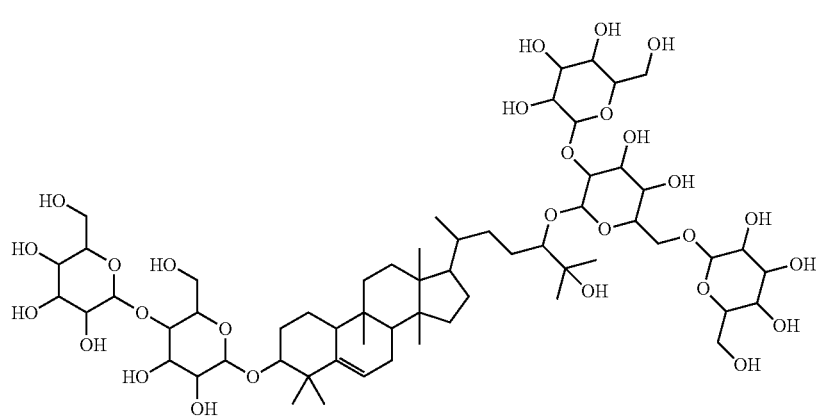
(Compound C)

Compound D 2-(2-(17-(5-(4,5-dihydroxy-3-(3,4,5-trihydroxy-6-(hydroxymethyl)tetrahydro-2H-pyran-2-yloxy)-6-((3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-6-(hydroxymethyl)tetrahydro-2H-pyran-3-yloxy)-6-(hydroxymethyl)tetrahydro-2H-pyran-3,4,5-triol

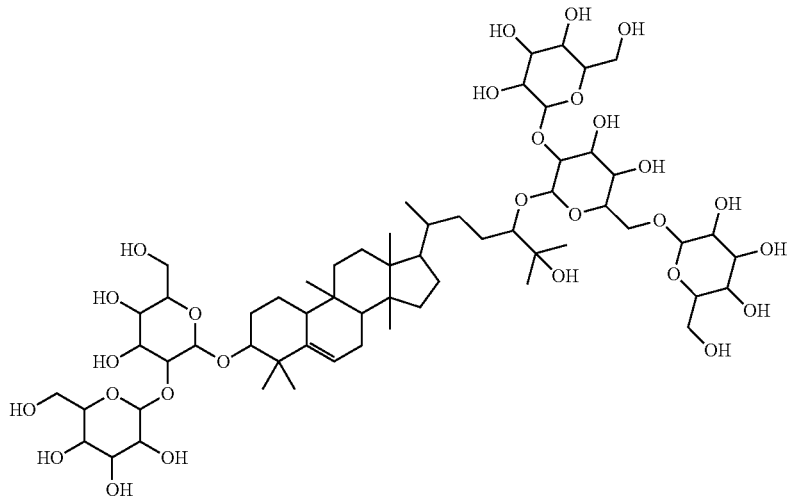

(Compound D)

Compound E 2-(4,5-dihydroxy-2-(2-hydroxy-2-methyl-6-(4,4,9,13,14-pentamethyl-3-(3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-((3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol

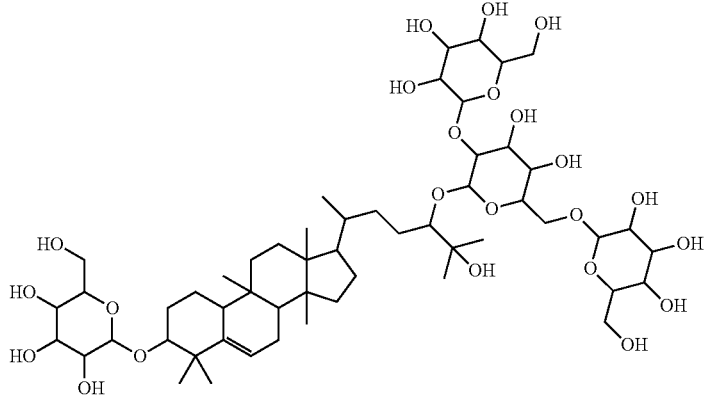

(Compound E)

Compound F 2-((6-(6-(3-(4,5-dihydroxy-6-(hydroxymethyl)-3-(3,4,5-trihydroxytetrahydro-2H-pyran-2-yloxy)tetrahydro-2H-pyran-2-yloxy)-11-hydroxy-4,4,9,13,14-pentamethyl-2,3,4,7,8,9,10,11,12,13,14,15,16,17-tetradecahydro-1H-cyclopenta[a]phenanthren-17-yl)-2-hydroxy-2-methylheptan-3-yloxy)-3,4-dihydroxy-5-(3,4,5-trihydroxy-6-(hydroxymethyl)tetrahydro-2H-pyran-2-yloxy)tetrahydro-2H-pyran-2-yl)methoxy)-6-(hydroxymethyl)tetrahydro-2H-pyran-3,4,5-triol

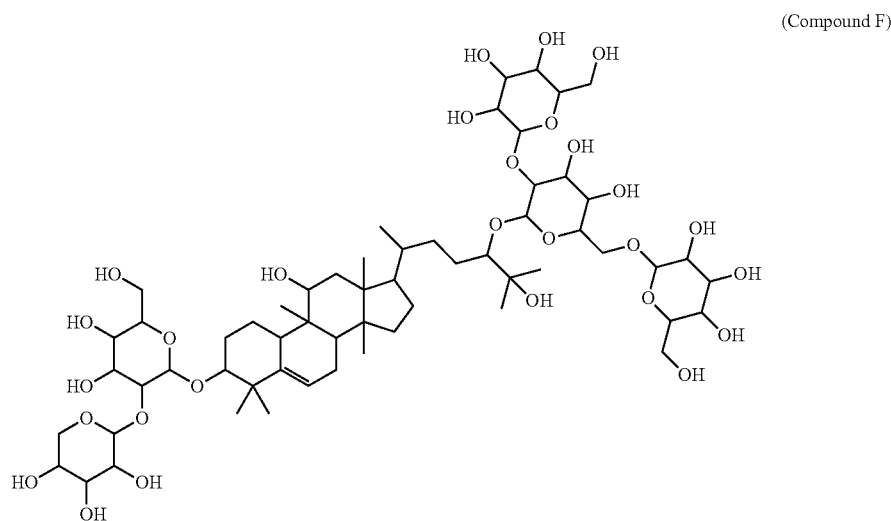 [SMILES: CC(CCC(OC1OC(COC2OC(CO)C(O)C(O)C2O)C(O)C(O)C1OC1OC(CO)C(O)C(O)C1O)C(C)(C)O)C1CCC2(C)C3CC=C4C(CCC(OC5OC(CO)C(O)C(O)C5OC5OCC(O)C(O)C5O)C4(C)C)C3(C)C(O)CC12C]

(Compound F)

Compound G 2-(4,5-dihydroxy-2-(3-hydroxy-2-methyl-6-(4,4,9,13,14-pentamethyl-3-(3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-2-yloxy)-6-(hydroxymethyl)tetrahydro-2H-pyran-3-yloxy)-6-(hydroxymethyl)tetrahydro-2H-pyran-3,4,5-triol

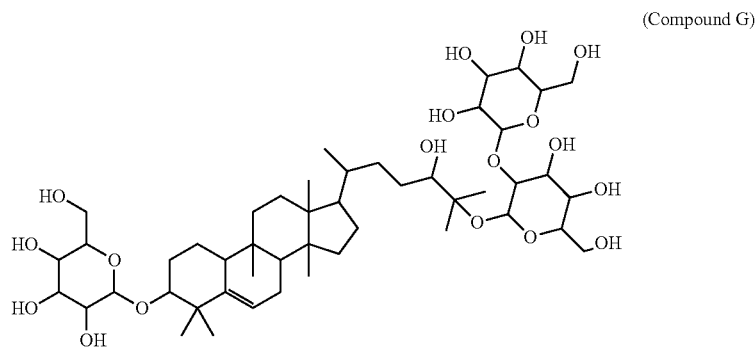

(Compound G)

Compound H 2-hydroxy-6-(11-hydroxy-4,4,9,13,14-pentamethyl-3-(3,4,5-trihydroxy-6-((3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)-2-methylheptan-3-one

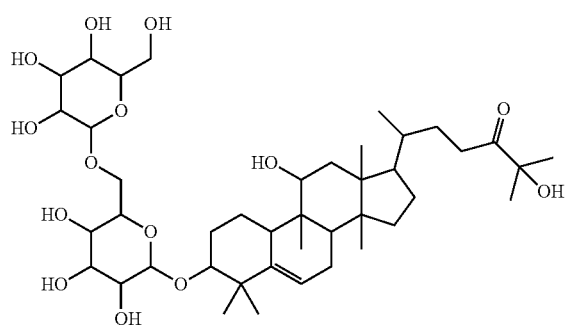

(Compound H)

Compound J 17-(5-(4,5-dihydroxy-3-(3,4,5-trihydroxy-6-(hydroxymethyl)tetrahydro-2H-pyran-2-yloxy)-6-((3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-11-hydroxy-4,4,9,13,14-pentamethyl-4,7,8,9,10,11,12,13,14,15,16,17-dodecahydro-1H-cyclopenta[a]phenanthren-3(2H)-one

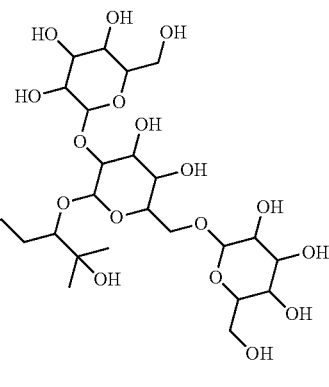

(Compound J)

Compound K 2-(4,5-dihydroxy-2-(2-hydroxy-6-(3-hydroxy-4,4,9,13,14-pentamethyl-2,3,4,7,8,9,10,11,12,13,14,15,16,17-tetradecahydro-1H-cyclopenta[a]phenanthren-17-yl)-2-methylheptan-3-yloxy)-6-((3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol

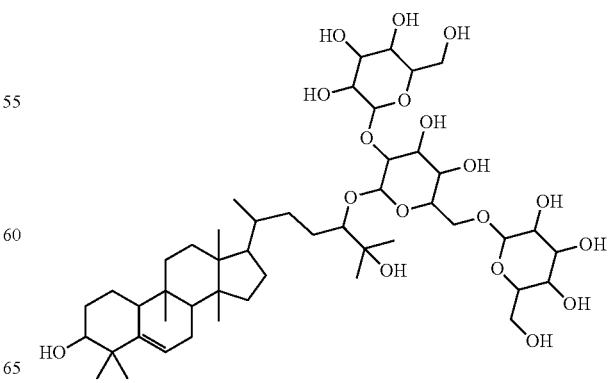

(Compound K)

Compound L 17-(5-(4,5-dihydroxy-3-(3,4,5-trihydroxy-6-(hydroxymethyl)tetrahydro-2H-pyran-2-yloxy)-6-((3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-3-(3,4,5-trihydroxy-6-(hydroxymethyl)tetrahydro-2H-pyran-2-yloxy)-3,4,7,8,9,10,12,13,14,15,16,17-dodecahydro-1H-cyclopenta[a]phenanthren-11(2H)-one

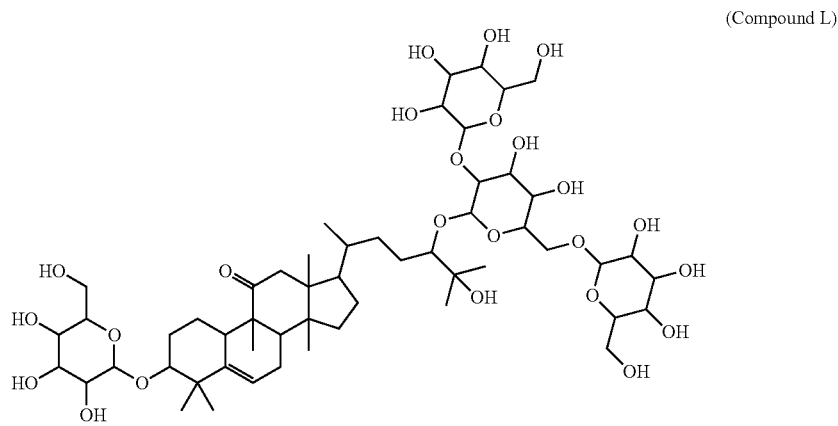

(Compound L)

Compound M 2-(4,5-dihydroxy-2-(2-hydroxy-2-methyl-6-(4,4,9,13,14-pentamethyl-3-(3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-((3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol

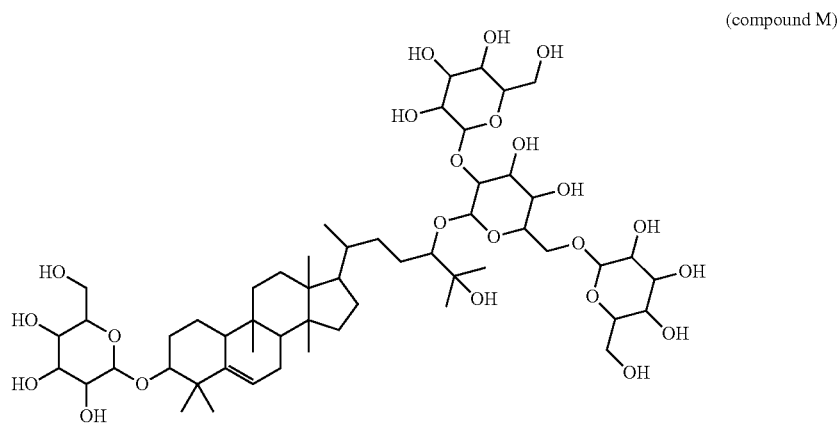

(compound M)

The compounds A to M are represented in planar forms, which is especially preferred. That means that all compounds A to M as represented herewith include all isomeric forms which are possible for the respect compound. Isomers contain the same number of atoms of each element, but have different arrangements of their atoms in space. Isomers do not necessarily share similar properties, unless they also have the same functional groups. There are many different classes of isomers, like positional isomers, cis-trans isomers and enantiomers, etc. There are two main forms of isomerism: structural isomerism and stereoisomerism (spatial isomerism).

Every isomer of the compounds A to M of formula (I) is herewith also included by the above given structures and are preferred in the sense of the present invention.

In particular, the following isomers of the compounds of formula (I) are preferred:

Compound Aa (2S,3R,4S,5S,6R)-2-((2S,3R,4S,5S,6R)-2-((3R,6R)-6-((3S,8S,9R,11R,13R,14S,17R)-3,11-dihydroxy-4,4,9,13,14-pentamethyl-2,3,4,7,8,9,10,11,12,13,14,15,16,17-tetradecahydro-1H-cyclopenta[a]phenanthren-17-yl)-2-hydroxy-2-methylheptan-3-yloxy)-4,5-dihydroxy-6-(hydroxymethyl)tetrahydro-2H-pyran-3-yloxy)-6-(hydroxymethyl)tetrahydro-2H-pyran-3,4,5-triol (Compound Aa)

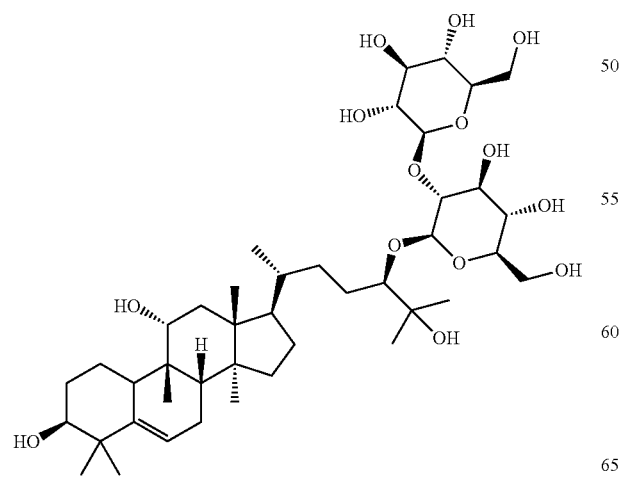

Compound Bb (2S,3R,4S,5S,6R)-2-((2S,3R,4S,5S,6R)-4,5-dihydroxy-2-((3R,6R)-2-hydroxy-2-methyl-6-((3S,9R,13R,14S,17R)-4,4,9,13,14-pentamethyl-3-((2R,3R,4S,5S,6R)-3,4,5-trihydroxy-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl) heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol

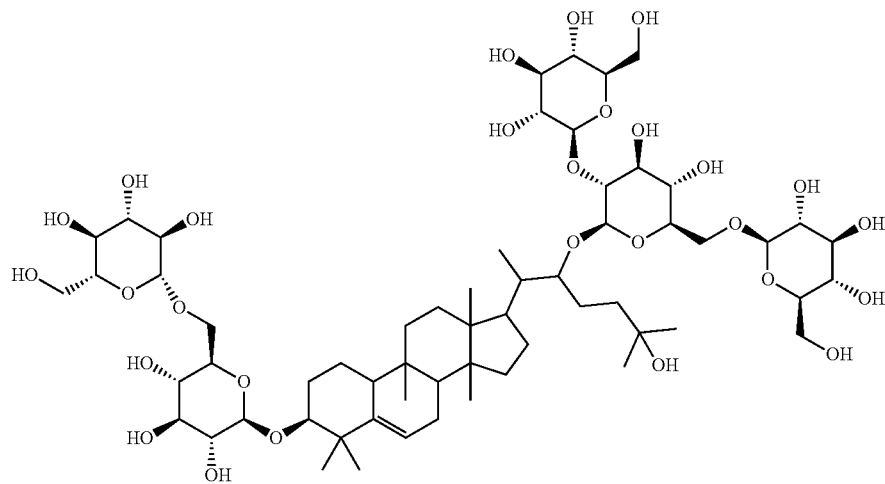

(Compound Bb)

Compound Cc (2S,3R,4S,5S,6R)-2-((2R,3S,4R,5R,6R)-6-((3S,9R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-2-(hydroxymethyl)tetrahydro-2H-pyran-3-yloxy)-6-(hydroxymethyl)tetrahydro-2H-pyran-3,4,5-triol

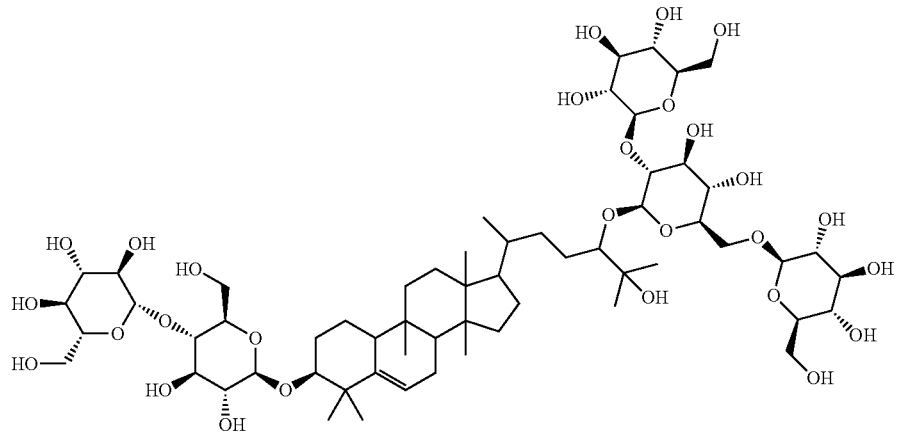

(Compound Cc)

Compound Dd (2S,3R,4S,5S,6R)-2-((2R,3R,4S,5S,6R)-2-((3S,8R,
9R,13R,14S,17R)-17-((2R,5R)-5-((2S,3R,4S,5S,
6R)-4,5-dihydroxy-3-((2S,3R,4S,5S,6R)-3,4,5-trihy-
droxy-6-(hydroxymethyl)tetrahydro-2H-pyran-2-
yloxy)-6-(((2R,3R,4S,5S,6R)-3,4,5-trihydroxy-6-
(hydroxymethyl)tetrahydro-2H-pyran-2-yloxy)
methyl)tetrahydro-2H-pyran-2-yloxy)-6-hydroxy-6-
methylheptan-2-yl)-4,4,9,13,14-pentamethyl-2,3,4,7,
8,9,10,11,12,13,14,15,16,17-tetradecahydro-1H-
cyclopenta[a]phenanthren-3-yloxy)-4,5-dihydroxy-
6-(hydroxymethyl)tetrahydro-2H-pyran-3-yloxy)-6-
(hydroxymethyl)tetrahydro-2H-pyran-3,4,5-triol

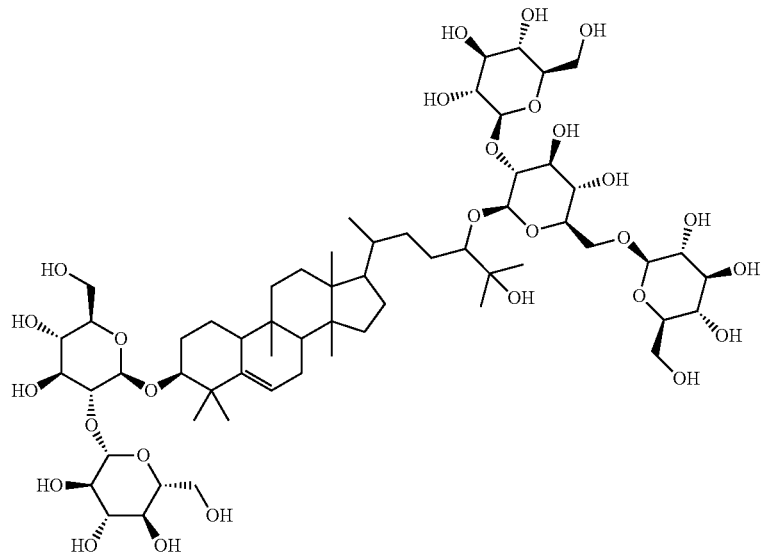

(Compound Dd)

Compound Ee (2S,3R,4S,5S,6R)-2-((2S,3R,4S,5S,6R)-4,5-dihy-
droxy-2-((3R,6R)-2-hydroxy-2-methyl-6-((3S,8R,
9R,13R,14S,17R)-4,4,9,13,14-pentamethyl-3-((2R,
3R,4S,5S,6R)-3,4,5-trihydroxy-6-(hydroxymethyl)
tetrahydro-2H-pyran-2-yloxy)-2,3,4,7,8,9,10,11,12,
13,14,15,16,17-tetradecahydro-1H-cyclopenta[a]
phenanthren-17-yl)heptan-3-yloxy)-6-(((2R,3R,4S,
5S,6R)-3,4,5-trihydroxy-6-(hydroxymethyl)
tetrahydro-2H-pyran-2-yloxy)methyl)tetrahydro-2H-
pyran-3-yloxy)-6-(hydroxymethyl)tetrahydro-2H-
pyran-3,4,5-triol

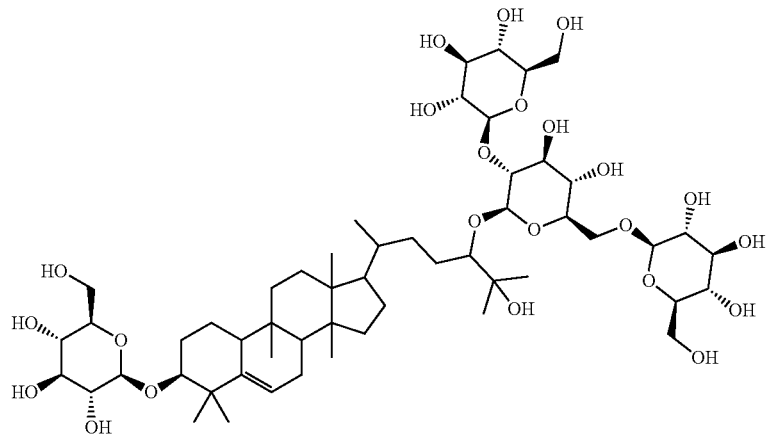

(Compound Ee)

Compound Ff (2S,3R,4S,5S,6R)-2-((2R,3R,4S,5S,6R)-2-((3S,8S,
9R,11R,13R,14S,17R)-17-((2R,5R)-5-((2S,3R,4S,
5S,6R)-4,5-dihydroxy-3-((2S,3R,4S,5S,6R)-3,4,5-
trihydroxy-6-(hydroxymethyl)tetrahydro-2H-pyran-
2-yloxy)-6-(((2R,3R,4S,5S,6R)-3,4,5-trihydroxy-6-
(hydroxymethyl)tetrahydro-2H-pyran-2-yloxy)
methyl)tetrahydro-2H-pyran-2-yloxy)-6-hydroxy-6-
methylheptan-2-yl)-11-hydroxy-4,4,9,13,14-
pentamethyl-2,3,4,7,8,9,10,11,12,13,14,15,16,17-
tetradecahydro-1H-cyclopenta[a]phenanthren-3-
yloxy)-4,5-dihydroxy-6-(hydroxymethyl)tetrahydro-
2H-pyran-3-yloxy)-6-(hydroxymethyl)tetrahydro-
2H-pyran-3,4,5-triol

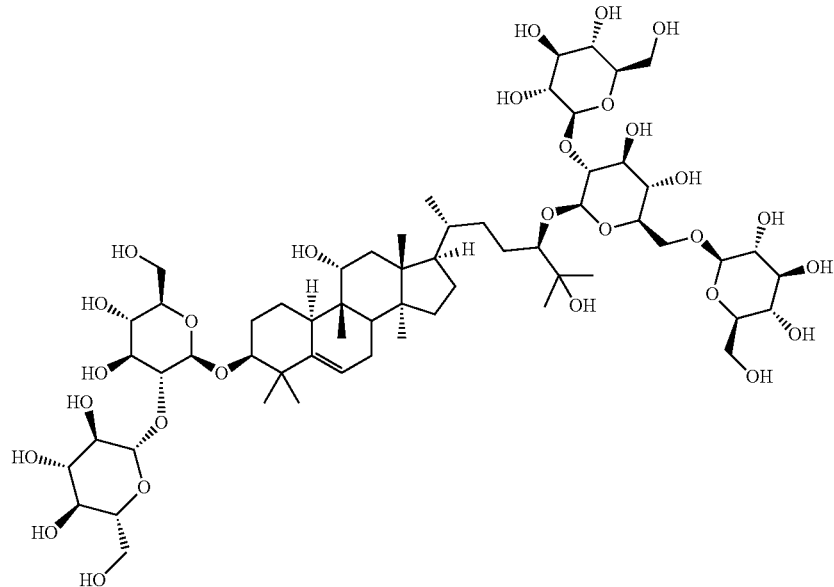

(Compound Ff)

Compound Gg (2S,3R,4S,5S,6R)-2-((2S,3R,4S,5S,6R)-4,5-dihy-
droxy-2-((3R,6R)-2-hydroxy-2-methyl-6-((3S,9R,
13R,14S,17R)-4,4,9,13,14-pentamethyl-3-((2R,3R,
4S,5S,6R)-3,4,5-trihydroxy-6-(hydroxymethyl)
tetrahydro-2H-pyran-2-yloxy)-2,3,4,7,8,9,10,11,12,
13,14,15,16,17-tetradecahydro-1H-cyclopenta[a]
phenanthren-17-yl)heptan-3-yloxy)-6-
(hydroxymethyl)tetrahydro-2H-pyran-3-yloxy)-6-
(hydroxymethyl)tetrahydro-2H-pyran-3,4,5-triol

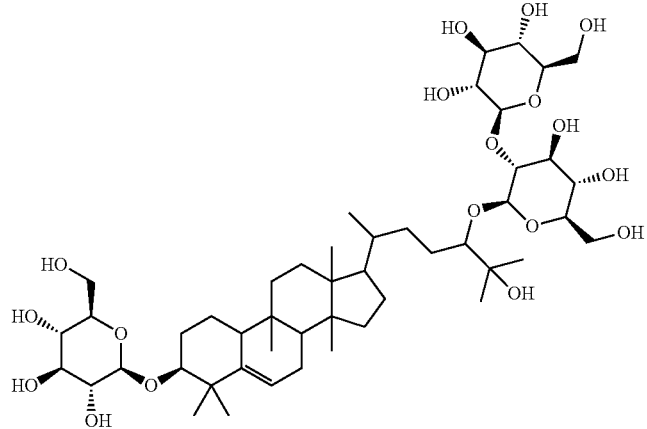

(Compound Gg)

Compound Hh (6R)-2-hydroxy-6-((3S,9R,10R,11R,13R,14S,17R)-11-hydroxy-4,4,9,13,14-pentamethyl-3-((2R,3R,4S,5S,6R)-3,4,5-trihydroxy-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)-2-methylheptan-3-one (compound Hh)

Compound Jj (9R,10R,11R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-11-hydroxy-4,4,9,13,14-pentamethyl-4,7,8,9,10,11,12,13,14,15,16,17-dodecahydro-1H-cyclopenta[a]phenanthren-3(2H)-one (Compound Jj)

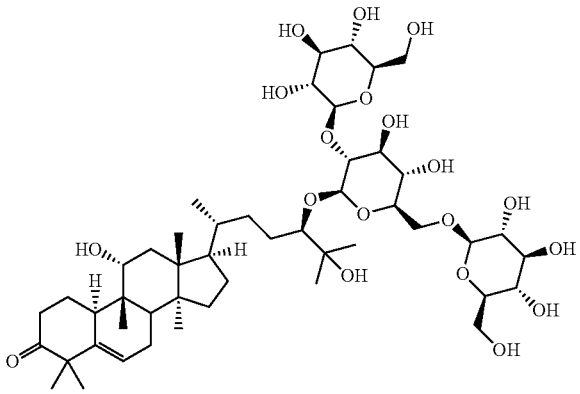

Compound Kk (2S,3R,4S,5S,6R)-2-((2S,3R,4S,5S,6R)-4,5-dihydroxy-2-((3R,6R)-2-hydroxy-6-((3S,9R,10S,13R,14S,17R)-3-hydroxy-4,4,9,13,14-pentamethyl-2,3,4,7,8,9,10,11,12,13,14,15,16,17-tetradecahydro-1H-cyclopenta[a]phenanthren-17-yl)-2-methylheptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol (Compound Kk)

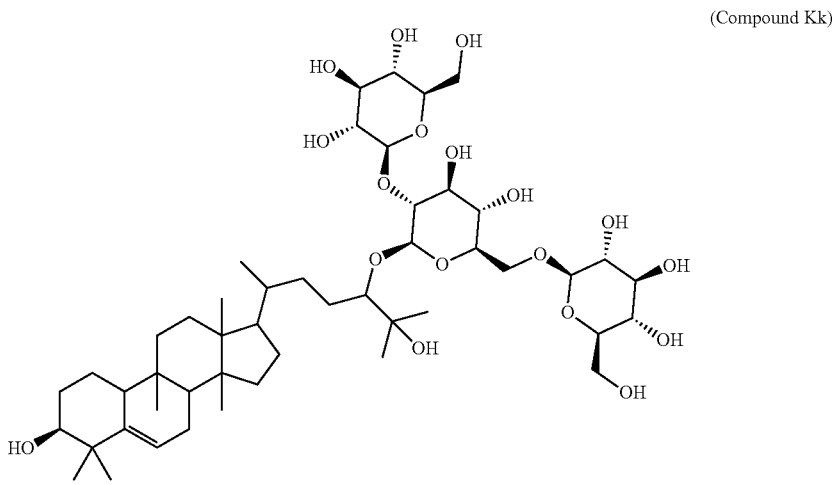

Compound L1

(3S,9R,10R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-3-((2R,3R,4S,5S,6R)-3,4,5-trihydroxy-6-(hydroxymethyl)tetrahydro-2H-pyran-2-yloxy)-3,4,7,8,9,10,12,13,14,15,16,17-dodecahydro-1H-cyclopenta[a]phenanthren-11(2H)-one

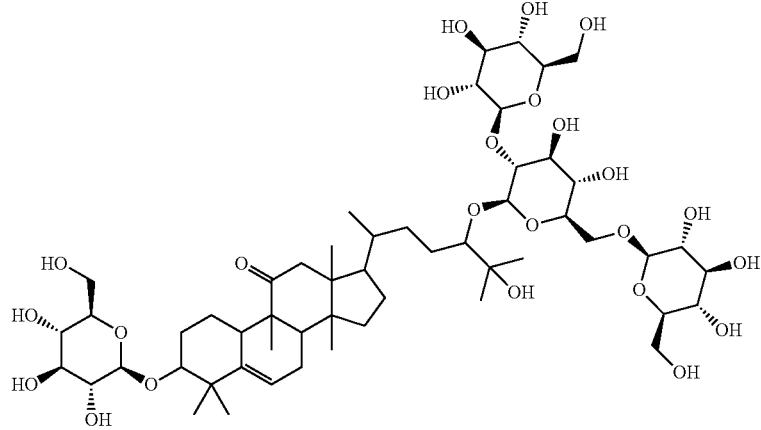

(Compound L1)

Compound Mm (2S,3R,4S,5S,6R)-2-((2S,3R,4S,5S,6R)-4,5-dihydroxy-2-((3R,6R)-2-hydroxy-2-methyl-6-((3S,9R,10S,13R,14S,17R)-4,4,9,13,14-pentamethyl-3-((2R,3R,4S,5S,6R)-3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol

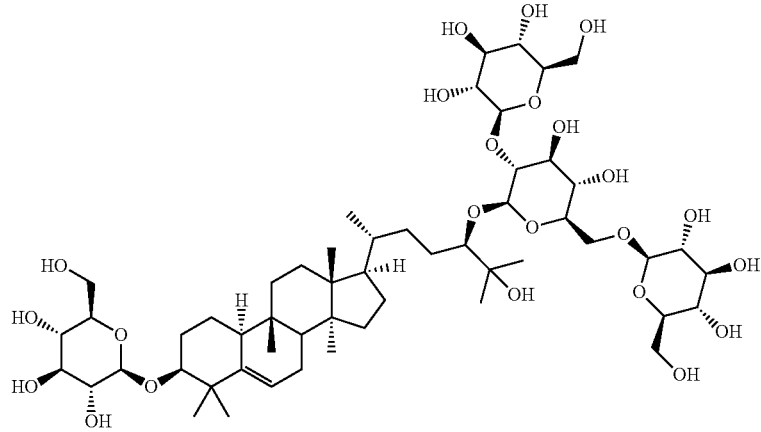

(Compound Mm)

The compounds of formula (I) when comprising two or more sugar component moieties (di- or oligosaccharide), the sugar units are linked with each other through a glycosidic bond. A glycosidic bond is a type of covalent bond that joins a carbohydrate (sugar) molecule to another group, which may or may not be another carbohydrate. A glycosidic bond is formed between the hemiacetal group of a saccharide (or a molecule derived from a saccharide) and the hydroxyl group of some organic compound such as an alcohol. If the group attached to the carbohydrate residue is not another saccharide it is referred to as an aglycone. If it is another saccharide, the resulting units can be termed as being at the reducing end or the terminal end of the structure. This is a relative nomenclature where the reducing end of the di- or polysaccharide is towards the last anomeric carbon of the structure, and the terminal end is in the opposite direction.

The glycosidic bonds of the triterpene-glycoside compounds of the present invention are as compiled in Table B:

TABLE B

| | Glycosidic bonds | | |
|---|---|---|---|
| Compound | aglycon | 3-glycosid | 24-glycosid |
| Aa (NP-014774) | mogrol | — | Glu-(1-2)-Glu |
| Bb (NP-019280) | 11-deoxymogrol | Glu-(1-2)-Glu | Glu-(1-2)-[Glu-(1-6)]-Glu |
| Cc (NP-019281) | 11-deoxymogrol | Glu | Glu-(1-2)-[Glu-(1-6)]-Glu |
| Dd (NP-019282) | mogrol | Glu-(1-2)-Xyl | Glu-(1-2)-[Glu-(1-6)]-Glu |
| Ee (NP-019501) | 11-deoxymogrol | Glu | Glu-(1-2)-Glu |
| Ff (NP-019680) | 24-oxo-mogrol | Glu-(1-6)-Glu | — |
| Gg (NP-019681) | 3-oxo-mogrol | — | Glu-(1-2)-[Glu-(1-6)]-Glu |
| Hh (NP-019682) | 11-deoxymogrol | — | Glu-(1-2)-[Glu-(1-6)]-Glu |
| Jj (NP-019683) | 11-oxomogrol | Glu | Glu-(1-2)-[Glu-(1-6)]-Glu |
| Kk (NP-019685) | 11-deoxymogrol | Glu | Glu-(1-2)-[Glu-(1-6)]-Glu |
| Ll (NP-018148) | 11-deoxymogrol | Glu-(1-6)-Glu | Glu-(1-2)-[Glu-(1-6)]-Glu |
| Mm (NP-19040) | 11-deoxymogrol | Glu-(1-4)-Glu | Glu-(1-2)-[Glu-(1-6)]-Glu |

Furthermore, the invention relates to an extract comprising one or more of a compound of formula (I), wherein the extract is obtainable by the method of aqueous and/or alcoholic extraction of the plant *Momordica grosvenorii* (Synononym *Siraitia grosvenori*).

The thus obtained extract preferably, comprises at least a compound of formula (I) selected from the group consisting of:

(2S,3R,4S,5S,6R)-2-((2S,3R,4S,5S,6R)-2-((3R,6R)-6-((3S,8S,9R,11R,13R,14S,17R)-3,11-dihydroxy-4,4,9,13,14-pentamethyl-2,3,4,7,8,9,10,11,12,13,14,15,16,17-tetradecahydro-1H-cyclopenta[a]phenanthren-17-yl)-2-hydroxy-2-methylheptan-3-yloxy)-4,5-dihydroxy-6-(hydroxymethyl)tetrahydro-2H-pyran-3-yloxy)-6-(hydroxymethyl)tetrahydro-2H-pyran-3,4,5-triol (compound Aa)

(2S,3R,4S,5S,6R)-2-((2S,3R,4S,5S,6R)-4,5-dihydroxy-2-((3R,6R)-2-hydroxy-2-methyl-6-((3S,9R,13R,14S,17R)-4,4,9,13,14-pentamethyl-3-((2R,3R,4S,5S,6R)-3,4,5-trihydroxy-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol (compound Bb)

(2S,3R,4S,5S,6R)-2-((2R,3S,4R,5R,6R)-6-((3S,9R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-2-(hydroxymethyl)tetrahydro-2H-pyran-3-yloxy)-6-(hydroxymethyl)tetrahydro-2H-pyran-3,4,5-triol (compound Cc)

(2S,3R,4S,5S,6R)-2-((2R,3R,4S,5S,6R)-2-((3S,8R,9R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-6-(hydroxymethyl)tetrahydro-2H-pyran-3-yloxy)-6-(hydroxymethyl)tetrahydro-2H-pyran-3,4,5-triol (compound Dd)

(2S,3R,4S,5S,6R)-2-((2S,3R,4S,5S,6R)-4,5-dihydroxy-2-((3R,6R)-2-hydroxy-2-methyl-6-((3S,8R,9R,13R,14S,17R)-4,4,9,13,14-pentamethyl-3-((2R,3R,4S,5S,6R)-3,4,5-trihydroxy-6-(hydroxymethyl)tetrahydro-2H-pyran-2-yloxy)-2,3,4,7,8,9,10,11,12,13,14,15,16,17-tetradeca-hydro-1H-cyclopenta[a]phenanthren-17-yl)heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol (compound Ee)

(2S,3R,4S,5S,6R)-2-((2R,3R,4S,5S,6R)-2-((3S,8S,9R,11R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-11-hydroxy-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-6-(hydroxymethyl)tetrahydro-2H-pyran-3-yloxy)-6-(hydroxymethyl)tetrahydro-2H-pyran-3,4,5-triol (compound Ff)

(2S,3R,4S,5S,6R)-2-((2S,3R,4S,5S,6R)-4,5-dihydroxy-2-((3R,6R)-2-hydroxy-2-methyl-6-((3S,9R,13R,14S,17R)-4,4,9,13,14-pentamethyl-3-((2R,3R,4S,5S,6R)-3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-

(hydroxymethyl)tetrahydro-2H-pyran-3-yloxy)-6-(hydroxymethyl)tetrahydro-2H-pyran-3,4,5-triol (compound Gg)

(6R)-2-hydroxy-6-((3S,9R,10R,11R,13R,14S,17R)-11-hydroxy-4,4,9,13,14-pentamethyl-3-((2R,3R,4S,5S,6R)-3,4,5-trihydroxy-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)-2-methylheptan-3-one (compound Hh)

(9R,10R,11R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-11-hydroxy-4,4,9,13,14-pentamethyl-4,7,8,9,10,11,12,13,14,15,16,17-dodeca hydro-1H-cyclopenta[a]phenanthren-3(2H)-one (compound Jj)

(2S,3R,4S,5S,6R)-2-((2S,3R,4S,5S,6R)-4,5-dihydroxy-2-((3R,6R)-2-hydroxy-6-((3S,9R,10S,13R,14S,17R)-3-hydroxy-4,4,9,13,14-pentamethyl-2,3,4,7,8,9,10,11,12,13,14,15,16,17-tetradecahydro-1H-cyclopenta[a]phenanthren-17-yl)-2-methylheptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol (compound Kk)

(3S,9R,10R,13R,14S,17R)-17-((2R,5R)-5-((2S,3R,4S,5S,6R)-4,5-dihydroxy-3-((2S,3R,4S,5S,6R)-3,4,5-trihydroxy-6-(hydroxymethyl)tetrahydro-2H-pyran-2-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-3-((2R,3R,4S,5S,6R)-3,4,5-trihydroxy-6-(hydroxymethyl)tetrahydro-2H-pyran-2-yloxy)-3,4,7,8,9,10,12,13,14,15,16,17-dodecahydro-1H-cyclopenta[a]phenanthren-11(2H)-one (compound Ll)

(2S,3R,4S,5S,6R)-2-((2S,3R,4S,5S,6R)-4,5-dihydroxy-2-((3R,6R)-2-hydroxy-2-methyl-6-((3S,9R,10S,13R,14S,17R)-4,4,9,13,14-pentamethyl-3-((2R,3R,4S,5S,6R)-3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-(((2R,3R,4S,5S,6R)-3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol (compound Mm).

The present invention also relates to preparations, comprising one, two, three or more of a sweetener compound of formula (I). Such a preparation used to comprise further ingredients such as aroma compounds and/or flavouring agents and/or sweeteners and/or sweet-tasting substances.

Preferred aroma compounds, flavouring agents, sweeteners and sweet-tasting substances are described below in detailed.

The preparation of the present invention comprising at least one sweetener compound of formula (I) and can be used to impart a desirable sweetness and/or flavor to a variety of oral and food compositions and pharmaceutical compositions, such as beverages, edible foodstuff, dentifrices, lipsticks and the like, which may or may not be ingestible, with or without the use of other flavorants and sweeteners. The present invention also relates to a variety of oral and food compositions and the like embodying at least one compound of formula (I) as sweetener and/or flavoring agent.

The sweetener of this invention finds application in the wide range of edible substances generally, primarily in food compositions such as candies, confections and processed foods, and beverages such as beer and soft drinks. It is also well suited for imparting a sweet flavor to other edible substances such as medicines, toothpaste, adhesives for stamps and envelopes, animal feeds and baits and the like. These examples are given solely for illustration and it is not wished to limit the scope of this invention to sweetening any particular type or types of edible materials. As a general rule, the present sweetener may be used in any application where a sweet taste is desired. The present sweetener may be used alone or in combination with other sweeteners, nutritive or nonnutritive. Also, if desired, binders or diluents may be added to the sweetener. This is not usually necessary, however, as the sweetener is a solid having excellent handling properties. This makes admixing the sweetener with an edible substance a simple conventional operation. The sweetener may be mixed with the edible substance as a solid or as a solution, if desired.

The inventions further refers to the use of a sweetener compound of formula (I) to sweet or enhance the sweeting effect in compositions or preparations which are administered to an individual in an effective amount sufficient to produce the desired degree of sweetness.

Thus the invention further relates to a method for providing a sweetening effect and/or an enhanced sweetening effect in compositions, comprising administering to an individual a sweetener compound of formula (I) in an effective amount sufficient to produce the desired degree of sweetness.

The effective amount is preferably from 1 ppm to 2000 ppm, based on the total weight of the composition and the total sum of all compound of formula (I).

The food, oral and pharmaceutical compositions will be further described in detailed.

Food Compositions

Food compositions according to the invention are any preparations or compositions which are suitable for consumption and are used for nutrition or enjoyment purposes, and are generally products which are intended to be introduced into the human or animal oral cavity, to remain there for a certain time and then either be eaten (e.g. ready-to-eat foodstuffs or feeds, see also herein below) or removed from the oral cavity again (e.g. chewing gums). Such products include any substances or products which in the processed, partially processed or unprocessed state are to be ingested by humans or animals. They also include substances which are added to orally consumable products during their manufacture, preparation or treatment and which are intended to be introduced into the human or animal oral cavity.

The food compositions according to the invention also include substances which in the unchanged, treated or prepared state are to be swallowed by a human or animal and then digested; in this respect, the orally consumable products according to the invention also include casings, coatings or other encapsulations which are to be swallowed at the same time or which may be expected to be swallowed. The expression "orally consumable product" covers ready-to-eat foodstuffs and feeds, that is to say foodstuffs or feeds that are already complete in terms of the substances that are important for the taste. The expressions "ready-to-eat foodstuff" and "ready-to-eat feed" also include drinks as well as solid or semisolid ready-to-eat foodstuffs or feeds. Examples which may be mentioned are frozen products, which must be thawed and heated to eating temperature before they are eaten. Products such as yoghurt or ice-cream as well as chewing gums or hard caramels are also included among the ready-to-eat foodstuffs or feeds.

Preferred food compositions according to the invention also include "semi-finished products". Within the context of the present text, a semi-finished product is to be understood as being an orally consumable product which, because of a very high content of flavourings and taste-imparting substances, is unsuitable for use as a ready-to-eat orally consumable product (in particular foodstuff or feed). Only by mixing with at least one further constituent (e.g. by reducing the concentration of the flavourings and taste-imparting substances in question) and optionally further process steps (e.g. heating, freezing) is the semi-finished product converted into a ready-to-eat orally consumable product (in particular foodstuff or feed). Examples of semi-finished products which may be mentioned here are Food composition according to the invention preferably comprises one or more preparations for nutrition or enjoyment purposes. These include in particular (reduced-calorie) baked goods (e.g. bread, dry biscuits, cakes, other baked articles), confectionery (e.g. chocolates, chocolate bars, other products in bar form, fruit gums, dragées, hard and soft caramels, chewing gum), non-alcoholic drinks (e.g. cocoa, coffee, green tea, black tea, (green, black) tea drinks enriched with (green, black) tea extracts, rooibos tea, other herbal teas, fruit-containing soft drinks, isotonic drinks, refreshing drinks, nectars, fruit and vegetable juices, fruit or vegetable juice preparations), instant drinks (e.g. instant cocoa drinks, instant tea drinks, instant coffee drinks), meat products (e.g. ham, fresh sausage or raw sausage preparations, spiced or marinated fresh or salt meat products), eggs or egg products (dried egg, egg white, egg yolk), cereal products (e.g. breakfast cereals, muesli bars, precooked ready-to-eat rice products), dairy products (e.g. full-fat or reduced-fat or fat-free milk drinks, rice pudding, yoghurt, kefir, cream cheese, soft cheese, hard cheese, dried milk powder, whey, butter, buttermilk, partially or completely hydrolysed milk-protein-containing products), products made from soy protein or other soybean fractions (e.g. soy milk and products produced therefrom, drinks containing isolated or enzymatically treated soy protein, drinks containing soy flour, preparations containing soy lecithin, fermented products such as tofu or tempeh or products produced therefrom and mixtures with fruit preparations and optionally flavours), fruit preparations (e.g. jams, sorbets, fruit sauces, fruit fillings), vegetable preparations (e.g. ketchup, sauces, dried vegetables, frozen vegetables, precooked vegetables, boiled-down vegetables), snacks (e.g. baked or fried potato crisps or potato dough products, maize- or groundnut-based extrudates), fat- and oil-based products or emulsions thereof (e.g. mayonnaise, remoulade, dressings, in each case full-fat or reduced-fat), other ready-made dishes and soups (e.g. dried soups, instant soups, precooked soups), spices, spice mixtures and in particular seasonings which are used, for example, in the snacks field, sweetener preparations, tablets or sachets, other preparations for sweetening or whitening drinks or other foods. The preparations within the scope of the invention can also be used in the form of semi-finished products for the production of further preparations for nutrition or enjoyment purposes. The preparations within the scope of the invention can also be in the form of capsules, tablets (uncoated and coated tablets, e.g. enteric coatings), dragées, granules, pellets, solids mixtures, dispersions in liquid phases, in the form of emulsions, in the form of powders, in the form of solutions, in the form of pastes, or in the form of other preparations which can be swallowed or chewed, and in the form of food supplements.

The preparations can also be in the form of capsules, tablets (uncoated and coated tablets, e.g. enteric coatings), dragées, granules, pellets, solids mixtures, dispersions in liquid phases, in the form of emulsions, in the form of powders, in the form of solutions, in the form of pastes, or in the form of other preparations which can be swallowed or chewed, for example in the form of food supplements.

The semi-finished products are generally used for the production of ready-to-use or ready-to-eat preparations for nutrition or enjoyment purposes.

Further constituents of a ready-to-eat preparation or semi-finished product for nutrition or enjoyment purposes can be conventional base substances, auxiliary substances and additives for foods or enjoyment foods, for example water, mixtures of fresh or processed, vegetable or animal base or raw substances (e.g. raw, roast, dried, fermented, smoked and/or boiled meat, bone, cartilage, fish, vegetables, herbs, nuts, vegetable juices, vegetable pastes or mixtures thereof), digestible or non-digestible carbohydrates (e.g. sucrose, maltose, fructose, glucose, dextrins, amylose, amylopectin, inulin, xylans, cellulose, tagatose), sugar alcohols (e.g. sorbitol, erythritol), natural or hardened fats (e.g. tallow, lard, palm fat, cocoa fat, hardened vegetable fat), oils (e.g. sunflower oil, groundnut oil, maize germ oil, olive oil, fish oil, soya oil, sesame oil), fatty acids or their salts (e.g. potassium stearate), proteinogenic or non-proteinogenic amino acids and related compounds (e.g. γ-aminobutyric acid, taurine), peptides (e.g. glutathione), natural or processed proteins (e.g. gelatin), enzymes (e.g. peptidases), nucleic acids, nucleotides, taste correctors for unpleasant taste impressions, further taste modulators for further, generally not unpleasant taste impressions, other taste-modulating substances (e.g. inositol phosphate, nucleotides such as guanosine monophosphate, adenosine monophosphate or other substances such as sodium glutamate or 2-phenoxy-propionic acid), emulsifiers (e.g. lecithins, diacylglycerols, gum arabic), stabilisers (e.g. carrageenan, alginate), preservatives (e.g. benzoic acid and its salts, sorbic acid and its salts), antioxidants (e.g. tocopherol, ascorbic acid), chelators (e.g. citric acid), organic or inorganic acidifying agents (e.g. acetic acid, phosphoric acid), additional bitter substances (e.g. quinine, caffeine, limonene, amarogentine, humulone, lupulone, catechols, tannins), substances that prevent enzymatic browning (e.g. sulfite, ascorbic acid), ethereal oils, plant extracts, natural or synthetic colourings or colouring pigments (e.g. carotinoids, flavonoids, anthocyans, chlorophyll and derivatives thereof), spices, trigeminally active substances or plant extracts containing such trigeminally active substances, synthetic, natural or nature-identical flavourings or odorants as well as odour correctors.

Food compositions according to the invention, for example those in the form of preparations or semi-finished products, preferably comprise a flavour composition in order to complete and refine the taste and/or odour. A preparation can comprise as constituents a solid carrier and a flavour composition. Suitable flavour compositions comprise, for example, synthetic, natural or nature-identical flavourings, odorants and taste-imparting substances, reaction flavourings, smoke flavourings or other flavour-giving preparations (e.g. protein (partial) hydrolysates, preferably protein (partial) hydrolysates having a high arginine content, barbecue flavourings, plant extracts, spices, spice preparations, vegetables and/or vegetable preparations) as well as suitable auxiliary substances and carriers. Particularly suitable here are the flavour compositions or constituents thereof which produce a roasted, meaty (in particular chicken, fish, seafood, beef, pork, lamb, mutton, goat), vegetable-like (in particular tomato, onion, garlic, celery, leek, mushroom, aubergine, seaweed), spicy (in particular black and white pepper, cardamom, nutmeg, pimento, mustard and mustard products), fried, yeast-like, boiled, fatty, salty and/or pungent flavour impression and accordingly can enhance the spicy impression. The flavour compositions generally comprise more than one of the mentioned ingredients.

The food compositions of the present invention are preferably selected from the group comprising
confectionery, preferably reduced-calorie or calorie-free confectionery, preferably selected from the group comprising muesli bar products, fruit gums, dragées, hard caramels and chewing gum,
non-alcoholic drinks, preferably selected from the group comprising green tea, black tea, (green, black) tea drinks enriched with (green, black) tea extracts, rooibos tea, other herbal teas, fruit-containing low-sugar or sugar-free soft drinks, isotonic drinks, nectars, fruit and vegetable juices, fruit and vegetable juice preparations,
instant drinks, preferably selected from the group comprising instant (green, black, rooibos, herbal) tea drinks,
cereal products, preferably selected from the group comprising low-sugar and sugar-free breakfast cereals and muesli bars,
dairy products, preferably selected from the group comprising reduced-fat and fat-free milk drinks, yoghurt, kefir, whey, buttermilk and ice-cream,
products made from soy protein or other soybean fractions, preferably selected from the group comprising soy milk, products produced from soy milk, drinks containing isolated or enzymatically treated soy protein, drinks containing soy flour, preparations containing soy lecithin, products produced from preparations containing soy lecithin and mixtures with fruit preparations and optionally flavours,
sweetener preparations, tablets and sachets,
sugar-free dragées,
ice-cream, with or without milk-based constituents, preferably sugar-free.

A. Aroma or Flavouring Compounds

Aroma compounds and flavouring agents are well known in the art can be added to the flavour compositions of the invention. These flavouring agents can be chosen from synthetic flavouring liquid and/or oils derived from plants leaves, flowers, fruits and so forth, and combinations thereof. Representative flavouring liquids include: artificial, natural or synthetic fruit flavours such as *eucalyptus*, lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derived flavours such as licorice or ginger.

The flavouring agent is preferably selected from the group consisting of essential oils and extracts, tinctures and balsams, such as, for example, anisole, basil oil, bergamot oil, bitter almond oil, camphor oil, citronella oil, lemon oil; *Eucalyptus citriodora* oil, *eucalyptus* oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the flavoured composition according to the invention comprises at least one flavouring agent, preferably two, three, four, five, six, seven, eight or more flavouring agents chosen from the following group: menthol (preferably I-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (–)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

In particular preferred aroma or flavouring compounds encompass menthol, cineol, eugenol, thymol, cinnamic aldehyde, peppermint oil, spearmint oil, *eucalyptus* oil, thyme oil, cinnamon oil, clove oil, spruce needle oil, fennel oil, sage oil, aniseed oil, star anise oil, chamomile oil, and caraway oil, and their mixtures.

B. Sweeteners and Sweet-Tasting Substances

The term "sweeteners" here denotes substances having a relative sweetening power of at least 25, based on the sweetening power of sucrose (which accordingly has a sweetening power of 1). Sweeteners to be used in an orally consumable product (in particular foodstuff, feed or medicament) according to the invention (a) are preferably non-cariogenic and/or have an energy content of not more than 5 kcal per gram of the orally consumable product.

Advantageous sweeteners in a preferred orally consumable product (in particular foodstuff, feed or medicament) according to the invention are selected from the following groups (a1) and (a2):

(i) naturally occurring sweeteners, preferably selected from the group comprising
miraculin, monellin, mabinlin, thaumatin, curculin, brazzein, pentaidin, D-phenylalanine, D-tryptophan, and extracts or fractions obtained from natural sources, comprising those amino acids and/or proteins, and the physiologically acceptable salts of those amino acids and/or proteins, in particular the sodium, potassium, calcium or ammonium salts;
neohesperidin dihydrochalcone, naringin dihydrochalcone, stevioside, steviolbioside, rebaudiosides, in particular rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1, baiyunoside 2, phlomisoside 1, phlomisoside 2, phlomisoside 3 and phlomisoside 4, abrusoside A, abrusoside B, abrusoside C, abrusoside D, cyclocaryoside A and cyclocaryoside I, osladin, polypodoside A, strogin 1, strogin 2, strogin 4, selligueain A, dihydroquercetin 3-acetate, perillartin, telosmoside $A_{15}$, periandrin I-V, pterocaryosides, cyclocaryosides, mukuroziocides, trans-anethole, trans-cinnamaldehyde, bryosides, bryonosides, bryonodulcosides, carnosiflosides, scandenosides, gypenosides, trilobatin, phloridzin, dihydroflavanols, hematoxylin, cyanin, chlorogenic acid, albiziasaponin, telosmosides, gaudichaudioside, mogrosides, mogroside V, hernandulcins, monatin, phyllodulcin, glycyrrhetinic acid and derivatives thereof, in particular glycosides thereof such as glycyrrhizine, and the physiologically acceptable salts of those compounds, in particular the sodium, potassium, calcium or ammonium salts;

extracts or concentrated fractions of the extracts, selected from the group comprising thaumatococcus extracts (katamfe plant), extracts from *Stevia* ssp. (in particular *Stevia rebaudiana*), swingle extracts (*Momordica* or *Siratia grosvenorii*, Luo-Han-Guo), extracts from *Glycyrrhiza* ssp. (in particular *Glycyrrhiza glabra*), extracts from *Rubus* ssp. (in particular *Rubus suavissimus*), citrus extracts and extracts from *Lippia dulcis*;

(ii) synthetic sweet-tasting substances, preferably selected from the group comprising magap, sodium cyclamate or other physiologically acceptable salts of cyclamic acid, acesulfame K or other physiologically acceptable salts of acesulfame, neohesperidin dihydrochalcone, naringin dihydrochalcone, saccharin, saccharin sodium salt, aspartame, superaspartame, neotame, alitame, advantame, perillartin, sucralose, lugduname, carrelame, sucrononate and sucrooctate.

Suitable sweet-tasting substances, including natural sources of these substances such as for example sweet-tasting carbohydrates or sugars (e.g. sucrose (synonymous with saccharose), trehalose, lactose, maltose, melizitose, raffinose, palatinose, lactulose, D-fructose, D-glucose, D-galactose, L-rhamnose, D-sorbose, D-mannose, D-tagatose, D-arabinose, Larabinose, D-ribose, D-glyceraldehyde, maltodextrin) or vegetable preparations containing predominantly these carbohydrates (e.g. from sugar beet (*Beta vulgaris* ssp., sugar fractions, sugar syrup, molasses), from sugar cane (*Saccharum officinarum* ssp., e.g. molasses, sugar syrups), from sugar maple (Acer ssp.), from agave (agave thick juice), synthetic/enzymatic hydrolysates of starch or sucrose (e.g. invert sugar syrup, highly enriched fructose syrups made from corn starch), fruit concentrates (e.g. from apples or pears, apple syrup, pear syrup), sugar alcohols (e.g. erythritol, threitol, arabitol, ribitol, xylitol, sorbitol, mannitol, dulcitol, lactitol), proteins (e.g. miraculin, monellin, thaumatin, curculin, brazzein), artificial sweeteners (magap, sodiumcyclamate, acesulfame K, neohesperidin dihydrochalcone, saccharin sodium salt, Aspartame®, superaspartame, neotame, alitame, sucralose, lugduname, carrelame, sucrononate, sucrooctate, monatin), certain sweet-tasting amino acids (glycine, D-leucine, D-threonine, D-asparagine, D-phenylalanine, D-tryptophan, L-proline), other sweet-tasting low-molecular substances, e.g. rebaudioside, stevioside, mogrosides, hernandulcin, phyllodulcin, dihydrochalcone glycosides, glycyrrhizin, glycyrrhetinic acid ammonium salt or other glycyrrhetinic acid derivatives, extracts from sweet tasting plants, in particular *Momordica grosvenori* [Luo Han Guo] *Hydrangea macrophylla*, *Stevia* ssp. (e.g. *Stevia rebaudiana*), *Rubus suavissimus*, *Polypodium vulgare*, *Abrus precatorius*, *Pterocarya paliurus*, *Baccharis gaudichaudiana*, *Albizia myriophylla*, *Bryonia dioica*, *Phlomis betonicoides*, *Hemsleya carnosiflora*, *Lippia dulcis*, *Gynostemma pentaphyllum*, *Glycyrrhiza glabra* (liquorice) or individual sweet tasting substances isolated from those plants.

C. Thickeners

Advantageous thickeners in a preferred orally consumable product (in particular foodstuff, feed or medicament) according to the invention are selected from the group comprising: crosslinked polyacrylic acids and derivatives thereof, polysaccharides and derivatives thereof, such as xanthan gum, agar-agar, alginates or tyloses, cellulose derivatives, for example carboxymethylcellulose or hydroxycarboxymethylcellulose, fatty alcohols, monoglycerides and fatty acids, polyvinyl alcohol and polyvinylpyrrolidone.

Preference is given according to the invention to an orally consumable product (in particular foodstuff or feed) which comprises milk thickened with lactic acid bacteria and/or cream thickened with lactic acid bacteria and which preferably is selected from the group comprising yoghurt, kefir and quark.

A food composition according to the invention comprising milk thickened with lactic acid bacteria and/or cream thickened with lactic acid bacteria is advantageously an orally consumable product which comprises a probiotic, wherein the probiotic is preferably selected from the group comprising *Bifidobacterium animalis* subsp. *lactis* BB-12, *Bifidobacterium animalis* subsp. *lactis* DN-173 010, *Bifidobacterium animalis* subsp. *lactis* HNO19, *Lactobacillus acidophilus* LA5, *Lactobacillus acidophilus* NCFM, *Lactobacillus johnsonii* La1, *Lactobacillus casei* immunitass/defensis, *Lactobacillus casei* Shirota (DSM 20312), *Lactobacillus casei* CRL431, *Lactobacillus reuteri* (ATCC 55730) and *Lactobacillus rhamnosus* (ATCC 53013).

D. Additives for Chewing Gums

Particular preference is given to an orally consumable product (in particular foodstuff, feed or medicament) according to the invention that is a chewing gum and comprises a chewing-gum base. The chewing-gum base is preferably selected from the group comprising chewing-gum or bubble-gum bases. The latter are softer, so that gum bubbles can also be formed therewith. Preferred chewing-gum bases according to the invention include, in addition to the natural resins or the natural latex chicle that are traditionally used, elastomers such as polyvinyl acetate (PVA), polyethylene, (low or medium molecular weight) polyisobutene (PIB), polybutadiene, isobutene-isoprene copolymers (butyl rubber), polyvinyethyl ether (PVE), polyvinylbutyl ether, copolymers of vinyl esters and vinyl ethers, styrene-butadiene copolymers (styrene-butadiene rubber, SBR) or vinyl elastomers, for example based on vinyl acetate/vinyl laurate, vinyl acetate/vinyl stearate or ethylene/vinyl acetate, as well as mixtures of the mentioned elastomers, as described, for example, in EP 0 242 325, U.S. Pat. Nos. 4,518,615, 5,093,136, 5,266,336, 5,601,858 or 6,986, 709. In addition, chewing-gum bases that are preferably to be used according to the invention preferably comprise further constituents such as, for example, (mineral) fillers, plasticisers, emulsifiers, antioxidants, waxes, fats or fatty oils, such as, for example, hardened (hydrogenated) vegetable or animal fats, mono-, di- or tri-glycerides. Suitable (mineral) fillers are, for example, calcium carbonate, titanium dioxide, silicon dioxide, talcum, aluminium oxide, dicalcium phosphate, tricalcium phosphate, magnesium hydroxide and mixtures thereof. Suitable plasticisers, or agents for preventing adhesion (detackifiers), are, for example, lanolin, stearic acid, sodium stearate, ethyl acetate, diacetin (glycerol diacetate), triacetin (glycerol triacetate), triethyl citrate. Suitable waxes are, for example, paraffin waxes, candelilla wax, carnauba wax, microcrystalline waxes and polyethylene waxes. Suitable emulsifiers are, for example, phosphatides such as lecithin, mono- and di-glycerides of fatty acids, for example glycerol monostearate.

Chewing gums according to the invention (in particular as disclosed above) preferably comprise constituents such as sugars of different types, sugar substitutes, other sweet-tasting substances, sugar alcohols (in particular sorbitol, xylitol, mannitol), ingredients having a cooling effect, taste correctors for unpleasant taste impressions, further taste-modulating substances (e.g. inositol phosphate, nucleotides such as guanosine monophosphate, adenosine monophosphate or other substances such as sodium glutamate or 2-phenoxypropionic acid), humectants, thickeners, emulsifiers, stabilisers, odour correctors and flavours (e.g. *eucalyptus*-menthol, cherry, strawberry, grapefruit, vanilla, banana, citrus, peach, blackcurrant, tropical fruits, ginger, coffee, cinnamon, combinations (of the mentioned flavours) with mint flavours as well as spearmint and peppermint on their own). The combination inter alia of the flavours with further substances that have cooling, warming and/or mouthwatering properties is of particular interest.

E. Vitamins

In another embodiment of the present invention the compositions may include vitamins (component e1). Vitamins have diverse biochemical functions. Some have hormone-like functions as regulators of mineral metabolism (e.g., vitamin D), or regulators of cell and tissue growth and differentiation (e.g., some forms of vitamin A). Others function as antioxidants (e.g., vitamin E and sometimes vitamin C). The largest number of vitamins (e.g. B complex vitamins) act as precursors for enzyme cofactors, that help enzymes in their work as catalysts in metabolism. In this role, vitamins may be tightly bound to enzymes as part of prosthetic groups: For example, biotin is part of enzymes involved in making fatty acids. Vitamins may also be less tightly bound to enzyme catalysts as coenzymes, detachable molecules that function to carry chemical groups or electrons between molecules. For example, folic acid carries various forms of carbon group methyl, formyl, and methylene in the cell. Although these roles in assisting enzyme-substrate reactions are vitamins' best-known function, the other vitamin functions are equally important. In the course of the present invention suitable vitamins are selected from the group consisting of Vitamin A (retinol, retinal, beta carotene),
Vitamin $B_1$ (thiamine),
Vitamin $B_2$ (riboflavin),
Vitamin $B_3$ (niacin, niacinamide),
Vitamin $B_5$ (panthothenic acid),
Vitamin $B_6$ (pyridoxine, pyridoxamine, paridoxal),
Vitamin $B_7$ (biotin),
Vitamin $B_9$ (folic acid, folinic acid),
Vitamin $B_{12}$ (cyanobalamin, hydoxycobalmin, methylcobalmin),
Vitamin C (ascorbic acid),
Vitamin D (cholecalciferol),
Vitamin E (tocopherols, tocotrienols), and
Vitamin K (phyolloquinone, menaquinone).

The preferred vitamins are ascorbic acid and tocopherols.

Said vitamins may be present in the food composition in amounts of about 0.1 to about 5% b.w., and preferably about 0.5 to about 1% b.w.

Oral Compositions

Typical examples for non-food oral compositions encompass products for cleaning and protecting teeth and refreshing the oral cavity.

The oral compositions of the present invention typically comprise an abrasive system (abrasive or polishing agent), such as e.g. silicas, calcium carbonates, calcium phosphates, aluminium oxides and/or hydroxyapatites, surface-active substances, such as e.g. sodium lauryl sulfate, sodium lauryl sarcosinate and/or cocamidopropyl betaine, moisture-retaining agents, such as e.g. glycerol and/or sorbitol, thickening agents, such as e.g. carboxymethylcellulose, polyethylene glycols, carrageenan and/or Laponite, sweeteners, such as e.g. saccharin, flavour correctants for unpleasant taste impressions, flavour correctants for further, as a rule not unpleasant taste impressions, flavour-modulating substances (e.g. inositol phosphate, nucleotides, such as guanosine monophosphate, adenosine monophosphate or other substances, such as sodium glutamate or 2-phenoxypropionic acid), cooling active compounds, such as e.g. menthol derivatives (e.g. L-menthyl lactate, L-menthyl alkyl carbonates, menthone ketals, menthanecarboxylic acid amides), 2,2,2-trialkylacetic acid amides (e.g. 2,2-diisopropylpropionic acid methylamide), icilin and icilin derivatives, stabilizers and active compounds, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, chlorhexidine, cetylpyridinium chloride, aluminium lactate, potassium citrate, potassium nitrate, potassium chloride, strontium chloride, hydrogen peroxide, aromas, sodium bicarbonate and/or odour correctants.

Formulations or products according to the invention in the form of chewing gums or, in particular, dental care chewing gums comprise chewing gum bases which comprise elastomers, such as, for example, polyvinyl acetates (PVA), polyethylenes, (low or medium molecular weight) polyisobutenes (PIB), polybutadienes, isobutene-isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, e.g. based on vinyl acetate/vinyl laurate, vinyl acetate/vinyl stearate or ethylene/vinyl acetate, and mixtures of the elastomers mentioned, as described, for example, in EP 0 242 325, U.S. Pat. Nos. 4,518,615, 5,093,136, 5,266,336 5,601,858 or 6,986,709. In addition, chewing gum bases comprise further constituents, such as, for example, sugars, sugar substitutes or sweet-tasing substances in particular those described in WO 2009/21558, (mineral) fillers, plasticizers, emulsifiers, antioxidants, waxes, fats or fatty oils, such as, for example, hardened (hydrogenated) plant or animal fats, and mono-, di- or triglycerides. Suitable (mineral) fillers are, for example, calcium carbonate, titanium dioxide, silicon dioxide, talc, aluminium oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate) and triethyl citrate. Suitable waxes are, for example, paraffin waxes, candelilla wax, carnauba wax, microcrystalline waxes and polyethylene waxes. Suitable emulsifiers are, for example, phosphatides, such as lecithin, and mono- and diglycerides of fatty acids, e.g. glycerol monostearate.

Formulations or products according to the invention (in particular those which are in the form of an oral care formulation or product or in the form of a formulation) preferably additionally comprise one or more aroma and/or flavouring substances, such as essential oils and extracts, tinctures and balsams, such as, for example, anisole, basil oil, bergamot oil, bitter almond oil, camphor oil, citronella oil, lemon oil; *Eucalyptus citriodora* oil, *eucalyptus* oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if said formulations or products comprise at least one aroma substance, preferably 2, 3, 4, 5, 6, 7, 8, 9, 10 or more aroma substances, chosen from the following group: menthol (preferably I-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

Pharmaceutical Compositions

Pharmaceutical compositions according to the present invention may include similar additives as already explained for the food and oral compositions, such as aroma and flavors. Pharmaceutical compositions may further include, oil bodies or emulsifiers and in particular co-actives supporting the beneficial properties of the pharmaceutical active agent. Therefore, the border between food compositions and pharmaceutical compositions is in flow and it should be understood that components cited for one application are recommended for the other mutatis-mutandis without literal repetition.

Further subject of the present invention is the use of a sweetener compound of formula (I) or a preparation comprising at least one sweetener compound of formula (I) to sweet or enhance the sweeting effect in compositions, such as oral or food or pharmaceutical compositions, and that are administered to an individual. Preferably, one or more of the compound of formula (I) is used in an amount from 1 ppm to 2000 ppm by weight, based on the total weight of the composition and base on the total sum of all compounds of formula (I), if more than one compound of formula (I) is used. More preferably, the sweetener compounds of formula (I) are used in an amount from 10 ppm to 1000 ppm by weight, most preferably in an amount of 20 ppm to 500 ppm by weight, based on the total weight of the composition and base on the total sum of all compounds of formula (I), if more than one compound of formula (I) is used.

In another preferred embodiment the sweetener compounds of formula (I) or a preparation comprising at least one sweetener compound of formula (I) is used to synergistically enhance a sweet taste of a sweet-tasting substance in a composition. The preferred compounds of formula (I) are preferably selected from the group consisting of:

Compound A
3,11-dihydroxy-4,4,9,13,14-pentamethyl-2,3,4,7,8,9,10,11,12,13,14,15,16,17-tetradecahydro-1H-cyclopenta[a]phenanthren-17-yl)-2-hydroxy-2-methylheptan-3-yloxy)-4,5-dihydroxy-6-(hydroxymethyl)tetrahydro-2H-pyran-3-yloxy)-6-(hydroxymethyl)tetrahydro-2H-pyran-3,4,5-triol;

Compound B
4,5-dihydroxy-2-(2-hydroxy-2-methyl-6-((4,4,9,13,14-pentamethyl-3-(3,4,5-trihydroxy-6-((3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-((3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol;

Compound C
4,5-dihydroxy-3-(3,4,5-trihydroxy-6-(hydroxymethyl)tetrahydro-2H-pyran-2-yloxy)-6-((3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-2-(hydroxymethyl)tetrahydro-2H-pyran-3-yloxy)-6-(hydroxymethyl)tetrahydro-2H-pyran-3,4,5-triol;

Compound D
2-(2-(17-(5-(4,5-di hydroxy-3-(3,4,5-trihydroxy-6-(hydroxymethyl)tetrahydro-2H-pyran-2-yloxy)-6-((3,4,5-trihydroxy-6-(hydroxymethyl)tetrahydro-2H-pyran-2-yloxy) methyl)tetrahydro-2H-pyran-2-yloxy)-6-hydroxy-6-methylheptan-2-yl)-4,4,9,13,14-pentamethyl-2,3,4,7,8,9,10,11,12,13,14,15,16,17-tetradecahydro-1H-cyclopenta[a]phenanthren-3-yloxy)-4,5-dihydroxy-6-(hydroxymethyl)tetrahydro-2H-pyran-3-yloxy)-6-(hydroxymethyl)tetrahydro-2H-pyran-3,4,5-triol;

Compound E
2-(4,5-dihydroxy-2-(2-hydroxy-2-methyl-6-(4,4,9,13,14-pentamethyl-3-(3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-((3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol;
Compound F
2-((6-(6-(3-(4,5-dihydroxy-6-(hydroxymethyl)-3-(3,4,5-trihydroxytetrahydro-2H-pyran-2-yloxy)tetrahydro-2H-pyran-2-yloxy)-11-hydroxy-4,4,9,13,14-pentamethyl-2,3,4,7,8,9,10,11,12,13,14,15,16,17-tetradecahydro-1H-cyclopenta[a]phenanthren-17-yl)-2-hydroxy-2-methylheptan-3-yloxy)-3,4-dihydroxy-5-(3,4,5-trihydroxy-6-(hydroxymethyl)tetrahydro-2H-pyran-2-yloxy)tetrahydro-2H-pyran-2-yl)methoxy)-6-(hydroxymethyl)tetrahydro-2H-pyran-3,4,5-triol;
Compound G
2-(4,5-dihydroxy-2-(3-hydroxy-2-methyl-6-(4,4,9,13,14-pentamethyl-3-(3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-2-yloxy)-6-(hydroxymethyl)tetrahydro-2H-pyran-3-yloxy)-6-(hydroxymethyl)tetrahydro-2H-pyran-3,4,5-triol;
Compound H
2-hydroxy-6-(11-hydroxy-4,4,9,13,14-pentamethyl-3-(3,4,5-trihydroxy-6-((3,4,5-trihydroxy-6-(hydroxymethyl)tetrahydro-2H-pyran-2-yloxy)methyl)tetrahydro-2H-pyran-2-yloxy)-2,3,4,7,8,9,10,11,12,13,14,15,16,17-tetradecahydro-1H-cyclopenta[a]phenanthren-17-yl)-2-methylheptan-3-one;
Compound J
17-(5-(4,5-dihydroxy-3-(3,4,5-trihydroxy-6-(hydroxymethyl)tetrahydro-2H-pyran-2-yloxy)-6-((3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-11-hydroxy-4,4,9,13,14-pentamethyl-4,7,8,9,10,11,12,13,14,15,16,17-dodeca hydro-1H-cyclopenta[a]phenanthren-3(2H)-one;
Compound K
2-(4,5-dihydroxy-2-(2-hydroxy-6-(3-hydroxy-4,4,9,13,14-pentamethyl-2,3,4,7,8,9,10,11,12,13,14,15,16,17-tetradecahydro-1H-cyclopenta[a]phenanthren-17-yl)-2-methylheptan-3-yloxy)-6-((3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol;
Compound L
17-(5-(4,5-dihydroxy-3-(3,4,5-trihydroxy-6-(hydroxymethyl)tetrahydro-2H-pyran-2-yloxy)-6-((3,4,5-trihydroxy-6-(hydroxymethyl)tetrahydro-2H-pyran-2-yloxy)methyl)tetrahydro-2H-pyran-2-yloxy)-6-hydroxy-6-methylheptan-2-yl)-4,4,9,13,14-pentamethyl-3-(3,4,5-trihydroxy-6-(hydroxymethyl)tetrahydro-2H-pyran-2-yloxy)-3,4,7,8,9,10,12,13,14,15,16,17-dodecahydro-1H-cyclopenta[a]phenanthren-11(2H)-one;
Compound M
2-(4,5-dihydroxy-2-(2-hydroxy-2-methyl-6-(4,4,9,13,14-pentamethyl-3-(3,4,5-trihydroxy-6-(hydroxymethyl)tetrahydro-2H-pyran-2-yloxy)-2,3,4,7,8,9,10,11,12,13,14,15,16,17-tetradecahydro-1H-cyclopenta[a]phenanthren-17-yl)heptan-3-yloxy)-6-((3,4,5-trihydroxy-6-(hydroxymethyl)tetrahydro-2H-pyran-2-yloxy)methyl)tetrahydro-2H-pyran-3-yloxy)-6-(hydroxymethyl)tetrahydro-2H-pyran-3,4,5-triol;
wherein the isomeric forms (Aa) to (Mm) which have been specified are most preferred.

Further subject of the invention is an extract containing one or more of a compound of formula (I)

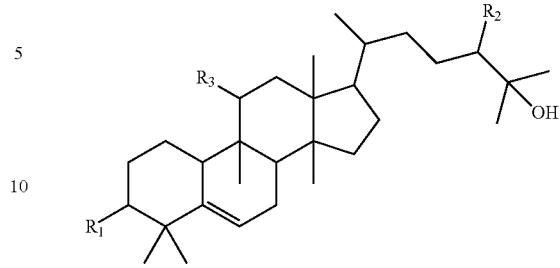

(I)

wherein $R_1$, $R_2$, $R_3$ are independently of one another and denote hydrogen, hydroxyl, carbonyl or
a sugar moiety selected from a monosaccharide and/or oligosaccharide,
wherein the extract is obtainable by the method of aqueous and/or alcoholic extraction of plant materials selected from the group consisting of *Momordica grosvenorii* (*Siraitia grosvenori*).

In this context "plant materials" refers to parts of the respective plant of *Momordica grosvenorii* (*Siraitia grosvenori*). The plant materials may include parts of the whole plant selected from the group consisting of blossoms, fruits, buds, roots, seeds and/or leaves or the whole plant itself.

The extract comprises at least one compound of formula (I) selected from the group consisting of compound A, B, C, D, E, F, G, H, J, K, L, M or mixtures thereof, wherein the isomeric forms (Aa) to (Mm) which have been specified are most preferred.

More preferably, the extract comprises at least two, three, four, five, six, seven, eight, nine, ten or eleven compounds of formula (I). Preferably, the extract comprises all compounds I to XII of formula (I), especially the all isomeric forms (Aa) to (Mm) which have been specified.

Extraction

The extracts according to the present invention may be prepared by methods known per se, i.e. for example by aqueous, alcoholic or aqueous/alcoholic extraction of the plants or parts thereof or shells of the litchi fruits. Suitable extraction processes are any conventional extraction processes, such as maceration, re-maceration, digestion, agitation maceration, vortex extraction, ultrasonic extraction, counter current extraction, percolation, re percolation, evacolation (extraction under reduced pressure), diacolation and solid/liquid extraction under continuous reflux. Percolation is advantageous for industrial use. Litchi shells are preferably used as the starting material and may be mechanically size-reduced before the extraction process. Any size reduction methods known to the expert, for example freeze grinding, may be used. Preferred solvents for the extraction process are organic solvents, water (preferably hot water with a temperature above 80° C. and more particularly above 95° C. or mixtures of organic solvents and water, more particularly low molecular weight alcohols with more or less high water contents. Extraction with methanol, ethanol, isopropanol and water-containing mixtures thereof is particularly preferred. The extraction process is generally carried out at about 20 to about 100° C. and preferably at about 50 to about 70° C. In one preferred embodiment, the extraction process is carried out in an inert gas atmosphere to avoid oxidation of the ingredients of the extract. This is particularly important where extraction is carried out at temperatures above 40° C. The extraction times are selected by the expert in dependence upon the starting material, the extraction process, the extraction temperature and the ratio of solvent to raw material, etc. After the extraction process, the crude extracts obtained may optionally be subjected to other typical steps, such as for example purification, concentration and/or decoloration. If desired, the extracts thus prepared may be subjected, for example, to the selective removal of individual unwanted ingredients. The extraction process may be carried out to any degree, but is usually continued to exhaustion. Typical yields (=extract dry matter, based on the quantity of raw material used) in the extraction of the starting materials are of the order of about 1 to about 20, %, preferably about 2 to about 15 and more preferably about 5 to about 10% b.w.—calculated on the starting materials.

The content in the extract of each of the compounds (A) to (M) differs from batch to batch depending on the used raw material of fruits of M. grosvenori. Usually the major triterpene glycoside in extracts of M. grosvenori is Mogroside V (CAS 88901-36-4) with a relative amount of 50 to 90% of the total amount of triterpene glycosides. Compounds (A) to (M) usually represent between 0.01 to 5% of total amount of triterpene glycosides in M. grosvenori.

Further, the invention relates to a method for providing a sweetening effect and/or an enhanced sweetening effect in compositions, such as food or oral or pharmaceutical compositions, comprising administering to an individual at least a sweetener compound of formula (I) or a preparation comprising at least one compound of formula (I) or an extract comprising at least one compound of formula (I).

Preferred food compositions are e.g. confectionery, such as chocolate, chewing gums, hard caramels, and milk base products, such as yoghurt, buttermilk, cheese, ice creams, and beverages, such as non-alcoholic drinks, refreshing drinks, fruit-containing drinks, and baked goods, and meat products, such as sausages, and cereal products, such as muesli, breakfast cereals, and fruit preparations, such as jams, sorbets, fruit sauces and "semi-finished products". This list of possible application is not restricted to the mentioned application, but is only illustrative. The sweetener compounds of formula (I) can be provided in every product to provide a kind of sweetness.

Further, the invention relates to a method of using a sweetener compound of formula (I) to synergistically enhance a sweet taste of a sweet-tasting substance.

The invention, also preferably relates to a method of imparting or enhancing the sweetness of oral and composition which comprises adding thereto one or more compounds of formula (I) in an amount of from about 1 ppm to about 2000 ppm.

INDUSTRIAL APPLICATION

More particularly, the present invention also refers to an oral edible composition, comprising an edible substance and at least one compound of formula (I)

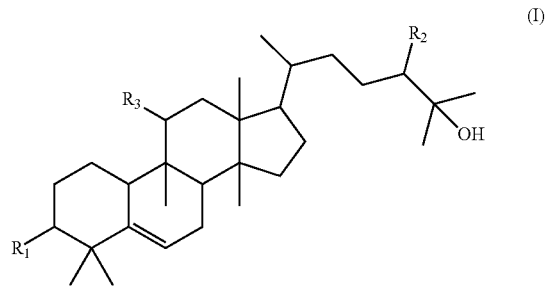

wherein $R_1$, $R_2$, $R_3$ are independently of one another and denote hydrogen, hydroxyl, carbonyl or a sugar moiety selected from the group consisting of a monosaccharide and/or oligosaccharide, and
in an effective amount sufficient to produce the desired degree of sweetness.

The effective amount is preferably from 1 ppm to 2000 ppm (basis edible substance), more preferably from 10 ppm by weight to 1000 ppm by weight, most preferred from 20 ppm by weight to 500 ppm by weight, based on the total weight of the composition and the total sum of all compounds of formula (I).

Preferred edible compositions are the preferred food compositions which have been described herein.

Further, the compounds of formula (I) are suitable as sweetener in liable compositions.

The invention will be further described by the following Examples. These Examples are provided to illustrate the invention and are not to be construed as limiting the scope of the invention.

Further, the invention refers to a preparation, comprising one, two, three or more of a sweetener compound of formula (I), wherein the preparation optionally further comprises aroma compounds and/or flavouring agents and/or sweeteners and/or sweet-tasting substances.

The preparation is preferably an oral edible composition.

EXAMPLES

The examples which follow are intended to illustrate the present invention without limiting the invention. Unless indicated otherwise all amounts, parts and percentages are based on the weight and the total amount or on the total weight and the total amount of the preparations.

Example 1

Extraction and Identification of Compounds of Formula (I)
A) Extraction 2 kg dried fruits of Momordica grosvenori (Syn. Siraitia grosvenori), provided by Cfm Oskar Tropitzsch, Marktredwitz, Germany, were extracted with 18l methanol-MTB-ether at room temperature for 24 h (yield: 275 g extract). 1 kg dried fruits of Momordica grosvenori (Syn. Siraitia grosvenori), provided by DAXINGANLING SNOW LOTUS HERB BIO-TECHNOLOGY CO., LTD., China, were extracted with 10l methanol at room temperature for 24 h (yield: 310 g extract).
B) Enrichment In order to remove very polar sugars the raw extract were dissolved in 5l water-methanol (9:1) and 500 ml of absorber resin HP-20 was added. The filtered resin was washed with water to elute the polar ingredients which are not wanted. Elution with methanol yielded 37 g of a mixture of triterpene-glycosides.

C) Pre-Fractionation by Normal Phase Chromatography

The resulted fraction of B) was then separated by medium pressure chromatography under the following conditions:
- stationary phase: Silica 60 (Merck)
- mobile phase solvent A: $CHCl_3$—methanol—water 1680:720:120
- mobile phase solvent: B $CHCl_3$—methanol—water 1350:900:225
- gradient: 100% A to 50% A in 40 min, 10 min 50% A, 10 min 90% methanol—10% water
- column dimension: 50×250 mm Seven fractions were collected and evaporated as set out in the following Table C:

TABLE C

| Fractions | | |
|---|---|---|
| Fraction | Volume [ml] | Yield [g] |
| C-1780-A | 150 | 5.85 |
| C-1780-B | 220 | 4.72 |
| C-1780-C | 450 | 3.85 |
| C-1780-D | 550 | 2.96 |
| C-1780-E | 410 | 2.08 |
| C-1780-F | 500 | 2.32 |
| C-1780-G | 550 | 13.38 |

D) Pre-Fractionation by Reverse Phase Chromatography 300 g raw extract of *M. grosvenori* were separated by reverse phase medium pressure chromatography under the following conditions:

Conditions of the separation of enriched triterpen glycoside fraction:
- stationary phase: RP-18, 40-63μ (Merck)
- mobile phase solvent A: water
- mobile phase solvent B: methanol
- column dimension: 50×250 mm Seven Fractions were collected as set out in the following Table D:

TABLE C

| Fractions | | |
|---|---|---|
| Fraction | Volume [ml] | Yield [g] |
| H-1714-B | 3000 | 54.06 |
| H-1714-C | 3000 | 32.52 |
| H-1714-D | 3000 | 36.69 |
| H-1714-E | 3000 | 36.87 |
| H-1714-F | 3000 | 11.25 |
| H-1714-G | 3000 | 3.57 |
| H-1714-I | 3000 | 0.96 |

E) Final Purification by Reverse Phase Chromatography

Pure compounds were isolated by reverse phase chromatography using enriched fractions generated by pre-fractionation steps described in step D).

TABLE 1

| Conditions of the separation of C-1780-C | |
|---|---|
| stationary phase | LichrospherSelect B. 10 μm |
| mobile phase solvent A | water + 5 mM ammoniumformiat + 0.1% formic acid |
| mobile phase solvent B | acetonitril/methanol = 1:1 + 5 mM ammoniumformiat + 0.1% formic acid |

TABLE 1-continued

| Conditions of the separation of C-1780-C | |
|---|---|
| flowrate | 80 ml/min |
| gradient | 36-65% B in 57 min |
| detection | ELSD and UV |
| column dimension | 50 × 250 mm |
| used prefraction sample | 3.85 g C-1780-C |

TABLE 2

| Conditions of the separation of C-1780-D | |
|---|---|
| stationary phase | LichrospherSelect B. 10 μm |
| mobile phase solvent A | water + 5 mM ammoniumformiat + 0.1% formic acid |
| mobile phase solvent B | acetonitril/methanol = 1:1 + 5 mM ammoniumformiat + 0.1% formic acid |
| flowrate | 80 ml/min |
| gradient | 32-50% B in 57 min |
| detection | ELSD and UV |
| column dimension | 50 × 250 mm |
| used prefraction sample | 2.96 g C-1780-D |

TABLE 3

| Conditions of the separation of C-1780-E | |
|---|---|
| stationary phase | LichrospherSelect B. 10 μm |
| mobile phase solvent A | water + 5 mM ammoniumformiat + 0.1% formic acid |
| mobile phase solvent B | acetonitril/methanol = 1:1 + 5 mM ammoniumformiat + 0.1% formic acid |
| flowrate | 80 ml/min |
| gradient | 32-50% B in 57 min |
| detection | ELSD and UV |
| column dimension | 50 × 250 mm |
| used prefraction sample | 2.08 g C-1780-E |

TABLE 4

| Conditions of the separation of C-1780-F | |
|---|---|
| stationary phase | LichrospherSelect B. 10 μm |
| mobile phase solvent A | water + 5 mM ammoniumformiat + 0.1% formic acid |
| mobile phase solvent B | acetonitril/methanol = 1:1 + 5 mM ammoniumformiat + 0.1% formic acid |
| flowrate | 80 ml/min |
| gradient | 29-49% B in 57 min |
| detection | ELSD and UV |
| column dimension | 50 × 250 mm |
| used prefraction sample | 2.32 g C-1780-F |

TABLE 5

| Conditions of the separation of H-1949-G | |
|---|---|
| stationary phase | LichrospherSelect B. 10 μm |
| mobile phase solvent A | water + 5 mM ammoniumformiat + 0.1% formic acid |
| mobile phase solvent B | acetonitril/methanol = 1:1 + 5 mM ammoniumformiat + 0.1% formic acid |
| flowrate | 80 ml/min |
| gradient | 35-50% B in 57 min |
| detection | ELSD and UV |
| column dimension | 50 × 250 mm |
| used prefraction sample | 0.57 g H-1714-G |

TABLE 6

Conditions of the separation of C-1750-N

| | |
|---|---|
| stationary phase | Kromasil C-18 |
| mobile phase solvent A | water + 0.1% formic acid |
| mobile phase solvent B | acetonitril + 0.1% formic acid |
| flowrate | 80 ml/min |
| gradient | 20-37% B in 57 min |
| detection | ELSD and UV |
| column dimension | 50 × 250 mm |
| used prefraction sample | 1.3 g H-1714-F |

TABLE 7

Conditions of the separation of C-1743-A

| | |
|---|---|
| stationary phase | Kromasil C-18 |
| mobile phase solvent A | water + 5 mM ammoniumformiat + 0.1% formic acid |
| mobile phase solvent B | methanol = 1:1 + 5 mM ammoniumformiat + 0.1% formic acid |
| flowrate | 80 ml/min |
| gradient | 53-62% B in 57 min |
| detection | ELSD and UV |
| column dimension | 50 × 250 mm |
| used prefraction sample | 2.08 g H-1714-F |

TABLE 8

Conditions of the separation of H-1714-G

| | |
|---|---|
| stationary phase | Kromasil C-18 |
| mobile phase solvent A | water + 0.1% formic acid |
| mobile phase solvent B | acetonitril + 0.1% formic acid |
| flowrate | 80 ml/min |
| gradient | 20-37% B in 57 min |
| detection | ELSD and UV |
| column dimension | 50 × 250 mm |
| used prefraction sample | 1.3 g H-1714-F |

F) Analytical Characterisation of Isolated Triterpene-Glycosides

Fractions from preparative HPLC were collected (40 ml each) and analysed by HPLC-MS. Fractions containing the same compound according to retention time and mass spectrum were combined, evaporated and analysed by HPLC-MS and NMR ($^1$H-NMR. HH-COSY. HSQC. HMBC). Structures were elucidated by interpretation of NMR and MS data.

TABLE 9

Conditions of the HPLC-MS of isolated compounds

| | |
|---|---|
| HPLC | HPLC PE series 200 |
| MS System | Applied Biosystems API 150. 165 oder 365 |
| datasystem | Analyst 1.3 |
| stationary phase | Phenomenex Luna C8 (2). 5 µm. 50 × 4.6 mm |
| flowrate | 1.2 mL/min |
| detection | (+/(−)-ESI. Fast-Switching-Mode. ELSD (Sedex75) |
| injection volume | 10 µL |
| mobile phase: | A: 5 mM Ammoniumformiat and 0.1% formic acid B: Acetonitril/Methanol = 1:1 + 5 mM Ammoniumformiat + 0.1% formic acid (pH 3) |

| gradient | time [min] | % A | % B |
|---|---|---|---|
| | 0 | 95 | 5 |
| | 6 | 0 | 100 |
| | 8 | 0 | 100 |

G) Identification: Analytical Characterisation of the Compounds

The isolated compounds of formula (I) are characterised through mass spectroscopy and NMR spectroscopy, see FIGS. 1 to 24. The compounds were identified as:

Compound Aa

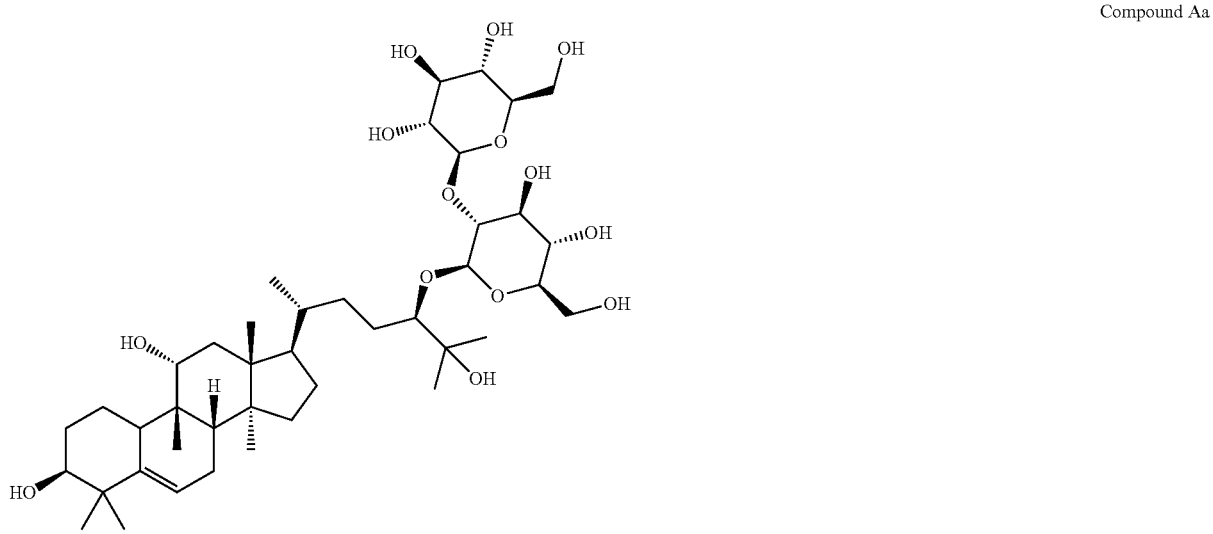

Compound Bb
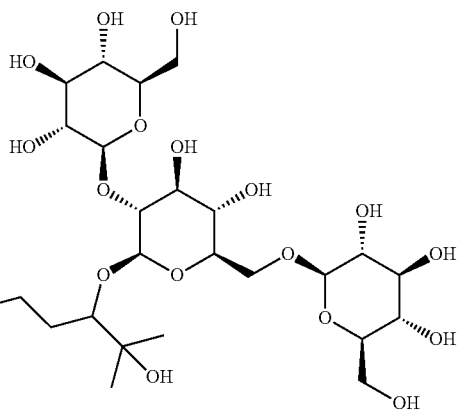
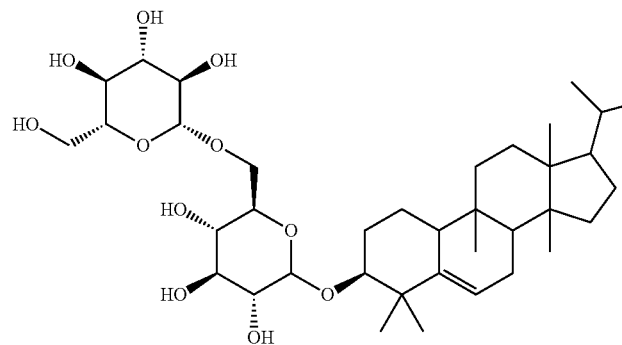
Compound Cc
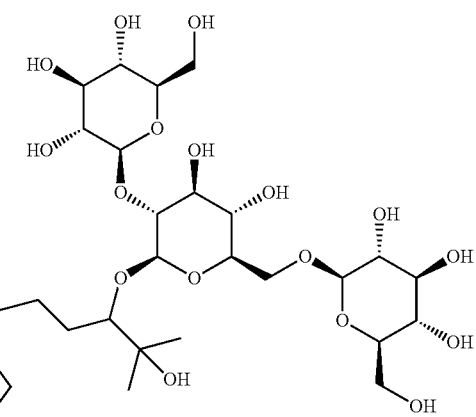
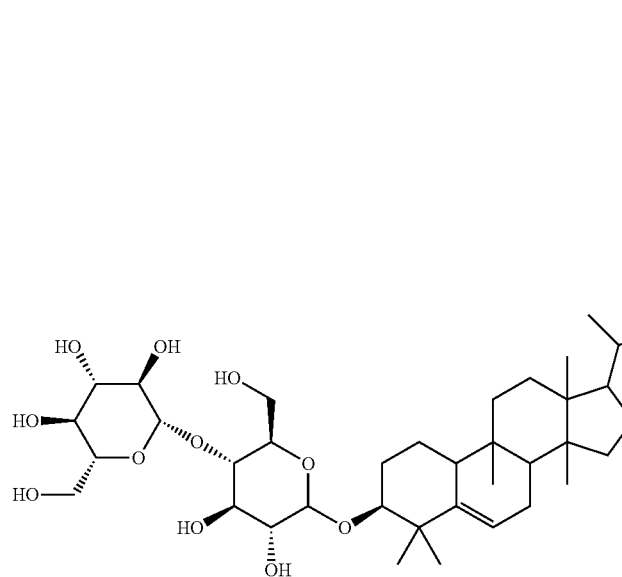

Compound Dd
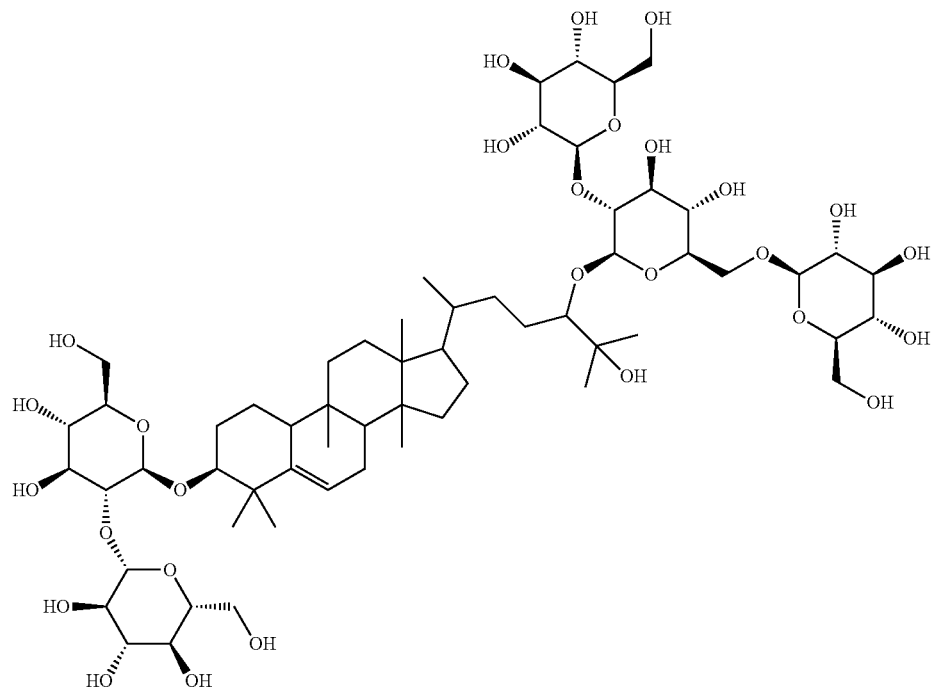
Compound Ee
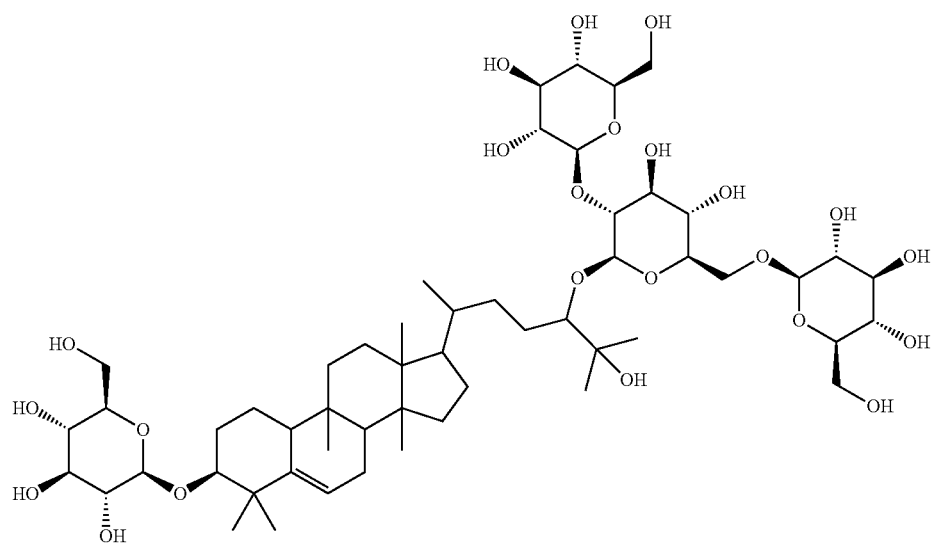

-continued
Compound Ff
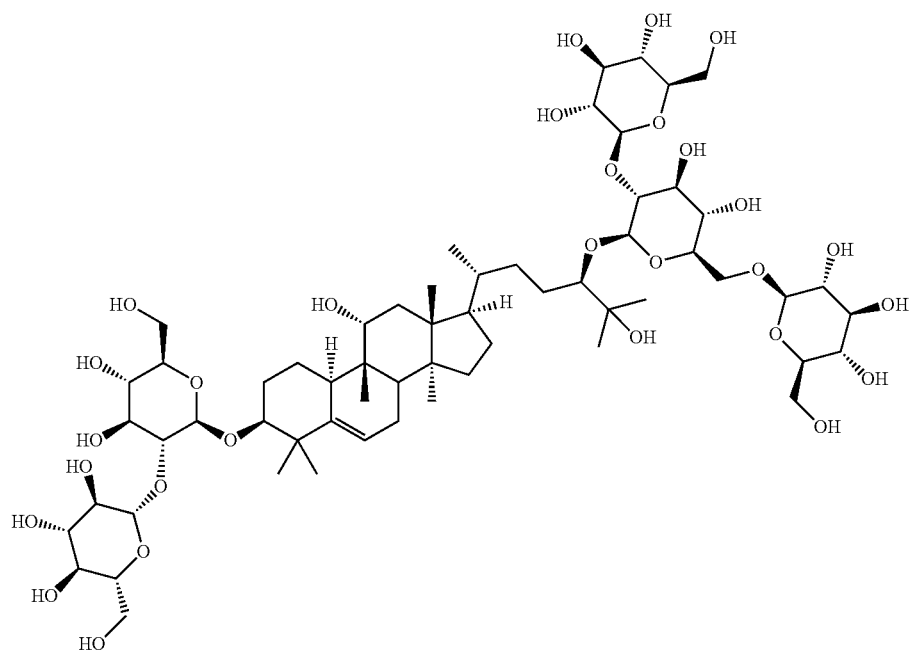
Compound Gg
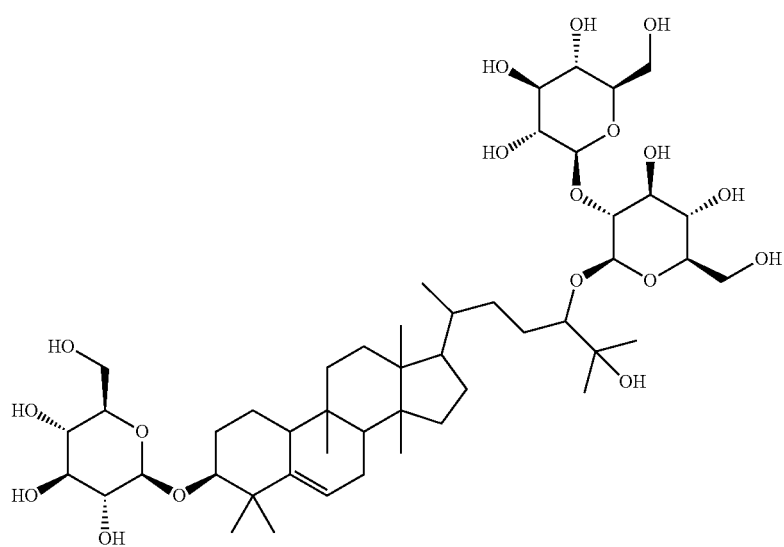
Compound Hh
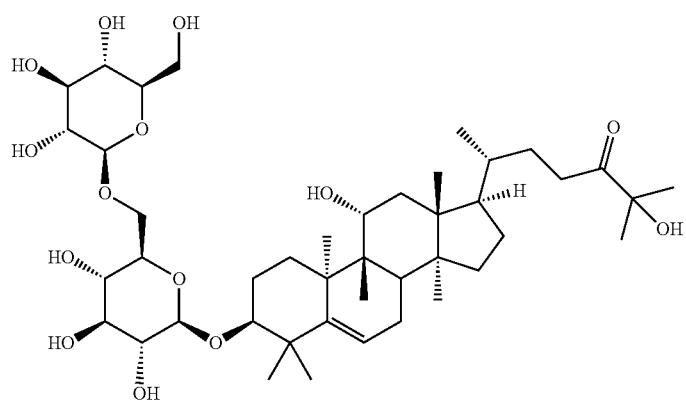

-continued
Compound Jj
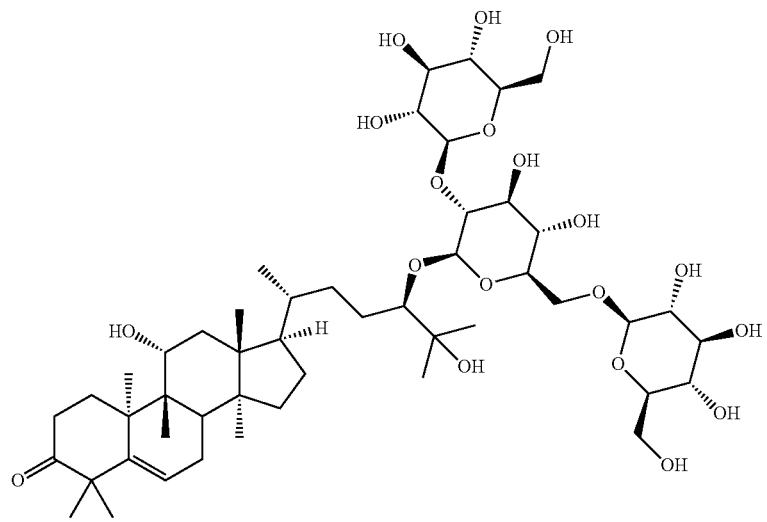
Compound Kk
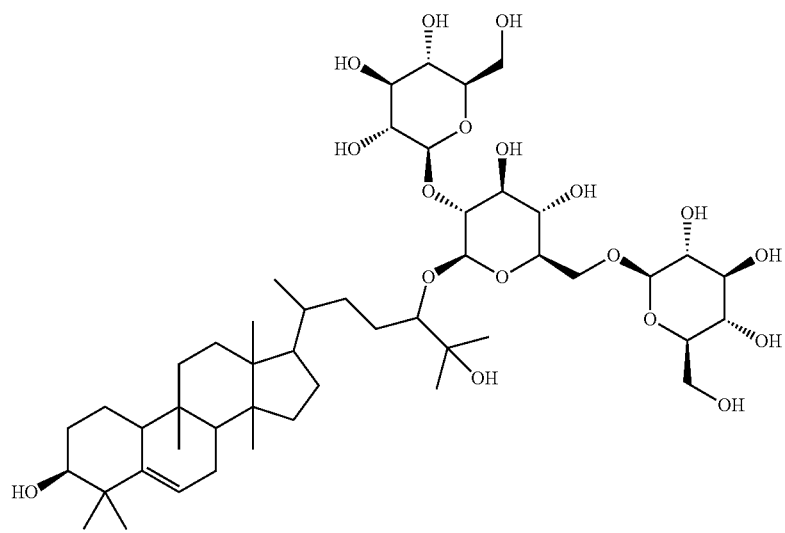
Compound Ll
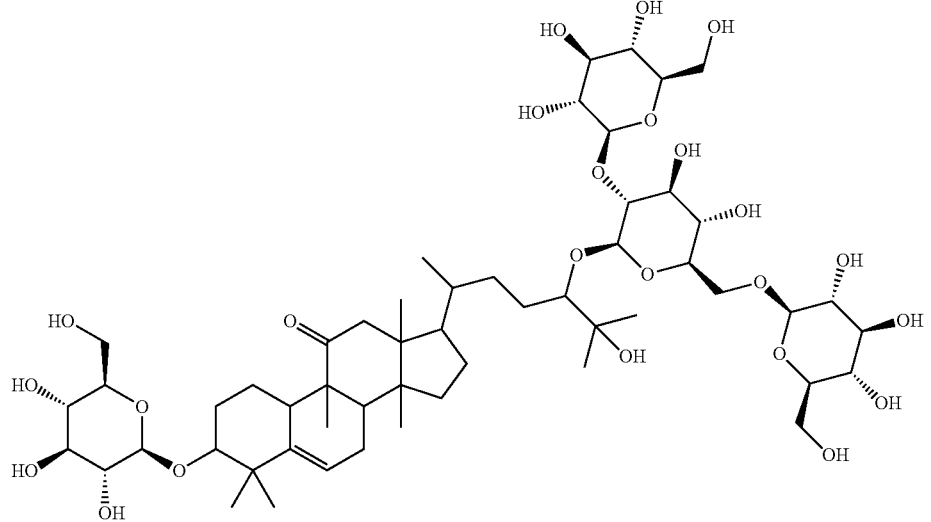

-continued

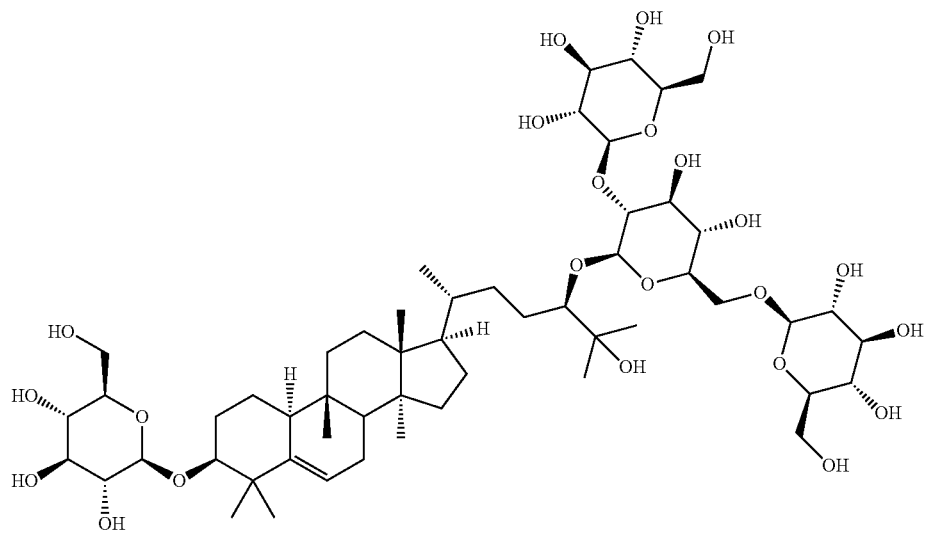

Compound Mm

Example 2

Organoleptic Test of the Compounds of Formula (I) Against Sucrose and Mogroside V The isolated pure compounds were dissolved in non-carbonated mineral water ("Fonsana Quelle") in a concentration of 0.4 mg/ml (400 ppm). The sweet taste of each sample was compared by a panel of 4 panelists with a solution of sucrose in a concentration of 20 mg/ml and with a solution of the known sweetener mogroside V (isolated by AnalytiCon from *Momordica grosvenori*) in a concentration of 0.1 mg/ml (100 ppm).

The sweetness was evaluated as follows:
3=sweeter than the control solution
2=sweetness comparable with the control solution
1=less sweet than the control solution but still sweet

TABLE 10

Organoleptic evaluation

| Compound | compared to sucrose* | compared to mogroside V* |
|---|---|---|
| Aa | 3 | 2 |
| Bb | 3 | 3 |
| Cc | 3 | 3 |
| Dd | 3 | 3 |
| Ee | 3 | 3 |
| Ff | 3 | 2 |
| Gg | 3 | 3 |
| Hh | 2 | 1 |
| Jj | 3 | 2 |
| Kk | 2 | 1 |
| Ll | 3 | 3 |
| Mm | 3 | 3 |

Example 3

Formulation Examples

The following Tables 11 to 14 provide some examples for oral compositions comprising at least one of the sweeteners disclosed before.

TABLE 11

Chewing gum, free of sugar; all amounts in % b.w.

| Composition | I | II | III |
|---|---|---|---|
| Gum base | 30.00 | 30.00 | 30.00 |
| Sorbit, powdered | 40.00 | 40.00 | 40.00 |
| Isomalt, powdered | 9.50 | 9.50 | 9.50 |
| Xylitol | 2.00 | 2.00 | 2.00 |
| Mannit D | 3.00 | 3.00 | 3.00 |
| Compound Aa | 0.10 | — | — |
| Compound Bb | — | 0.01 | — |
| Compound Cc | — | — | 0.05 |
| Emulgum/Plasticizing agent | 0.30 | 0.30 | 0.30 |
| Sorbitol (70% water) | 13.00 | 13.00 | 13.00 |
| Spearmint aroma | 1.00 | 1.00 | 1.00 |
| Glycerol | | Ad 100 | |

TABLE 12

Tooth paste; all amounts in % b.w.

| Composition | IV | V | VI |
|---|---|---|---|
| Glycerol | 20.00 | 20.00 | 20.00 |
| Solbrol M (sodium salt) | 0.15 | 0.15 | 0.15 |
| Sodium monofluor phosphate | 0.76 | 0.76 | 0.76 |
| Compound Dd | 0.20 | — | — |
| Compound Ee | — | 0.10 | — |
| Compound Ef | — | — | 0.01 |
| Dicalciumphosphate dihydrate | 36.00 | 36.00 | 36.00 |
| Aerosil 200 | 3.00 | 3.00 | 3.00 |
| Sodium carboxymethyl cellulose | 1.20 | 1.20 | 1.20 |
| Sodium lauryl sulfate | 1.30 | 1.30 | 1.30 |
| Peppermint aroma | 1.00 | 1.00 | 1.00 |
| Deionised water | | Ad 100 | |

TABLE 13

Mouth wash concentrate; all amounts in % b.w.

| Composition | VII | VIII | IX |
|---|---|---|---|
| Ethanol 96% | 42.00 | 42.00 | 42.00 |
| Cremophor RH 455 | 5.00 | 5.00 | 5.00 |

TABLE 13-continued

Mouth wash concentrate; all amounts in % b.w.

| Composition | VII | VIII | IX |
| --- | --- | --- | --- |
| Allantoin | 0.20 | 0.20 | 0.20 |
| Compound Gg | 0.10 | — | — |
| Compound Hh | — | 0.01 | — |
| Compound Jj | — | — | 0.05 |
| Colour L-Blue 5000 (1% in Wasser) | 0.03 | 0.03 | 0.03 |
| Spearmint aroma | 2.00 | 2.00 | 2.00 |
| Deionised water | | Ad 100 | |

TABLE 14

Hard boiled candy, sugar-free; all amounts in % b.w.

| Composition | X | XI | XII |
| --- | --- | --- | --- |
| Isomalt | 94.98 | 94.98 | 94.98 |
| Xylitol | 2.40 | 2.40 | 2.40 |
| Compound Kk | 0.10 | — | — |
| Compound Ll | — | 0.01 | — |
| Compound Mm | — | — | 0.05 |
| Citric acid | 0.050 | 0.050 | 0.050 |
| Cherry aroma | 0.25 | 0.25 | 0.25 |
| Water | | Ad 100 | |

What claimed is:

1. A method of sweetening or enhancing sweetening effect, comprising
incorporating a sweetener compound of the following formula (I)

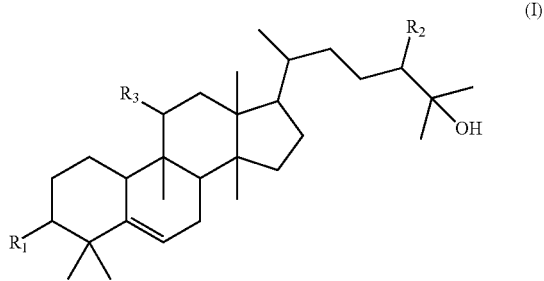

wherein $R_1$ is glucopyranosyl, $R_2$ is glucopyranosyl-1-(1→2)-[glucopyranosyl-(1→6)]-glucopyranosyl, and $R_3$ denotes hydrogen,
into a composition to sweeten or enhance the sweeting effect in the composition.

2. A method according claim 1, wherein the compound of formula (I) is
2-(4,5-dihydroxy-2-(2-hydroxy-2-methyl-6-(4,4,9,13,14-pentamethyl-3-(3,4,5-trihydroxy-6-(hydroxymethyl) tetrahydro-2H-pyran-2-yloxy)-2,3,4,7,8,9,10,11,12,13, 14,15,16,17-tetradecahydro-1H-cyclopenta[a]phena-nthren-17-yl)heptan-3-yloxy)-6-((3,4,5-trihydroxy-6-(hydroxymethyl)tetrahydro-2H-pyran-2-yloxy)methyl) tetrahydro-2H-pyran-3-yloxy)-6-(hydroxymethyl)tet-rahydro-2H-pyran-3,4,5-triol (compound E).

3. A method according to claim 1, comprising the additional step of adding aroma compounds and/or flavouring agents and/or sweeteners and/or sweet-tasting substances.

4. A method according to claim 1, wherein the sweetener is an extract obtained aqueous and/or alcoholic extraction of the plant Momordica grosvenorii (Synononym Siraitia grosvenori).

5. A method according to claim 4, wherein the compound of formula (I) is
(2S,3R,4S,5S,6R)-2-((2S,3R,4S,5S,6R)-4,5-dihydroxy-2-((3R,6R)-2-hydroxy-2-methyl-6-((3S,8R,9R,13R, 14S,17R)-4,4,9,13,14-pentamethyl-3-((2R,3R,4S,5S, 6R)-3,4,5-trihydroxy-6-(hydroxymethyl)tetrahydro-2H-pyran-2-yloxy)-2,3,4,7,8,9,10,11,12,13,14,15,16, 17-tetradecahydro-1H-cyclopenta[a]phenanthren-17-yl)heptan-3-yloxy)-6-(((2R,3R,4S,5S,6R)-3,4,5-trihy-droxy-6-(hydroxymethyl)tetrahydro-2H-pyran-2-ylo-xy)methyl)tetrahydro-2H-pyran-3-yloxy)-6-(hydrox-ymethyl)tetrahydro-2H-pyran-3,4,5-triol (compound Ee).

6. A method according to claim 1, comprising the additional step of
administering the composition to an individual in an effective amount sufficient to produce the desired degree of sweetness.

* * * * *